United States Patent
Wang et al.

(10) Patent No.: US 10,933,071 B2
(45) Date of Patent: *Mar. 2, 2021

(54) POLYETHYLENE GLYCOL-CONJUGATED GLUCOCORTICOID PRODRUGS AND COMPOSITIONS AND METHODS THEREOF

(71) Applicant: Board of Regents of the University of Nebraska, Lincoln, NE (US)

(72) Inventors: Dong Wang, Omaha, NE (US); Fang Yuan, Wheaton, MD (US); Zhenshan Jia, Omaha, NE (US); Xiaobei Wang, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/694,722

(22) Filed: Nov. 25, 2019

(65) Prior Publication Data

US 2020/0085842 A1 Mar. 19, 2020

Related U.S. Application Data

(63) Continuation of application No. 15/775,647, filed as application No. PCT/US2016/061728 on Nov. 12, 2016, now Pat. No. 10,485,809.

(60) Provisional application No. 62/254,512, filed on Nov. 12, 2015.

(51) Int. Cl.
| | |
|---|---|
| *A61K 31/57* | (2006.01) |
| *C07J 41/00* | (2006.01) |
| *A61K 9/107* | (2006.01) |
| *A61K 47/10* | (2017.01) |
| *A61K 47/34* | (2017.01) |
| *C07J 51/00* | (2006.01) |

(52) U.S. Cl.
CPC ............ *A61K 31/57* (2013.01); *A61K 9/1075* (2013.01); *A61K 47/10* (2013.01); *A61K 47/34* (2013.01); *C07J 41/0005* (2013.01); *C07J 41/0016* (2013.01); *C07J 51/00* (2013.01)

(58) Field of Classification Search
CPC ............................ A61K 31/57; C07J 41/0005
See application file for complete search history.

(56) References Cited

U.S. PATENT DOCUMENTS 8,796,248 B2      8/2014  Zhang et al.
10,485,809 B2 *  11/2019  Wang .................. C07J 41/0005

FOREIGN PATENT DOCUMENTS

WO    2004037843 A2    5/2004
WO    2009045539 A2    4/2009

OTHER PUBLICATIONS

Liu et al., "Syntheses of Click PEG-Dexamethasone Conjugates for teh Treatment of Rheumatoid Arthritis," Biomacromolecules (Oct. 11, 2010); 11(10);2621-2628.
Zhang et al. (2014): STN International (Columbus, Ohio), HCAPLUS database, Accession No. 2016: 1947554.

* cited by examiner

*Primary Examiner* — Golam M Shameem
(74) *Attorney, Agent, or Firm* — Fox Rothschild LLP

(57) ABSTRACT

Polyethylene glycol (PEG)-conjugated glucocorticoid prodrugs, methods of preparation, and use for the treatment of diseases and disorders are disclosed. In particular, PEG-conjugated dexamethasone compounds and methods of using them for treating inflammatory and autoimmune diseases, including but not limited to lupus, are disclosed.

21 Claims, 9 Drawing Sheets

POLYETHYLENE GLYCOL-CONJUGATED GLUCOCORTICOID PRODRUGS AND COMPOSITIONS AND METHODS THEREOF

CROSS REFERENCE TO RELATED APPLICATIONS

This application is a Continuation of U.S. patent application Ser. No. 15/775,647, filed on May 11, 2018, which is the U.S. National Phase of International Patent Application No. PCT/US2016/061728, Filed on Nov. 12, 2016, which claims priority under 35 U.S.C. § 119(e) to U.S. Provisional Patent Application No. 62/254,512, filed on Nov. 12, 2015, all of which are herein incorporated by reference in their entirety.

FIELD OF THE INVENTION

The present invention relates to glucocorticoid prodrugs and methods of using the prodrugs for treating patients having an inflammatory disease, including but not limited to lupus.

BACKGROUND OF THE INVENTION

Lupus is a challenging autoimmune rheumatic disease in clinic for which current therapies are unsatisfactory with respect to both remission induction and unwanted toxicities. It is characterized by B and T cell hyperactivation, overproduction of autoantibodies, and the deposition of immune complexes in various tissues/organs. The symptoms of lupus are highly heterogeneous including skin rash, arthritis, pericarditis, neuropsychiatric disorders and nephritis. It is estimated that 1.5 million of Americans are affected by lupus and the number of patients is continuously increasing.

Lupus nephritis (LN), one of the most devastating complications of lupus, and the leading cause of morbidity and mortality in lupus patients, affects between 30-60% of lupus patients in terms of immunosuppression and direct mortality. In the US, approximately 35% adult lupus patients have clinical evidence of nephritis at the time of diagnosis, and an additional 15-25% will develop nephritis within 10 years of diagnosis. LN is initiated by immune complex deposition within the glomeruli and tubules of the kidney and subsequent activation of the immune effector cells (such as macrophages and neutrophils) that leads to damage to renal tissues. If not properly managed, lupus nephritis can rapidly progress to impaired renal function and eventually causing renal failure.

While clinicians have utilized many classes of drugs to manage lupus, only a few have been approved by US FDA specifically for the disease. They include aspirin, belimumab (or Benlysta®, a human monoclonal antibody that inhibits B-cell activating factor), antimalarials (e.g. chloroquine) and glucocorticoids (GC, e.g. prednisone, dexamethasone). Among these treatment options, GC is one of the most potent and widely used drugs for lupus. In American College of Rheumatology (ACR)'s new guidelines for clinical management of lupus nephritis, the recommended treatment regimen consists of a pulse GC treatment followed by low/high-dose daily GC plus an immunosuppressive medication. Compared to the previous guidelines, new immunosuppressants (e.g. mycophenolate mofetil) have been added as alternatives to cyclophosphamide. No alternatives, however, have been recommended for GC. Comparing to the wide applications of GC in most lupus symptoms, the clinical benefits of belimumab in treatment of lupus nephritis has not been well established. NSAIDs, on the other hand, are contraindicated for lupus nephritis due to their renal toxicities.

Due to their potent anti-inflammatory efficacy and the lack of an alternative therapy, GC continues to be the mainstay of clinical management of lupus. Some lupus pathologies, such as arthritis and skin rash can be treated effectively with short-term GC. More severe lupus complications, such as progressive nephritis necessitates long-term GC therapy, which is frequently associated with serious side effects involving the endocrine, cardiovascular, hematopoietic and musculoskeletal systems. These adverse events contribute significantly to morbidity among lupus patients.

The actions of GC are thought to be mediated through two distinct pathways: transactivation and transrepression. It has been postulated that transrepression primarily mediates the anti-inflammatory effects of GC whereas transactivation is responsible for the GC-associated side effects. Compounds that can preferentially activate the transrepression relative to the transactivation pathway have been developed. Nevertheless, these compounds do not exhibit strict pathway selectivity and still elicit GC-related side effects.

SUMMARY OF THE INVENTION

To address the various foregoing problems, the present application discloses glucocorticoid (GC) prodrugs and methods of using them for treatment of lupus and LN. These include a polyethylene glycol (PEG)-based macromolecular prodrug (PEG-DiDex) of dexamethasone (Dex), which self-assembles into micelles.

In one aspect, the present invention provides a compound of formula (I) or (XII):

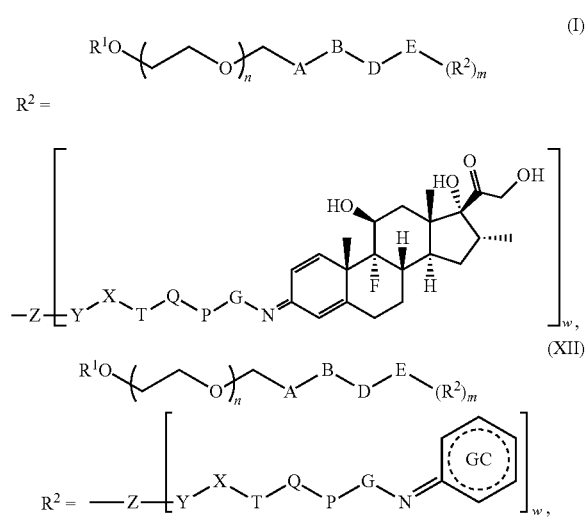

or a pharmaceutically acceptable salt, solvate, or prodrug thereof, wherein:
n is an integer from 3 to 500;
m is an integer from 1 to 5;
w is an integer from 1 to 5;
GC is a moiety of a glucocorticoid drug molecule
A is absent, $C_1$-$C_6$ alkylene, or $C_6$-$C_{10}$ arylene;
B is absent, $NR^4$, O, or C(O);
D is absent, $NR^4$, O, C(O), or $CR^5R^5$;
E is absent, $C_1$-$C_6$ alkylene, or a linker comprising a branched structure capable of connecting to two or more $R^2$ groups, said linker optionally comprising one, two, or more heteroatoms independently selected from the group consisting of O, S, and N;

G is absent, $NR^4$, or O;
P is absent or C(O);
Q is absent, $C_6$-$C_{10}$ arylene, or $C_1$-$C_6$ alkylene;
T is absent, $C_1$-$C_6$ alkylene, $C_6$-$C_{10}$ arylene, or C(O);
X is absent, O, S, or $NR^4$;
Y is absent, C(O), $C_6$-$C_{10}$ arylene, or $C_1$-$C_6$ alkylene;
Z is absent, $NR^4$, O, $C_1$-$C_6$ alkylene, or a linker comprising a branched structure capable of connecting to one or more dexamethasone moieties, said linker optionally comprising one or more heteroatoms independently selected from the group consisting of O, S, and N;
$R^1$ is H, $C_1$-$C_6$ alkyl, $C_2$-$C_6$ alkenyl, $C_2$-$C_6$ alkynyl, $C_6$-$C_{10}$ aryl, 5-10 membered heteroaryl, or 5-10 membered heterocyclyl, each group except H optionally substituted by one to five substituents independently selected from the group consisting of $C_1$-$C_4$ alkyl, $C_1$-$C_4$ haloalkyl, halogen, oxo (=O), —$NR^aR^b$, —$NO_2$, —CN, —$OR^3$, and —$SR^3$; or alternatively, $R^1$ is —$CH_2$-A-B-D-E-$(R^2)_m$;
$R^3$ at each occurrence is independently H, $C_1$-$C_4$ alkyl, or $C_1$-$C_4$ haloalkyl;
$R^4$ at each occurrence is independently H or $C_1$-$C_4$ alkyl;
$R^5$ at each occurrence is independently H, $C_1$-$C_4$ alkyl, or $C_1$-$C_4$ haloalkyl;
$R^a$ and $R^b$ are each independently H or $C_1$-$C_4$ alkyl; and wherein when any of groups A, B, D, E, G, P, Q, T, X, Y, and Z is absent, its two available adjacent groups are single-bonded to each other directly.

In another aspect, the present invention provides a pharmaceutical composition comprising a compound according to any one embodiment described herein, or a pharmaceutically acceptable salt, solvate, or prodrug thereof, and a pharmaceutically acceptable carrier, adjuvant, diluent, or vehicle.

In another aspect, the present invention provides a method of treating an autoimmune disease and/or inflammatory disorder, comprising administering to a subject in need of treatment a therapeutically effective amount of a compound according to any embodiment disclosed here, or a pharmaceutically acceptable salt, solvate, or prodrug thereof.

In another aspect, the present invention provides a method of treating a disease or disorder associated with lupus, comprising administering to a subject in need of treatment a therapeutically effective amount of the pharmaceutical composition of any embodiment disclosed herein.

In another aspect, the present invention provides use of a compound according to any embodiment or any embodiment combinations disclosed here, or a pharmaceutically acceptable salt, solvate, or prodrug thereof, in the manufacture of a medicament for treatment of a disease or disorder, especially those associated with lupus.

The PEG-based macromolecular prodrug of dexamethasone (Dex) overcomes various challenges, for example, their accompanying severe toxicities, through GC prodrug nanomedicine development, in order to more fully realize the therapeutic potential of GC in clinical management of lupus nephritis. Without intending to be bound by theory, the present invention is in part based on a hypothesis that the Extravasation of the nanomedicine through Leaky Vasculature at inflammation and subsequent Inflammatory cell-mediated Sequestration (ELVIS) would dramatically alter the pharmacokinetics/biodistribution (PK/BD) profile of the parent drug, favoring specific accumulation in the inflamed tissues/organs, and enhanced molecular weight associated with the non-immunogenicity of PEG chains would potentially improve drug retention in kidney and prolong the blood circulation time. Specifically, the amphiphilic molecule self-assembles into micelles. When tested in lupus prone NZB/W F1 mice with severe nephritis, the monthly treatment demonstrated superior therapeutic efficacy in improving kidney function than dose equivalent daily Dex treatment, with no GC-associated side effect observed.

Other aspects, benefits, and advantages of the present invention will be better appreciated in view of the following drawings, detailed description, and claims.

DETAILED DESCRIPTION OF THE INVENTION

Figure 1:
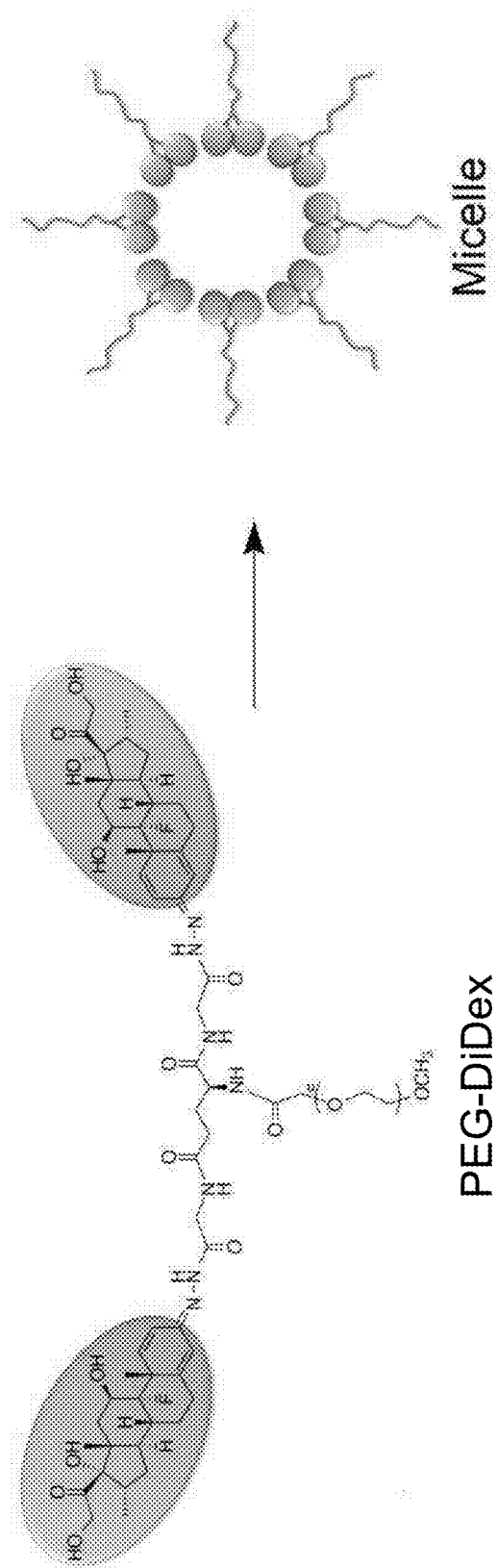
FIG. 1 illustrates the design of polyethylene glycol (PEG)-based amphiphilic dexamethasone prodrug PEG-DiDex, which can self-assemble into micelles.

The glucocorticoid prodrugs conjugated to polyethylene glycol have been found to possess superior therapeutic efficacy and greatly reduced toxicity as compared with the parent drug.

Specifically, optical imaging, immunohistochemistry and flow cytometry studies reveal that the near-infrared dye labeled PEG-DiDex micelle primarily distributes to the inflamed kidneys after systemic administration, with intra-glomerular mesangial cells and proximal tubule epithelial cells chiefly responsible for the intracellular sequestration of the prodrug inside the kidneys. For efficacy and safety evaluation, the prodrug micelle was given monthly to NZB/W F1 female mice (28 weeks old) via tail vein injection. Dose equivalent daily dexamethasone phosphate sodium i.v. administration and saline were used as controls. When compared to Dex treatment, PEG-DiDex markedly improved the survival of NZB/W F1 mice and is significant more effective in normalizing albuminuria; no significant systemic toxicity of GCs (i.e. WBC reduction, total IgG reduction, adrenal gland atrophy and osteopenia) was observed in the prodrug treated group. PEG-DiDex treated animals also exhibit lower serum levels of proinflammatory cytokines (e.g. MCP-1, IFN-β, IFN-γ, etc.) and clear histological indication of nephritis resolution after 2 months of treatment. But it has no impact on the serum anti-dsDNA antibody level. Collectively, these evidences suggest that the novel prodrug micelle design of PEG-DiDex can dramatically alter the biodistribution profile of Dex by passively targeting the drug to the inflamed kidneys. The nephrotropic distribution pattern of PEG-DiDex potentiates and prolongs the local anti-inflammatory effect of Dex within kidney pathology. Its outstanding safety profile may be attributed to the substantially reduced systemic exposure to Dex.

In one aspect, the present invention provides a compound of formula (I):

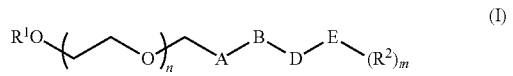

(I)

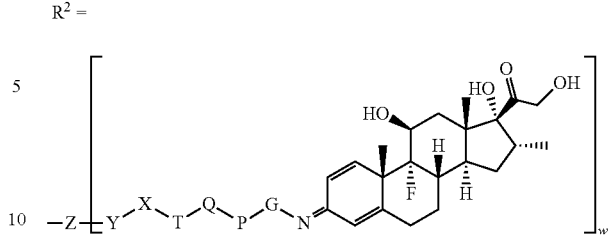

or a pharmaceutically acceptable salt, solvate, or prodrug thereof, wherein:

n is an integer from 3 to 500;
m is an integer from 1 to 5;
w is an integer from 1 to 5;
A is absent, $C_1$-$C_6$ alkylene, or $C_6$-$C_{10}$ arylene;
B is absent, $NR^4$, O, or C(O);
D is absent, $NR^4$, O, C(O), or $CR^5R^5$;
E is absent, $C_1$-$C_6$ alkylene, or a linker comprising a branched structure capable of connecting to two or more $R^2$ groups, said linker optionally comprising one, two, or more heteroatoms independently selected from the group consisting of O, S, and N;
G is absent, $NR^4$, or O;
P is absent or C(O);
Q is absent, $C_6$-$C_{10}$ arylene, or $C_1$-$C_6$ alkylene;
T is absent, $C_1$-$C_6$ alkylene, $C_6$-$C_{10}$ arylene, or C(O);
X is absent, O, S, or $NR^4$;
Y is absent, C(O), $C_6$-$C_{10}$ arylene, or $C_1$-$C_6$ alkylene;
Z is absent, $NR^4$, O, $C_1$-$C_6$ alkylene, or a linker comprising a branched structure capable of connecting to one or more dexamethasone moieties, said linker optionally comprising one or more heteroatoms independently selected from the group consisting of O, S, and N;
$R^1$ is H, $C_1$-$C_6$ alkyl, $C_2$-$C_6$ alkenyl, $C_2$-$C_6$ alkynyl, $C_6$-$C_{10}$ aryl, 5-10 membered heteroaryl, or 5-10 membered heterocyclyl, each group except H optionally substituted by one to five substituents independently selected from the group consisting of $C_1$-$C_4$ alkyl, $C_1$-$C_4$ haloalkyl, halogen, oxo (=O), —$NR^aR^b$, —$NO_2$, —CN, —$OR^3$, and —$SR^3$; or alternatively, $R^1$ is —$CH_2$-A-B-D-E-$(R^2)_m$;
$R^3$ at each occurrence is independently H, $C_1$-$C_4$ alkyl, or $C_1$-$C_4$ haloalkyl;
$R^4$ at each occurrence is independently H or $C_1$-$C_4$ alkyl;
$R^5$ at each occurrence is independently H, $C_1$-$C_4$ alkyl, or $C_1$-$C_4$ haloalkyl;
$R^a$ and $R^b$ are each independently H or $C_1$-$C_4$ alkyl; and
wherein when any of groups A, B, D, E, G, P, Q, T, X, Y, and Z is absent, its two available adjacent groups are single-bonded to each other directly.

In some embodiments of this aspect, E is a linker comprising a branched structure capable of covalently bonding to two or more $R^2$ groups, said linker optionally comprising one or more heteroatoms independently selected from the group consisting of O, S, and N.

In some embodiments of this aspect, Z is a linker comprising a branched structure capable of covalently bonding to two or more dexamethasone moieties, said linker optionally comprising one or more heteroatoms independently selected from the group consisting of O, S, and N.

In some embodiments of this aspect, E and Z are each independently selected from the group consisting of absent, $C_1$-$C_4$ alkylene, an amino acid-based linker, a citric acid-based linker, a glycerol-based linker, a tris(2-aminoethyl)

amine-based linker, a pentaerythritol-based linker, and a pentetic acid-based linker, respectively having a formula as follows:
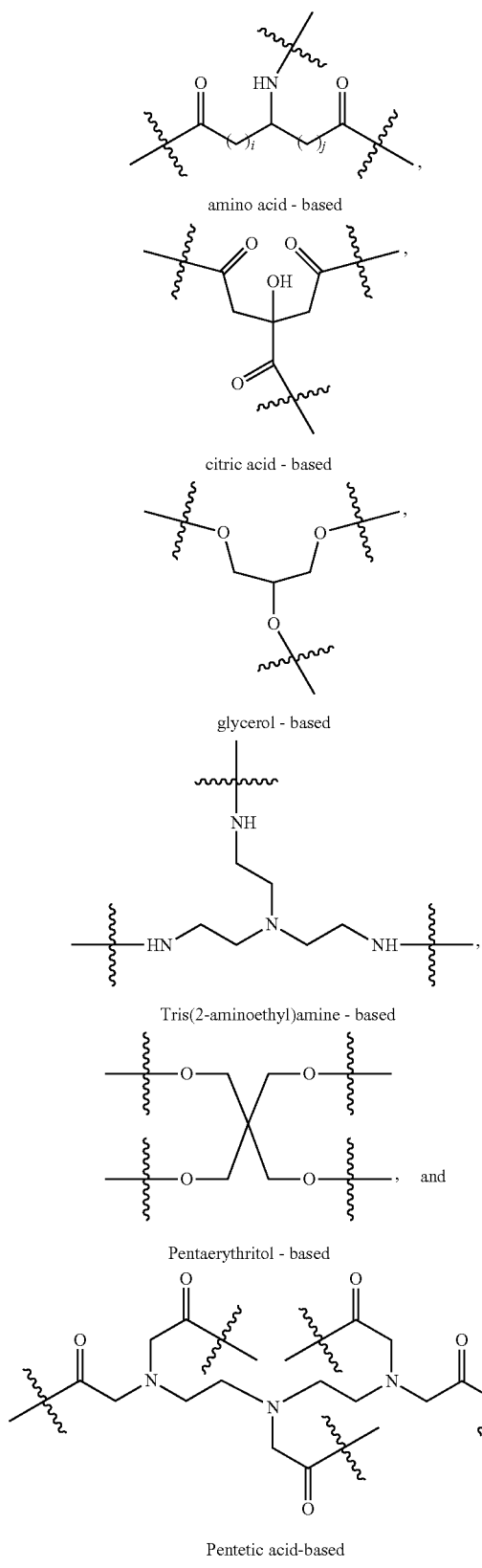
wherein i and j are each independently 0 or an integer select from 1 to 5.
In some embodiments of this aspect,
w is 1;
Z is absent or $C_1$-$C_4$ alkylene;
E is selected from the group consisting of:
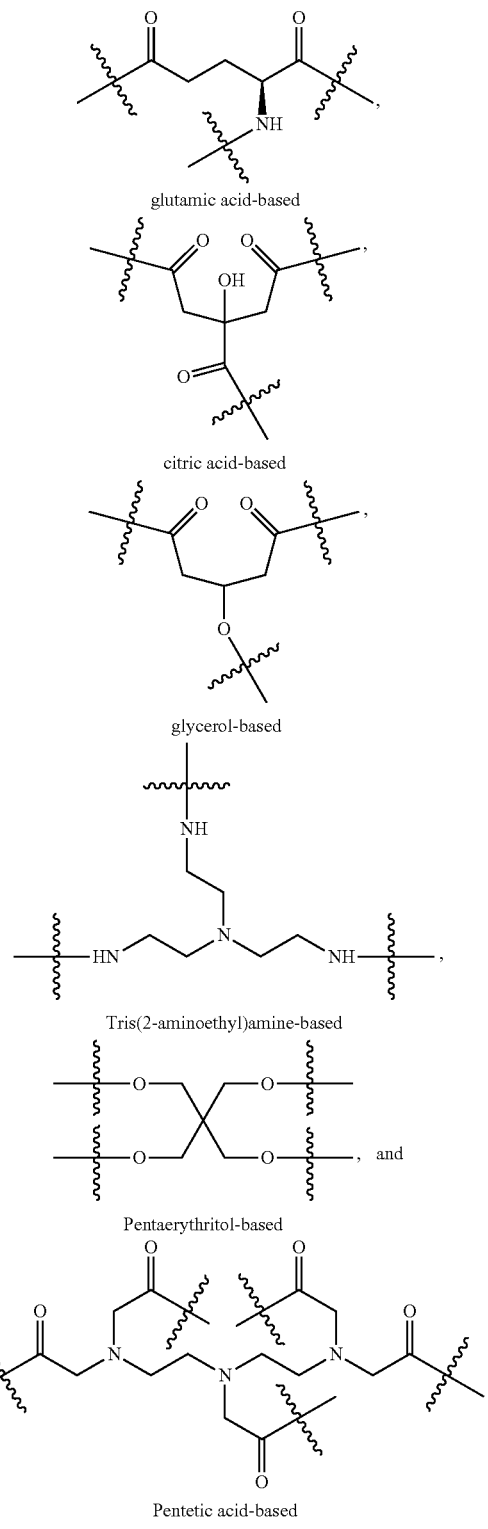

In some embodiments of this aspect, m is 1; w is 1; and A, B, D, E, and Z are all absent, characterized by formula (II):

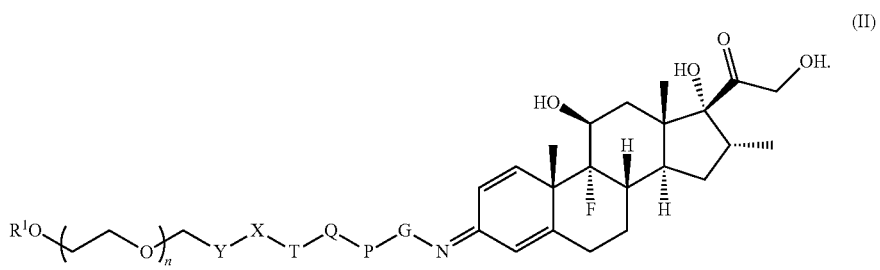

In some embodiments of this aspect, $R^1$ is $CH_3$; Y is C(O); X is NH; and T, Q, P, and G are all absent, characterized by formula:

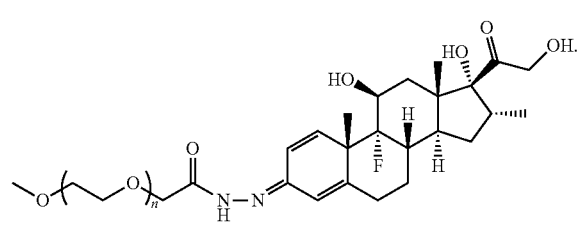

In some embodiments of this aspect, A is C(O); B and D are absent; E is the amino acid based linker; m is 2; w is 1; Z and Y are absent, and X is NH, characterized by formula (III):

i=0 or an integer from 1 to 5;
j=0 or an integer from 1 to 5;
G=absent, $NR^4$, or O;
P=absent or C(O);
Q=absent, $C_6$-$C_{10}$ arylene, or $C_1$-$C_6$ alkylene;
T=absent, $C_1$-$C_6$ alkylene, $C_6$-$C_{10}$ arylene, or C(O);
X=absent, O, S, or $NR^4$;
Y=absent or $C_1$-$C_6$ alkylene;
$R^1$=H or $C_1$-$C_6$ alkyl, $C_2$-$C_6$ alkenyl, $C_2$-$C_6$ alkynyl, $C_6$-$C_{10}$ aryl, or 5-10 membered heteroaryl, 5-10 membered heterocyclyl, each group except H optionally substituted by one to three substituents independently selected from the group consisting of $C_1$-$C_4$ alkyl, $C_1$-$C_4$ haloalkyl, halogen, oxo (=O), $-NR^aR^b$, $-NO_2$, $-CN$, $-OR^3$, and $-SR^3$;
$R^3$ at each occurrence is independently H, $C_1$-$C_4$ alkyl, or $C_1$-$C_4$ haloalkyl;
$R^4$ at each occurrence is independently H or $C_1$-$C_4$ alkyl;
$R^a$ and $R^b$ are each independently H or $C_1$-$C_4$ alkyl; and
wherein when any of groups G, P, Q, T, X, and Y is absent, its two available adjacent groups are single-bonded to each other directly.

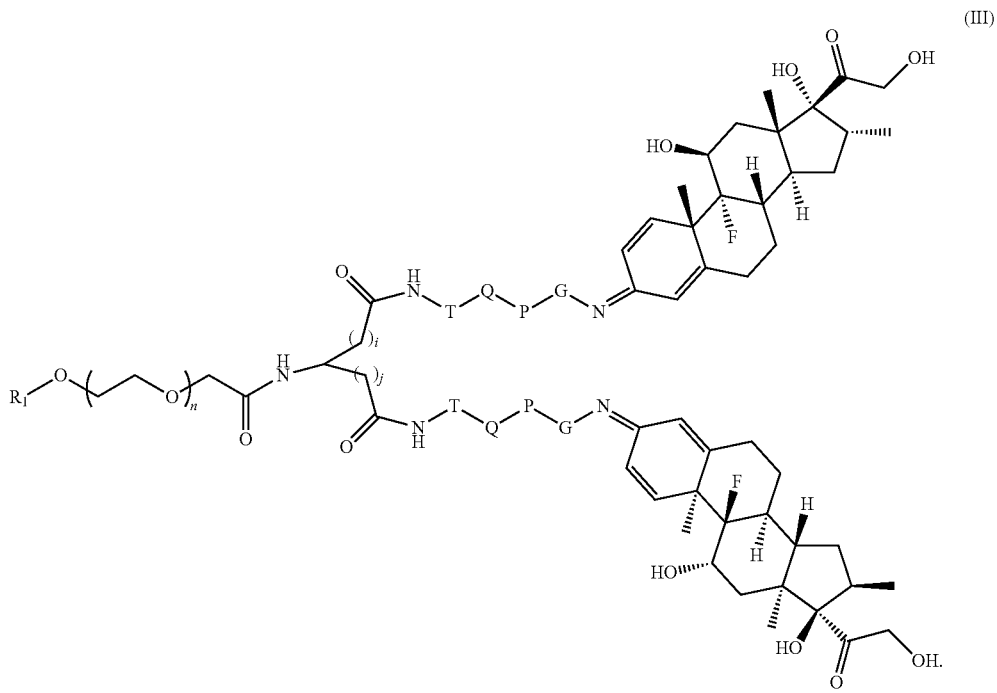

or a pharmaceutically acceptable salt, solvate, or prodrug thereof, wherein:

In some embodiments of this aspect, i is 0; j is 2; E is a glutamic acid based linker having a formula:

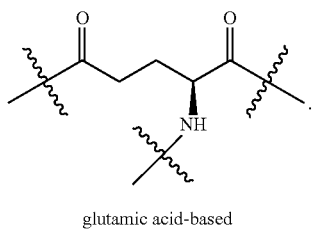 [SMILES: *N[C@@H](CCC(*)=O)C(*)=O]

glutamic acid-based

In some embodiments of this aspect, i is 0, j is 2, X is NH; and Q is methylene, P is C(O), G is NH, the compound characterized by formula:

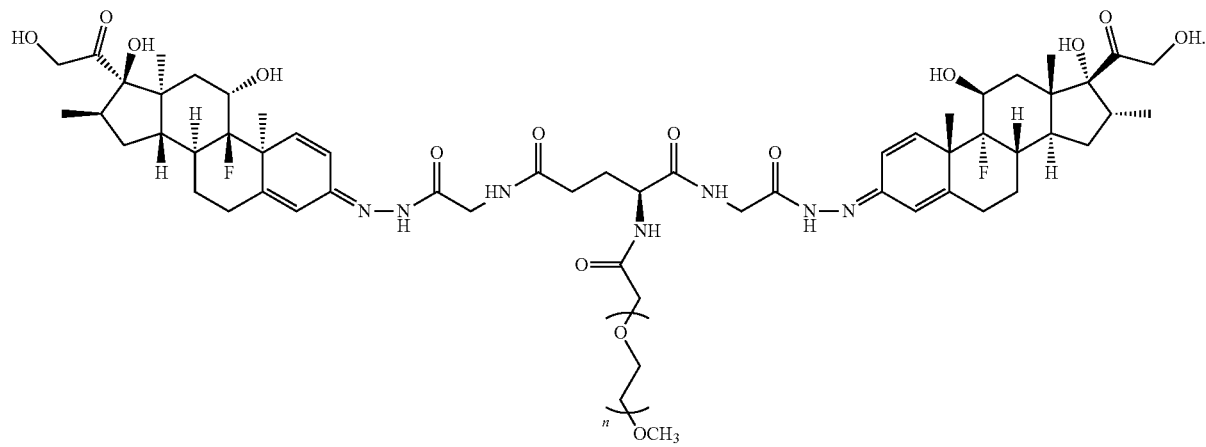

In some embodiments of this aspect, A is methylene, B is NH, m is 1, w is 2, E is a citric acid based linker, Z is NH, the compound characterized by formula (IV):

or a pharmaceutically acceptable salt, solvate, or prodrug thereof, wherein:

i=0 or an integer from 1 to 5;
j=0 or an integer from 1 to 5;
G=absent, $NR^4$, or O;
P=absent or C(O);
Q=absent, $C_6$-$C_{10}$ arylene, or $C_1$-$C_6$ alkylene;
T=absent, $C_1$-$C_6$ alkylene, $C_6$-$C_{10}$ arylene, or C(O);
X=absent, O, S, or $NR^4$;
Y=absent or $C_1$-$C_6$ alkylene;
$R^1$=H or $C_1$-$C_6$ alkyl, $C_2$-$C_6$ alkenyl, $C_2$-$C_6$ alkynyl, $C_6$-$C_{10}$ aryl, or 5-10 membered heteroaryl, 5-10 membered heterocyclyl, each group except H optionally substituted by one to three substituents independently selected from the group consisting of $C_1$-$C_4$ alkyl, $C_1$-$C_4$ haloalkyl, halogen, oxo (=O), —$NR^aR^b$, —$NO_2$, —CN, —$OR^3$, and —$SR^3$;

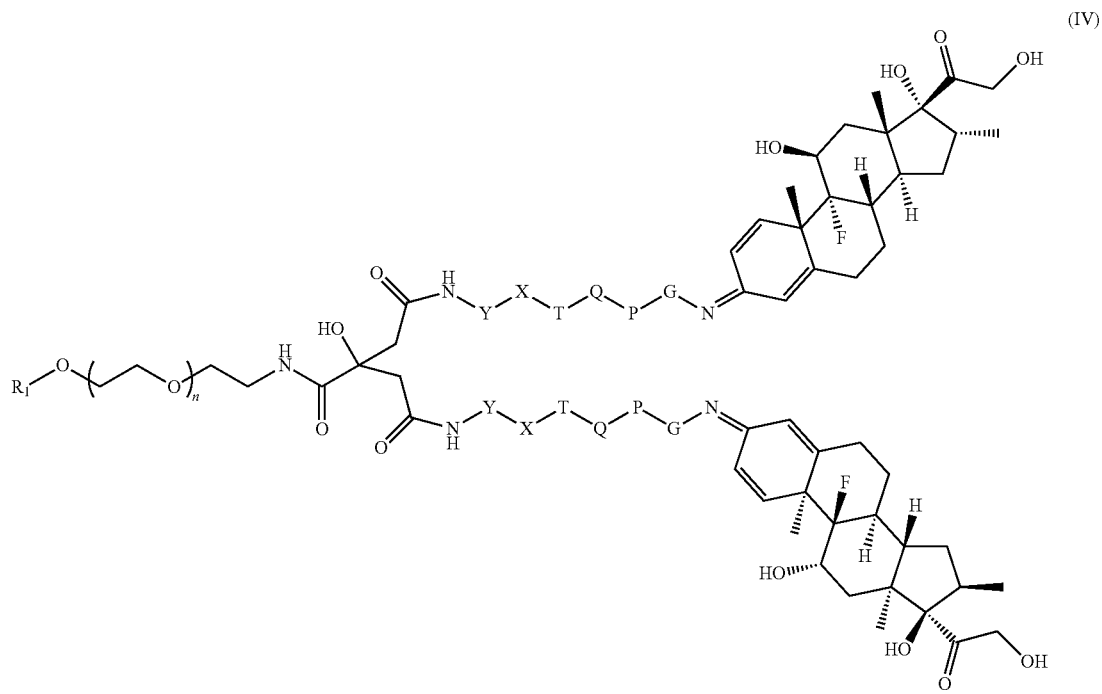

$R^3$ at each occurrence is independently H, $C_1$-$C_4$ alkyl, or $C_1$-$C_4$ haloalkyl;

$R^4$ at each occurrence is independently H or $C_1$-$C_4$ alkyl;

$R^a$ and $R^b$ are each independently H or $C_1$-$C_4$ alkyl; and wherein when any of groups G, P, Q, T, X, and Y is absent, its two available adjacent groups are single-bonded to each other directly.

In some embodiments of this aspect, G, P, Q, T, X, and Y are all absent, the compound characterized by formula:

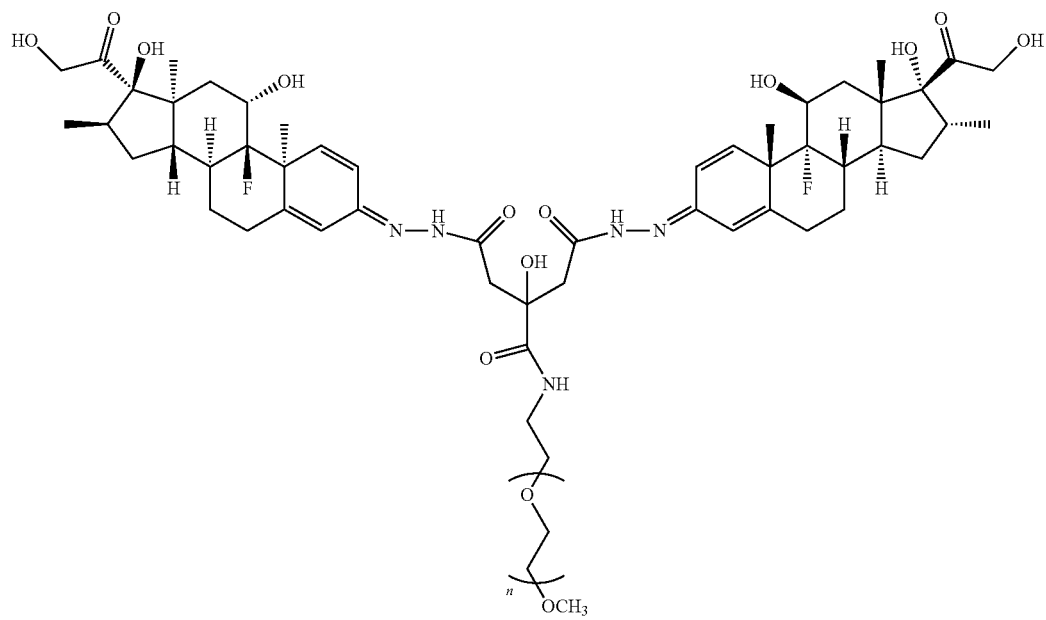

In some embodiments of this aspect, m is 3, w is 1, A is methylene, B is NH, D is C(O) and E is a pentaerythritol-based linker, the compound is characterized by formula (V):

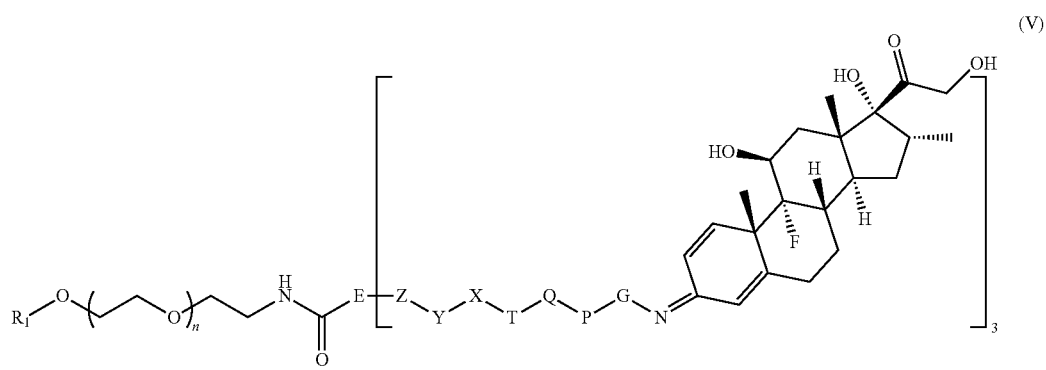

In some embodiments of this aspect, Y is C(O); X is NH; and G, P, Q, and T are all absent, the compound characterized by formula:

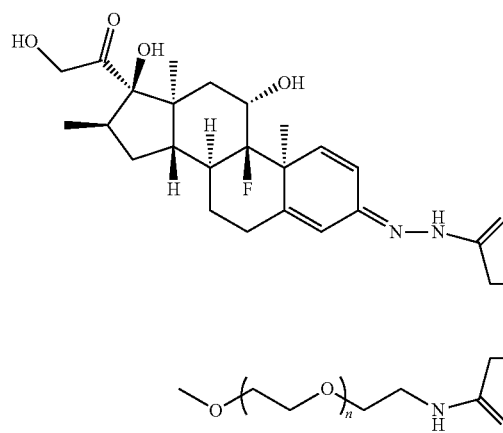
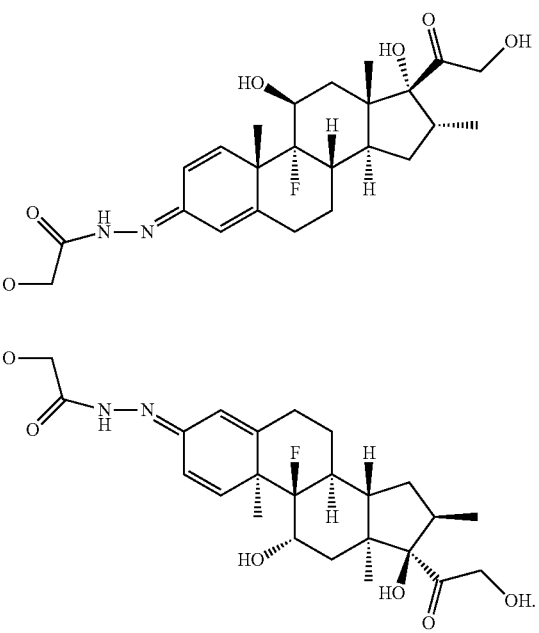
In some embodiments of this aspect, the compound has a structure of any one of formulas (VI)-(XI):
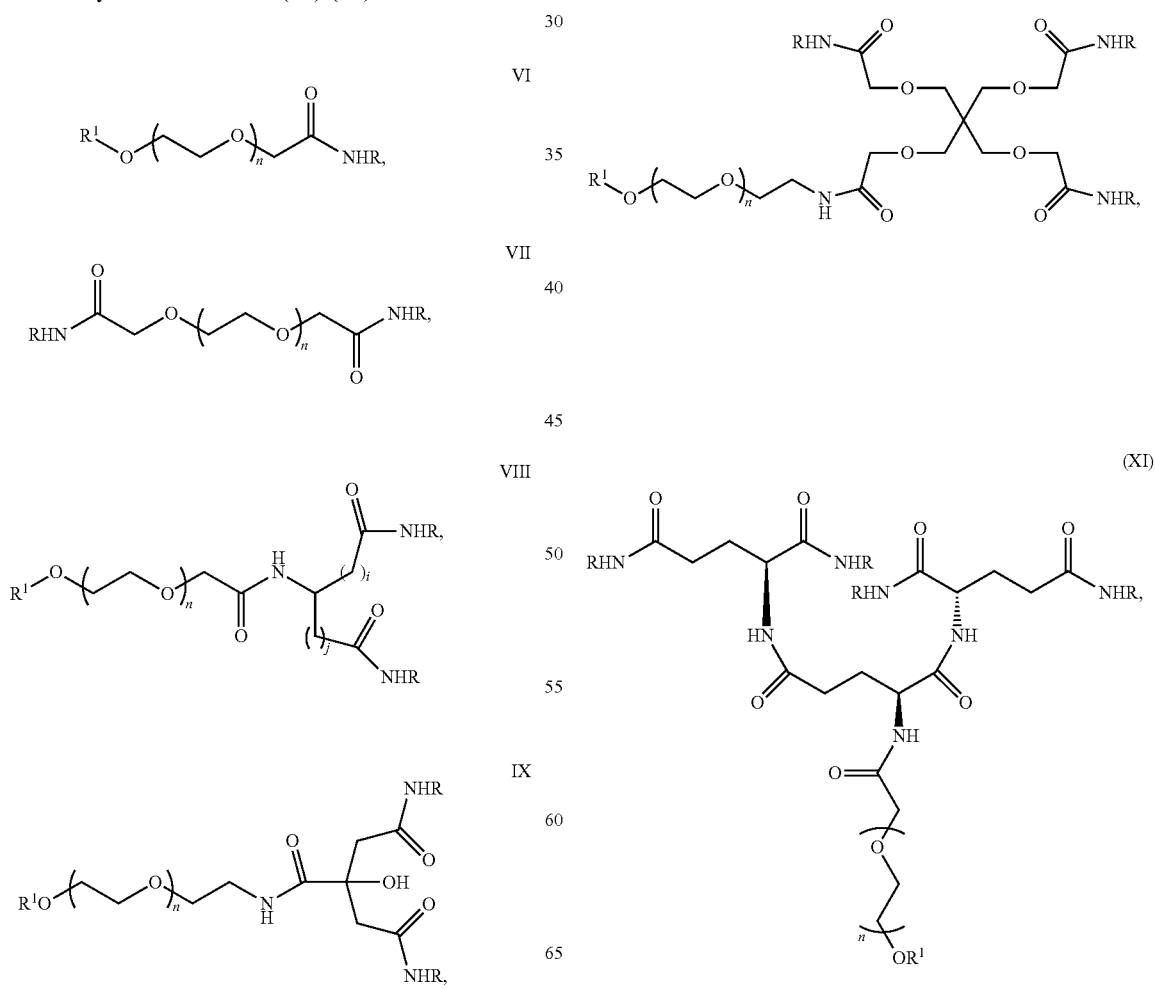

wherein R is selected from the group consisting of:
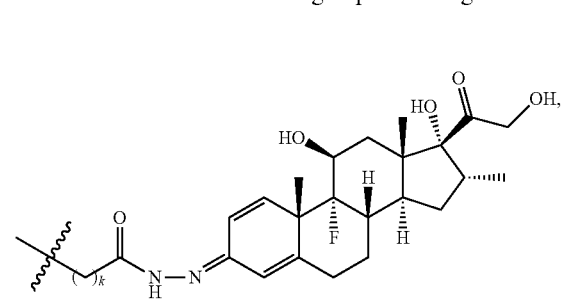
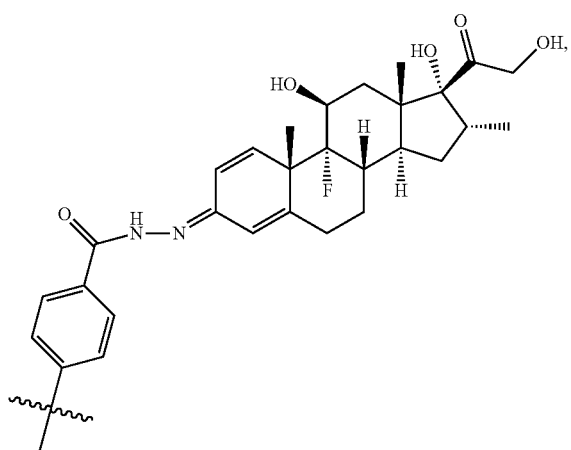
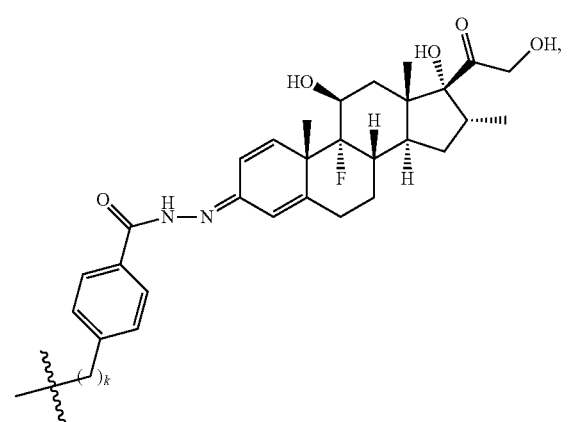
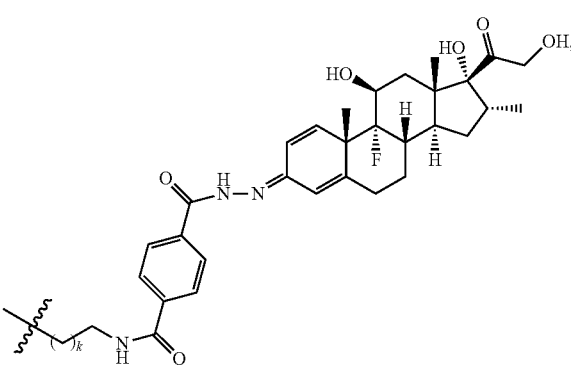
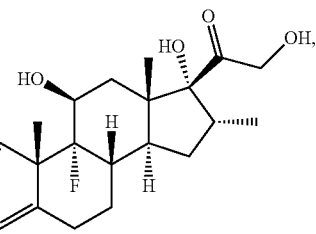
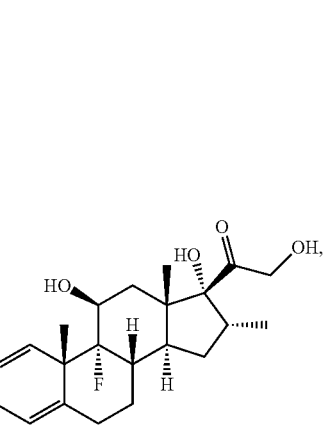
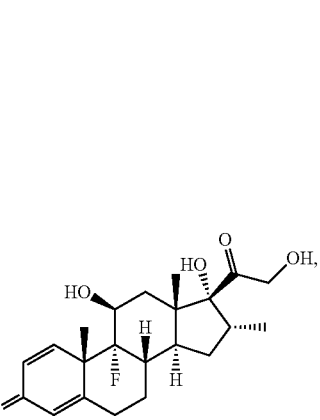
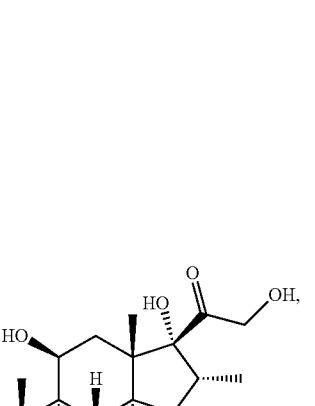
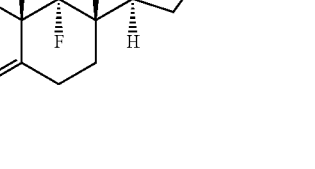

-continued

[three steroid structures shown with phenyl-N= linkers]

wherein k at each occurrence is independent an integer selected from 1 to 10. In some embodiments, k is an integer selected from 1 to 8; in some preferred embodiments, k is an integer selected from 1 to 6; and in some more preferred embodiments, k is an integer selected from 1 to 4; and in some more preferred embodiments, k is an integer selected from 1 to 2.

In some embodiments of this aspect, E is a glutamic acid based linker having a formula:

[glutamic acid-based linker structure]

glutamic acid-based

In another aspect, the present invention provides a compound of formula (XII):

$$R^1O-(\phantom{x}O\phantom{x})_n-A-B-D-E-(R^2)_m \quad (XII)$$

-continued $$R^2 = -Z-\left[Y-X-T-Q-P-G-N=\underset{GC}{\underset{\phantom{x}}{\bigcirc}}\right]_w,$$

or a pharmaceutically acceptable salt, solvate, or prodrug thereof, wherein:
n is an integer from 3 to 500;
m is an integer from 1 to 5;
w is an integer from 1 to 5;
GC is a moiety of a glucocorticoid drug molecule;
A is absent, $C_1$-$C_6$ alkylene, or $C_6$-$C_{10}$ arylene;
B is absent, $NR^4$, O, or C(O);
D is absent, $NR^4$, O, C(O), or $CR^5R^5$;
E is absent, $C_1$-$C_6$ alkylene, or a linker comprising a branched structure capable of connecting to two or more $R^2$ groups, said linker optionally comprising one, two, or more heteroatoms independently selected from the group consisting of O, S, and N;
G is absent, $NR^4$, or O;
P is absent or C(O);
Q is absent, $C_6$-$C_{10}$ arylene, or $C_1$-$C_6$ alkylene;
T is absent, $C_1$-$C_6$ alkylene, $C_6$-$C_{10}$ arylene, or C(O);
X is absent, O, S, or $NR^4$;
Y is absent, C(O), $C_6$-$C_{10}$ arylene, or $C_1$-$C_6$ alkylene;
Z is absent, $NR^4$, O, $C_1$-$C_6$ alkylene, or a linker comprising a branched structure capable of connecting to one or more dexamethasone moieties, said linker optionally comprising one or more heteroatoms independently selected from the group consisting of O, S, and N;
$R^1$ is H, $C_1$-$C_6$ alkyl, $C_2$-$C_6$ alkenyl, $C_2$-$C_6$ alkynyl, $C_6$-$C_{10}$ aryl, 5-10 membered heteroaryl, or 5-10 membered heterocyclyl, each group except H optionally substituted by one to five substituents independently selected from the group consisting of $C_1$-$C_4$ alkyl, $C_1$-$C_4$ haloalkyl, halogen, oxo (=O), $-NR^aR^b$, $-NO_2$, $-CN$, $-OR^3$, and $-SR^3$; or alternatively, $R^1$ is $-CH_2$-A-B-D-E-$(R^2)_m$;
$R^3$ at each occurrence is independently H, $C_1$-$C_4$ alkyl, or $C_1$-$C_4$ haloalkyl;
$R^4$ at each occurrence is independently H or $C_1$-$C_4$ alkyl;
$R^5$ at each occurrence is independently H, $C_1$-$C_4$ alkyl, or $C_1$-$C_4$ haloalkyl;
$R^a$ and $R^b$ are each independently H or $C_1$-$C_4$ alkyl; and
wherein when any of groups A, B, D, E, G, P, Q, T, X, Y, and Z is absent, its two available adjacent groups are single-bonded to each other directly.

In this aspect, the term "moiety of a glucocorticoid drug molecule" refers to the drug portion of the prodrug linked with PEG through various linkers through a C=N double bond as disclosed herein. In particular, these moieties of glucocorticoid drug molecules include, but are not limited to the following:

[Betamethasone structure]

Betamethasone

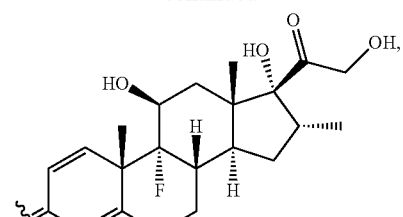
Dexamethasone
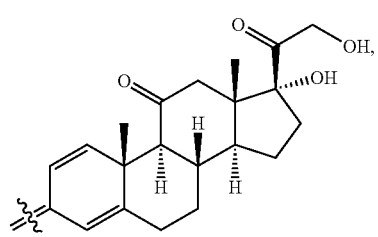
Prednisone
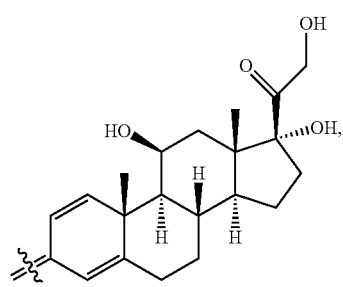
Prednisolone
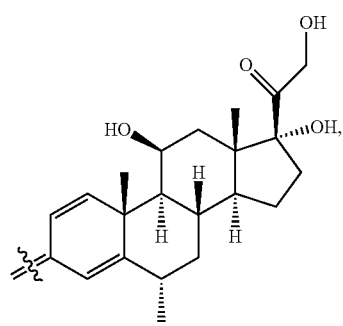
Methylprednisolone
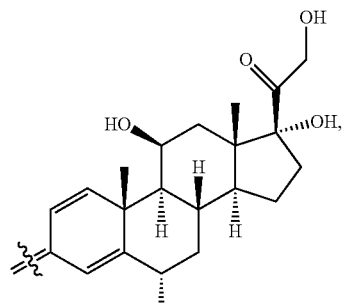
Methylprednisolone
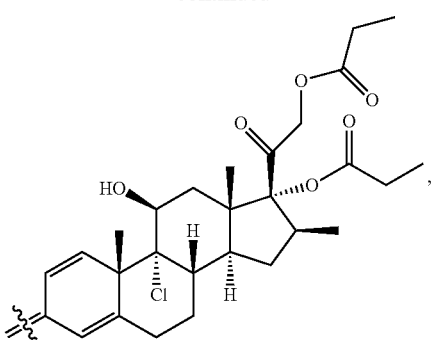
Beclometasone
or the like.
In some embodiments of this aspect, the compound a structure selected from formulae (XIII) to (XVIII):
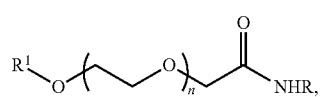
XIII
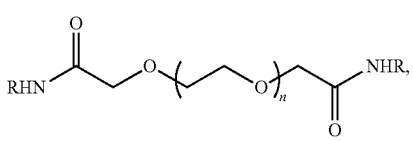
XIV
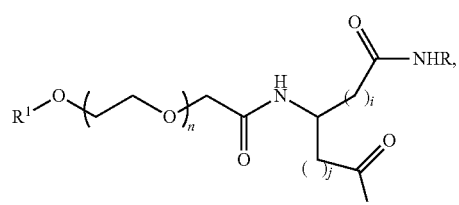
XV
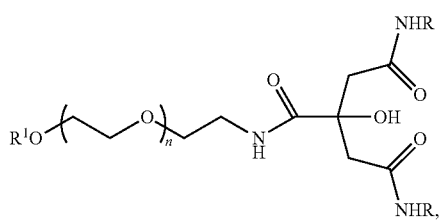
XVI
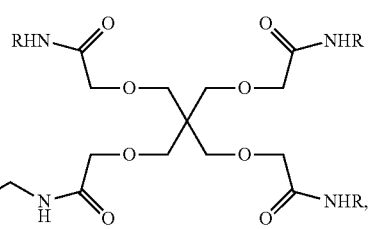
XVII -continued

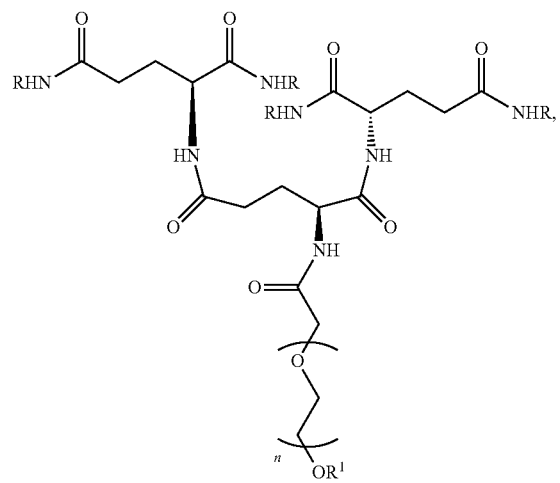

(XVIII)

wherein R comprises said moiety of a glucocorticoid drug molecule.

In some embodiments, the glucocorticoid drug molecule is selected from the group consisting of:

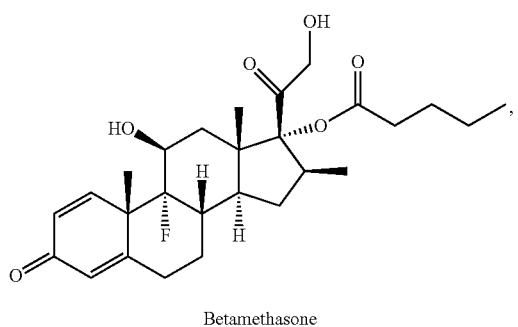

Betamethasone

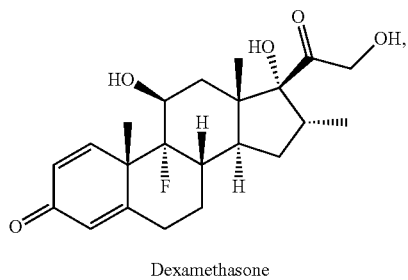

Dexamethasone

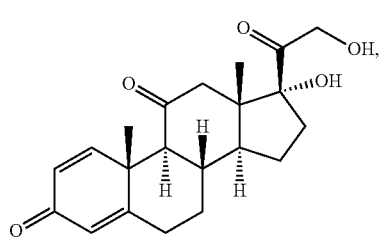

Prednisone

-continued

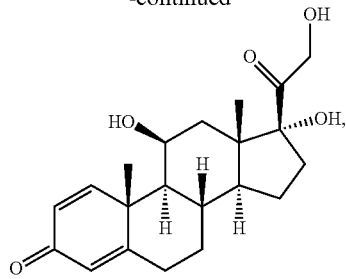

Prednisolone

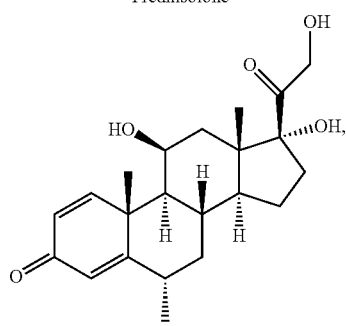

Methylprednisolone

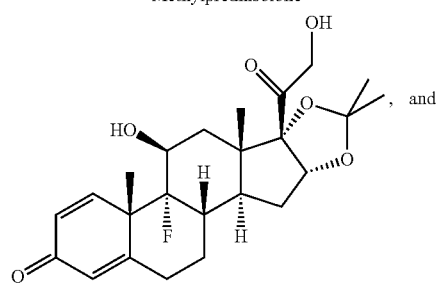

Triamcinolone

, and

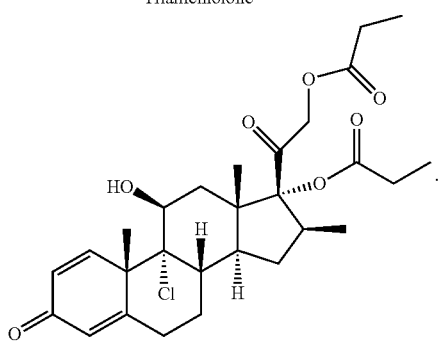

Beclometasone

The size of PEG suitable for compounds of the present invention can vary in a range so that the prodrug can serve the purpose disclosed herein. Typical size can be in the range of 100 to 20,000 Da. molecular weight, or n can be in the range of about 3 to about 500. In some embodiments, n is in the range of 10 to 300. In some embodiments of this aspect, n is 20 to 200. In some embodiments of this aspect, n is 10 to 100.

In some preferred embodiments of this aspect, n is 40-45; and in some particular embodiments, n is 42.

As a person of ordinary skill in the art would understand, in any aspects or embodiments of the compounds disclosed herein, any two adjacent atoms or bonds must comply with the basic bond principles. While basic bond principles are compliant with, any potential combination of the limitations defined in any two or more embodiments disclosed herein are encompassed by the present invention.

In another aspect, the present invention provides a pharmaceutical composition comprising a compound according to any one embodiment described herein, or a pharmaceutically acceptable salt, solvate, or prodrug thereof, and a pharmaceutically acceptable carrier, adjuvant, diluent, or vehicle.

In some embodiments of this aspect, the pharmaceutical composition is in oral, nasal, ophthalmic drop, topical, buccal, sublingual, rectal, vaginal, intravenous, or other parenteral form.

In some embodiments of this aspect, the pharmaceutical composition is in vaporization-ready, nebulization-ready, nanoparticle formulation, or liposomal formulation.

In some embodiments of this aspect, the composition of further comprises a second therapeutic agent, including but not limited, a NSAID (e.g. Aspirin, Naproxen, Celebrex), a Glucocorticoid (e.g. Dexamethasone, Prednisone, Betamethasone), a DMARD (e.g. Methotrexate, Leflunomide, Sulfasalazine, Hydroxychoroquine), or the like.

In another aspect, the present invention provides a method of treating an autoimmune disease and/or inflammatory disorder, comprising administering to a subject in need of treatment a therapeutically effective amount of a compound according to any embodiment disclosed here, or a pharmaceutically acceptable salt, solvate, or prodrug thereof.

In some embodiments of this aspect, the disease or disorder is systemic lupus erythematosus, lupus nephritis, minimal change disease, focal segmental glomerulosclerosis, IgA nephropathy, transplant rejection, rheumatoid arthritis, osteoarthritis, psoriasis, ankylosing spondylitis, vasculitis, multiple sclerosis, systemic sclerosis, gout, uveitis, asthma, cystic fibrosis, chronic obstructive pulmonary disease, atopic dermatitis (eczema), sepsis, inflammatory bowel disease, trauma brain injury, spinal cord injury, ischemia reperfusion injury, heterotopic ossification, or granuloma, etc.

In some embodiments of this aspect, the method of treating disease or disorder further includes administering to the subject a second therapeutic agent, such as a NSAID (e.g. Aspirin, Naproxen, Celebrex), a Glucocorticoid (e.g. Dexamethasone, Prednisone, Betamethasone), a DMARD (e.g. Methotrexate, Leflunomide, Sulfasalazine, Hydroxychoroquine), a biologic (e.g. Belimumab, Etanercept, Anakinra, Infliximab, Rituximab, etc.), or the like.

In another aspect, the present invention provides a method of treating a disease or disorder associated with lupus, comprising administering to a subject in need of treatment a therapeutically effective amount of the pharmaceutical composition of any embodiment disclosed herein.

In some embodiments of this aspect, the subject treated is a mammalian animal, such as human, dog, cat, horse, and so on. In a preferred embodiment, the subject is a human.

In another aspect, the present invention provides use of a compound according to any embodiment or any embodiment combinations disclosed here, or a pharmaceutically acceptable salt, solvate, or prodrug thereof, in the manufacture of a medicament for treatment of a disease or disorder, especially those associated with lupus.

The disease or disorder that can be treated using the present invention includes, but is not limited to, systemic lupus erythematosus, cutaneous lupus erythematosus, photosensitivity, cutaneous vascular disease, nonscarring alopecia, oral ulcer, nail and capillary changes, populonodular mucinosis, bullous lupus erythematosus, sweet syndrome, pyoderma gangrenosum, palisaded neutrophilic granulomatous dermatitis, aseptic meningitis, cerebrovascular disease, demyelinating syndrome, headache, movement disorder, myelopathy, seizure disorder, acute confusional state, anxiety disorder, cognitive dysfunction, mood disorder, psychosis, Guilain-Barré syndrome, autonomic neuropathy, mononeuropathy, myasthenia gravis, cranial neuropathy, plexopathy, polyneuropathy, lupus nephritis, pericarditis, coronary vasculitis, coronary atherosclerosis, vasculitis, pleurisy, pleural effusion, acute lupus pneumonitis, diffuse alveolar hemorrhage, chronic interstitial lung disease shrinking lung syndrome, pulmonary hypertension, thromboembolism, cricoarytenoid arthritis, small airways disease, chronic active and lupoid hepatitis, Sjögren's syndrome, esophagitis, watermelon stomach, eosinophilic gastroenteritis, abdominal pain, intestinal thrombosis, inflammatory bowel disease, protein-losing enteropathy, fat malabsorption, Celiac Sprune, Chronic intestinal pseudo-obstruction, amyloidosis, peritoneal inflammation, pancreatitis, splenomegaly, autoimmune hemolytic anemia, immune thrombocytopenic purpura, leukopenia, arthralgia, arthritis, tendon rupture, myositis, osteonecrosis, osteoporosis, etc.

Without being limited, in some embodiments, the molecular weight of PEG used in the present invention is in the range from about 200 to about 10,000 Da. The glucocorticoid (GC) drug molecule can be conjugated to a chain terminus, or both chain termini of PEG. In addition to linear PEG, branched PEG, brush like PEG or even dendritic PEG can also be used as the prodrug carrier for conjugation with molecules such as Dex. The number of drug molecule such as dexamethasone (Dex) can range from 1 to 10 in each molecule of PEG prodrug conjugate. To increase the micelle stability, the hydrophobic terminus may be crosslinked with weak chemical bonds.

In addition to dexamethasone, other glucocorticoids (e.g. prednisone, prednisolone, methylprednisolone, betamethasone, triamcinolone, beclometasone), anti-inflammatory agents, and low molecular weight immune suppressant can be used to conjugate to PEG according to the principle and methods disclosed herein.

Unless defined otherwise, all technical and scientific terms used herein have the same meanings as are commonly understood by one of ordinary skill in the art to which this invention pertains.

Unless otherwise specified, a reference to a particular compound includes all of its isomeric forms. For example, when a compound has a C=N—X moiety (X=NHR, OR, or R, wherein R is any suitable group, e.g., H, alkyl, aryl, or acyl, etc.), such as hydrazone (X=NHR), imine (X=R), or oxime (X=OR) derivatives, the X group can exist in syn-(E-) or anti-(Z-) configuration relative to the other portion of the molecule, in particular the groups on both sides of the C=N bond, as would be understood by a person or ordinary skill in the art. When a compound has multiple such C=N—X moieties, multiple isomers would be possible. In the present disclosure, all such isomers, in pure or mixture forms or any combinations thereof, are encompassed by the name or structure of such compounds, as would be understood by those of ordinary skill in the pertinent art, even though they are not explicitly called by names or shown in the structures presented. Unless otherwise specified, a reference to a particular compound also includes ionic, salt, solvate (e.g., hydrate), protected forms, and other stereoisomers thereof, for example, as discussed herein.

In the compounds disclosed herein, the atoms may exhibit their natural isotopic abundances, or one or more of the atoms may be artificially enriched in a particular isotope having the same atomic number, but an atomic mass or mass number different from the atomic mass or mass number predominantly found in nature. For example, substitution with heavier isotopes, such as replacing hydrogen (H) with deuterium (i.e., $^2$H or D) may afford certain therapeutic advantages resulting from greater metabolic stability (e.g., increased in vivo half-life or reduced dosage requirements) and hence may be preferred in some circumstances. In addition, certain isotopically-labeled compounds (e.g., with $^3$H and $^{14}$C) are useful in compound and/or substrate tissue distribution assays. Isotopically labeled compounds can generally be prepared by following procedures analogous to those disclosed in the Schemes and/or in the Examples below, by substituting an appropriate isotopically labeled reagent for a non-isotopically labeled reagent. The present invention is meant to include all suitable isotopic variations of the compounds disclosed.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

When the term "about" is applied to a number or parameter, the number or parameter can vary by ±10%, inclusive. As would be understood by a person skilled in the art, when a parameter is not critical, a number is often given only for illustration purpose, instead of being limiting.

The term "a," "an," or "the," as used herein, represents both singular and plural forms. In general, when either a singular or a plural form of a noun is used, it denotes both singular and plural forms of the noun.

The term "treating," "treatment," or "therapy," or the like, as used herein in the context of treating a disease or condition, pertains generally to treatment and therapy of an animal subject, preferably a human, in which some desired therapeutic effect is achieved. For example, therapy can include the inhibition of the progress of the condition, reduction in the rate of progress, a halt in the rate of progress, amelioration of the condition, absolute or partial prevention of a delayed complication, and cure of the condition. Treatment also includes prophylactic measure as well as adjunct treatments to a standard treatment regimen established in the art.

The term "therapeutically effective amount," as used herein, pertains to that amount of an active compound, or a material, composition or dosage form comprising an active compound, which is effective for producing some desired therapeutic effect, commensurate with a reasonable benefit/risk ratio.

It may be convenient or desirable to prepare, purify, and/or handle the active compound in the form of a prodrug. The term "prodrug" as used herein, pertains to a compound which, when metabolized, yields the desired active compound or in itself is the active compound. Typically, the prodrug is inactive, or less active than the active compound, but may provide advantageous handling, administration, or metabolic properties. For example, some prodrugs are ethers or esters of the active compound; during metabolism the ether group is cleaved to yield the active drug. Also, some prodrugs are activated enzymatically to yield the active compound, or a compound which, upon further chemical reaction, yields the active compound. Thus, in the methods of treatment of the present invention disclosed herein, the term "administering" shall encompass the treatment of the various conditions described with the compound specifically disclosed or with a compound which may not be specifically disclosed, but which converts to the specified compound in vivo after administration to the patient. Metabolites of these compounds include active species produced upon introduction of compounds of this invention into the mammalian subject.

Any of the compounds of the present invention may be contemplated for administration to the human subject in the form of a drug, prodrug or even active metabolite.

In particular, although the compounds disclosed herein are prodrugs themselves relative to the parent drug compound, e.g., glucocorticoids (e.g. dexamethasone, prednisone, etc.), these compounds themselves may exist in their prodrug forms. For example, any of the hydroxyl or amino groups on the molecule may be protected by an acyl (e.g., acetyl) or other group that can be readily hydrolyzed under the physiological conditions to become the parent polyethylene glycol-glucocorticoid (PEG-GC) drug compound. Such additional level of prodrug may even be preferred under certain circumstances to further control the release mode and rate of the parent drug compound in a subject.

As noted herein, the salts of the compounds of this invention refer to non-toxic "pharmaceutically acceptable salts." Other salts may, however, be useful in the preparation of the compounds according to the invention or of their pharmaceutically acceptable salts. When the compounds of the present invention contain a basic group, salts encompassed within the term "pharmaceutically acceptable salts" refer to non-toxic salts which are generally prepared by reacting the free base with a suitable organic or inorganic acid. Representative salts include any such salt known in the art. Where compounds of the present invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

To treat a human patient, an effective amount of one or more compounds of the present invention, or a pharmaceutically-acceptable salt thereof, is administered to the human subject in need so as to promote exposure to or contact of the tissue at risk or the targeted region of the body or nerves, synapses, or neuromuscular junctions, or organ systems including but not limited to the autonomic and central nervous systems. Effective dosage forms, modes of administration and dosage amounts may be determined empirically, and making such determinations is within the skill of the art.

As discussed herein, the PEG-GC drug compounds disclosed herein can be administered in such oral dosage forms as tablets, capsules (each of which includes sustained release or timed release formulations), pills, powders (e.g., reconstitutable lyophilized powder), micronized compositions, granules, elixirs, tinctures, suspensions, ointments, vapors, liposomal particles, nanoparticles, syrups and emulsions. Likewise, they may also be administered in intravenous (bolus or infusion), intraperitoneal, topical (e.g., dermal, epidermal, transdermal, ophthalmically such as ocular eyedrop), intranasally, subcutaneous, inhalation, intramuscular or transdermal (e.g., patch, microneedles) form, all using forms well known to those of ordinary skill in the pharmaceutical arts. Again, the ordinarily skilled physician, veterinarian or clinician or a clinical pharmacist may readily determine and prescribe the effective amount of the drug required to prevent, counter or arrest the progress of the condition.

As noted herein, the compounds of the present invention may be used in combination with other drugs or therapies having similar or complementary effects to those of the compounds disclosed herein. The individual components of such combinations can be administered separately at different times during the course of therapy or concurrently in divided or single combination forms to patients or regions of such patients in need of such therapy. The instant invention is therefore to be understood as embracing all such regimes of simultaneous or alternating treatment and the term "administering" is to be interpreted accordingly.

As used herein, the term "composition," "pharmaceutical composition," or the like, is intended to encompass a product comprising the specified ingredients in the specified amounts, as well as any product which results, directly or indirectly, from combination of the specified ingredients in the specified amounts.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Pharmaceutical formulations of the present invention include those suitable for oral, nasal, topical (including buccal and sublingual), rectal, vaginal and/or parenteral administration. Formulations of the invention suitable for oral administration may be in the form of capsules, cachets, pills, tablets, lozenges (using a flavored basis, usually sucrose and acacia or tragacanth), powders (e.g., reconstitutable lyophilized powder), granules, or as a solution or a suspension in an aqueous or nonaqueous liquid, or as an oil-in-water or water-in-oil liquid emulsion, or as an elixir or syrup or tincture, or as pastilles (using an inert base, such as gelatin and glycerin, or sucrose and acacia) and the like, each containing a predetermined amount of the active ingredient(s). The active ingredient(s) may also be administered as a bolus, electuary or paste.

The formulations may be presented in unit-dose or multi-dose sealed containers, for example, ampoules and vials, or in specialized capsules for vapor or nebulized administration and may be stored in a lyophilized condition requiring only the addition of the sterile liquid carrier, for example water or oil for injection, immediately prior to use. Extemporaneous injection solutions and suspensions maybe prepared from sterile powders, granules and tablets of the type described above.

PEG-DiDex is an amphiphilic macromolecular prodrug with a Dex dimer constitutes the hydrophobic section. A mPEG 1900 was employed as the hydrophilic section. The utility of this short PEG as the carrier will not only reduce WBC internalization but also significantly reduce the serum half-life of the prodrug, which may greatly limit the prodrug's distribution to the mononuclear phagocyte system (MPS). Due to the use of PEG as the drug carrier, PEG-DiDex activation is slow (FIG. 3), which may be helpful in maintaining a low serum concentration of free Dex. The amphiphilic design would allow the prodrug to self-assemble into micelles (FIG. 1 and FIG. 2) so that it would not be cleared through kidney too fast and overwhelm the renal cell sequestration capacity. The synthesis of PEG-DiDex is straightforward with high yield at each step. Due to the use of hydrazone linker as the prodrug activation trigger, PEG-DiDex will have multiple syn/anti-hydrazone isomers, which makes the interpretation of the NMR spectrum difficult. To minimize formation of multiple isomers, in some embodiments symmetric branching structures such as citric acid may be used instead of glutamic acid. Furthermore, to minimize formation of prodrug with polydisperse molecular weight due to the use of conventional PEG, in some embodiments, it may be preferable to use single molecular weight discrete PEG (dPEG®), which has become commercially available. Different from traditional polymeric prodrug design, the use of dPEG® in the synthesis of PEG-DiDex will yield a product with a single molecular weight, which will remove potential regulatory hurdles during the product development process.

Figures 4A, 4B:
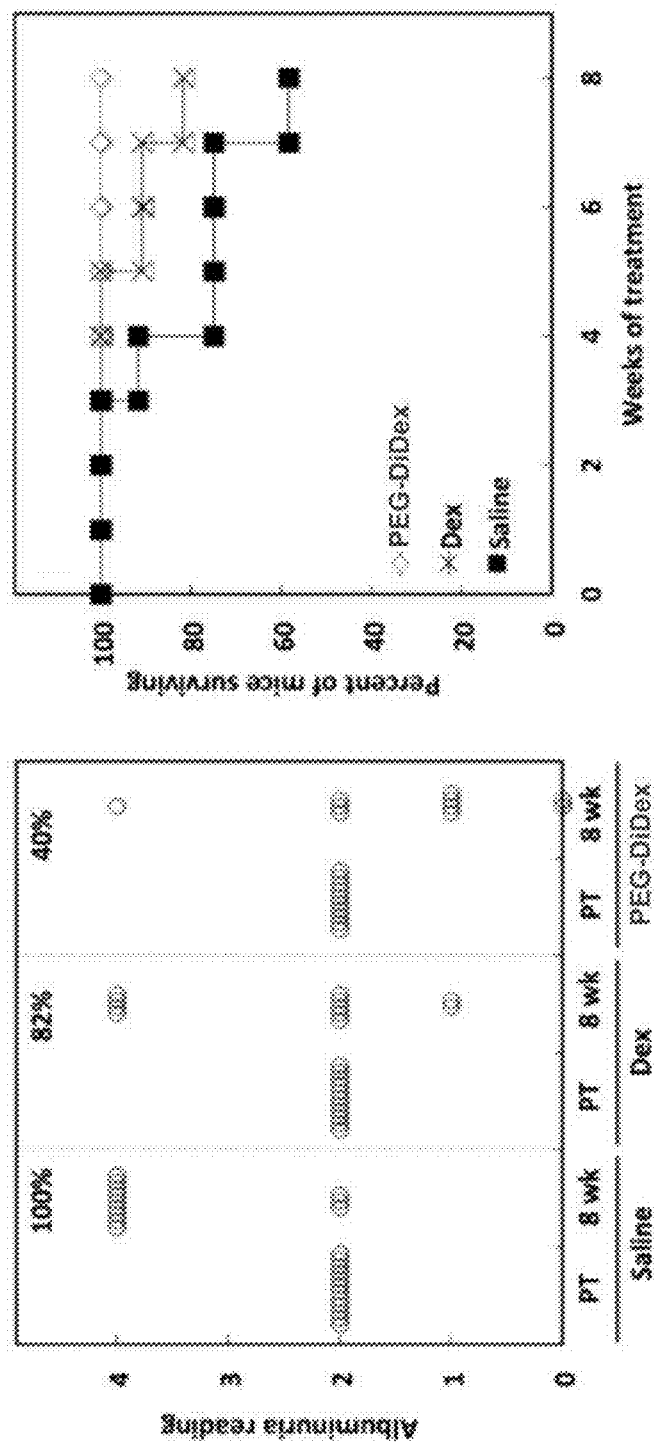
FIGS. 4A and 4B illustrate monthly PEG-DiDex treatment results, which demonstrate superior therapeutic effect when compared to dose equivalent daily Dex treatment of 28 wks old NZB/W F1 female mice with severe nephritis. (A) Monthly PEG-DiDex treatment normalized albuminuria among 60% of NZB/W F1 mice, while dose equivalent daily Dex treatment only normalized 18% at the end of 2-months treatment. PT=pretreatment. (B) Kaplan-Meier survival curves for PEG-DiDex, Dex and saline treatment groups are shown. Only PEG-DiDex treatment results in 100% survival after 2-month treatment.
Figures 5A, 5B, 5C, 5D, 5E, 5F:
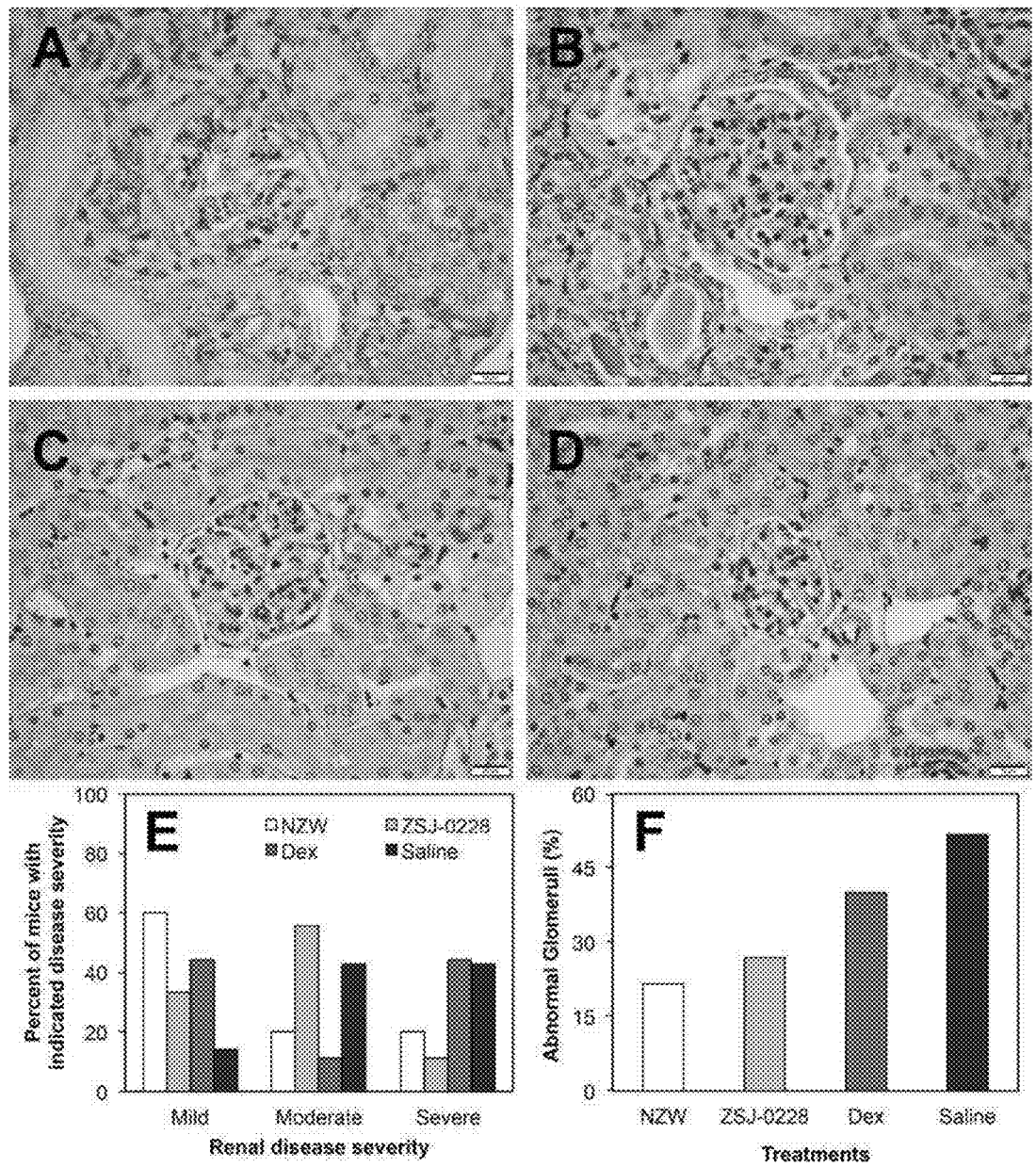
FIGS. 5A, 5B, 5C, 5D, 5E, and 5F illustrate histological evaluation of kidneys isolated at the 2-month treatment end points. The tissues were formalin-fixed, sectioned (3 μm) and periodic-acid schiff (PAS) stained for visual examination and 4 point grading by a pathologist, who is blind to the group design. (A) PAS-stained kidney section from saline group. Bar=20 μm; (B) PAS-stained kidney section from Dex group. Bar=20 μm; (C) PAS-stained kidney section from PEG-DiDex group. Bar=20 μm; (D) PAS-stained kidney section from NZW control group. Bar=20 μm; (E) The fraction of mice in each group with mild, moderate and severe renal disease is shown; (F) The percentage of abnormal glomeruli found in each group is shown.

Treatment of NZB/W F1 mice with severe nephritis with PEG-DiDex monthly effectively attenuated albuminuria and maintained 100% animal survival for the entire experiment duration. On the other hand, dose equivalent daily Dex treatment only presented with moderate efficacy and 80% survival (FIG. 4). These observations were further supported with kidney histology finding, in which the PEG-DiDex treated mice were found with mainly mild/moderate nephritis and more normal glomeruli than Dex and saline groups (FIG. 5). It is worth noting of an extraordinary finding during the histological evaluation: signs of severe nephritis were found in kidney sections from a NZW control mouse. NZB/W F1 is the offspring of an NZB/BINJ (Jackson Laboratory) female and an NZW/LacJ (Jackson Laboratory) male. Both inbred parental strains develop certain autoimmune abnormalities that are observed in the F1, but not necessarily with similar onset or severity. The NZW/LacJ mice have a normal life span but do develop anti-dsDNA antibodies, high serum levels of retroviral gp70 antigen, and nephritis later in life. Therefore, we attribute this isolated finding to the advanced age of the animal (38 weeks).

Figure 6:
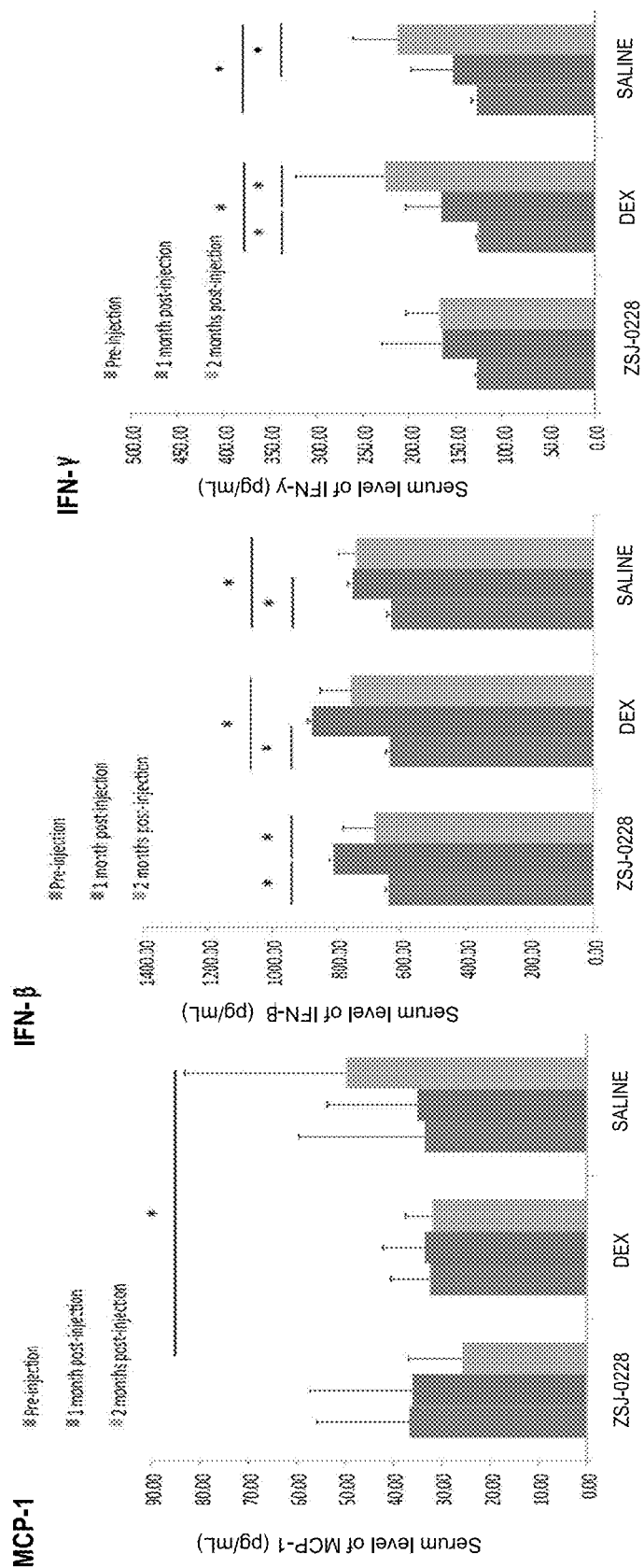
FIG. 6 illustrates treatment with PEG-DiDex, which attenuates serum inflammatory cytokines.

Additional therapeutic benefit of PEG-DiDex treatment was also found in its capacity to more effectively attenuate systemic proinflammatory cytokine/chemokine levels than Dex treatment (FIG. 6).

This effective regulation of systemic proinflammatory cytokine/chemokine may also explain the better-persevered bone quality in mice treated with PEG-DiDex (FIG. 7) than both Dex and saline groups, as severe systemic inflammation is known to be detrimental to the skeletal quality. Comparing to dose equivalent daily Dex treatment, the monthly PEG-DiDex treatment did not induce immune suppression as evident by WBC and total serum IgG levels comparable to the saline group. Furthermore, mice treated monthly with PEG-DiDex were found with significantly higher adrenal gland mass than the dose equivalent daily Dex treated mice. Collectively, these data provide solid evidence of PEG-DiDex's superior safety profile to those of Dex.

PEG-DiDex also compares favorably with the N-(2-hydroxypropyl)-methacrylamide (HPMA) copolymer-based Dex prodrug (the "P-Dex") disclosed previously (see, e.g., WO 2005/097073A1, CN 101518654A, and CN 103059220A) on adverse effects. First, PEG-DiDex is a prodrug amphiphile that can self-assemble into micelles with the drug conjugated to chain terminus. The micelles disintegrate into monomers upon dilution in the circulation; whereas in P-Dex, the drug is conjugated to a polymer side chain. P-Dex does not form micelles and cannot disintegrate. Second, because of the use of relatively short PEG (~2000 Da), PEG-DiDex is predicted to have a much shorter serum half-life than P-Dex, which constitutes its kidney targeting capacity and extremely low systemic toxicity as supported by the toxicity data. Third, the imaging results have shown that PEG-DiDex targets exclusively nephritis, whereas P-Dex has high accumulation in liver and spleen in addition to kidney. Moreover, when dPEG (a commercially available PEG with a single molecular weight) is used, the PEG-DiDex should behave like a small-molecule or biologic drug with a single molecular weight, without the polydispersity that polymer drug conjugates typically have. In addition, when Dex is conjugated to a multifunctional PEG carrier via a hydrazone bond, the prodrug activation rate is slower than P-Dex. Therefore, by design the PEG-Dex hereby disclosed greatly reduces serum free Dex concentration by limiting the prodrug's sequestration by WBC and its deposition in the liver and spleen; whereas the decreased molecular weight and serum half-life of P-Dex would lead to lower liver and spleen distribution.

Optical imaging-based in vivo biodistribution data (FIG. 8) indicate PEG-DiDex's dominant and sustained distribution organ in NZB/W F1 mice is the inflamed kidney. The distribution to other organs was very limited, which is in stark comparison to the observation in mice treated with P-Dex (with high liver and spleen deposition, data not shown). This result was further supported by PEG-DiDex's inability to reduce systemic anti-dsDNA level (FIG. 9) and to resolve splenomegaly (data not shown). These findings collectively suggest that the outstanding safety profile of PEG-DiDex may be attributed to its nephritis-oriented distribution pattern. In NZW control mice, PEG-DiDex's nephrotropic distribution pattern was repeated, but with the tissue prodrug concentration at a much lower level. It indicates that the kidney retention of PEG-DiDex is inflammation selective.

Immunohistological and flow cytometry analyses revealed that Alexa Fluor 488-labeled PEG-DiDex was mainly sequestered by CD11-b$^+$ (monocytes), F4/80$^+$ (macrophages), CD146$^+$ (endothelial cells) and CD326$^+$ (epithelial cells) in the kidneys of NZB/W F1 mice. After 8 weeks of treatment, the kidney of PEG-DiDex treated NZB/W F1 mice showed a significantly lower monocyte/macrophage population and local inflammatory cytokine level than dose equivalent Dex treated animals, suggesting the much effective and sustained local anti-inflammatory effect of PEG-DiDex. The prodrug's internalization, subcellular activation and inflammation resolution were further validated with in vitro cell culture systems.

In summary, the present invention provides a novel micelle-forming PEG-based dexamethasone prodrug (PEG-DiDex) with superior and sustained efficacy against lupus nephritis, but without typical glucocorticoid side effects. While it is hardly perceivable that the Dex released from PEG-DiDex would attenuate inflammation via a different molecular mechanism, this newly developed prodrug indeed altered the Dex's pharmacology on the physiology level by restricting the Dex's distribution to the inflamed kidney and providing a sustained local concentration of Dex via the gradual activation of PEG-DiDex within the endosomal/lysosomal compartments. Given its outstanding therapeutic efficacy and safety profile, PEG-DiDex can provide better clinical management of lupus nephritis. Moreover, the novel glucocorticoid prodrugs may also find wider applications in other renal pathologies, such as minimal change disease, IgA nephropathy, focal segmental glomerulosclerosis, and kidney transplant, since glucocorticoids are commonly used in managing these conditions as well.

The following non-limiting Examples further illustrate certain aspects of the present invention.

EXAMPLES

Synthesis and Characterization of PEG-DiDex

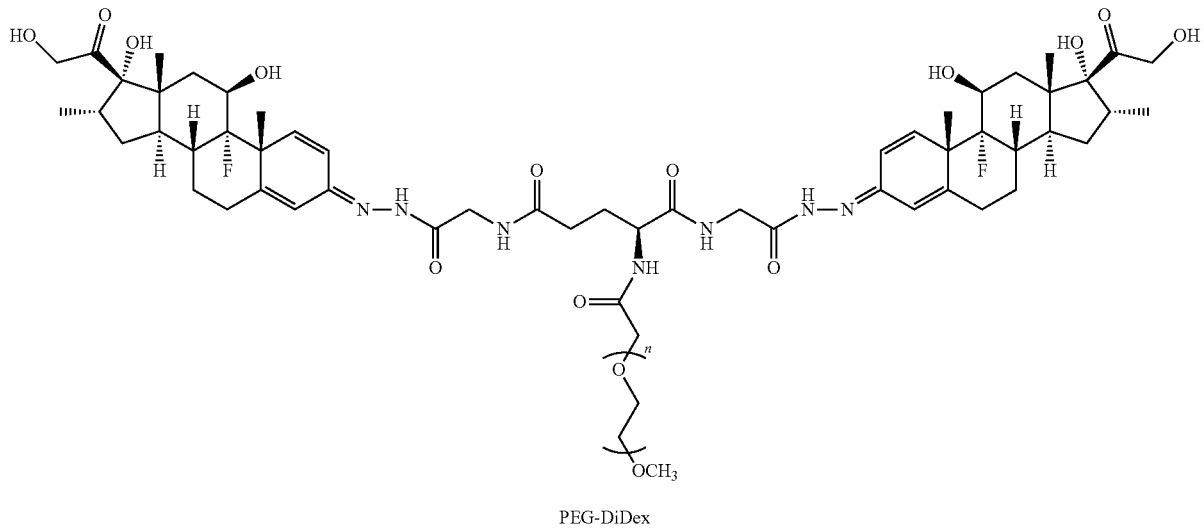

PEG-DiDex

Materials

Polyethylene glycol monomethyl ether 1900 (mPEG, 1.9 kDa) and N-Fmoc-L-glutamic acid were purchased from Alfa Aesar (MA, USA). Dexamethasone (Dex) was obtained from Tianjin Pharmaceuticals Group Co., Ltd. (Tianjin, China). Dexamethasone phosphate was purchased from Hawkins, Inc. (Minneapolis, Minn., USA). Dexamethasone phosphate disodium was purchased from BUFA (The Netherlands). Peperidine was purchased from Sigma-Aldrich (St. Louis, Mo., USA). Dess-Martin periodinane was obtained from Oakwood Products, Inc. (Estill, S.C., USA). IRDye 800CW NHS ester was purchased from LI-COR Biosciences (Lincoln, Nebr., USA). Alexa Fluor 488 NHS ester was obtained from Life Technologies (Carlsbad, Calif., USA). Sephadex LH-20 resins were purchased from GE HealthCare (Piscataway, N.J., USA). All solvents and other reagents if not specified were purchased from Fisher Scientific or ACROS and used without further purification.

Instruments $^1$H and $^{13}$C NMR spectra were recorded on a 500 MHz NMR spectrometer (Varian, Palo Alto, Calif., USA). Electrospray ionization mass spectrometry was performed on a LCQ Classic Mass Spectrometer (Finnigan MAT, San Jose, Calif., USA). HPLC analyses were done on an Agilent 1100 HPLC system (Agilent Technologies, Inc., Santa Clara, Calif., USA) with a reverse phase C18 column (Agilent, ZORBAX 300SB-C18, 4.6×250 mm, 5 am). In vivo near-infrared fluorescence (NIRF)-based optical imaging was accomplished on a LI-COR Pearl™ Impulse Small Animal Imaging System (Lincoln, Nebr., USA). Bone qualities were analyzed using a high-resolution micro-CT system (Skyscan 1172, Skyscan, Aartselaar, Belgium). The average hydrodynamic diameter, polydispersity index (PDI) and zeta potential of micelles were determined by dynamic light scattering (DLS) experiments using a Zetasizer Nano ZS90 (Malvern Instruments, Worcestershire, UK). The micelles morphology was observed using a Tecnai G2 Spirit transmission electron microscope (TEM) (FEI, Hillsboro, Oreg., USA) at an acceleration voltage of 80 kV. Digital images were acquired using a KeenView high-resolution camera and analyzed using Soft Imaging Solutions AnalySIS ITEM digital software. The quantification of fluorescence signal intensities of IRDye 800 CW, Alexa Fluor 488 and pyrene were measured using Spectramax M2 spectrofluorometer (Molecular Devices, Sunnyvale, Calif.). The flow cytometry analyses were performed using a FACSCalibur flow cytometer (BD Biosciences). A Waters e2695 system equipped with a Waters 2489 absorption detector and a Waters Qtof Micro electrospray ionization mass spectrometer was used to perform high perfor-mance liquid chromatography/mass spectrometry analyses.

The Synthesis of Amphiphilic Macromolecular Dexamethasone Prodrug (PEG-DiDex)

PEG-DiDex, a polyethylene glycol (PEG)-based amphiphilic dexamethasone prodrug, was successfully synthesized according to the route illustrated in Scheme 1. The identity of the polymeric prodrug and the absence of free Dex were confirmed using LC-MS/MS. The multi-step synthesis is straightforward with high yield at each step. Due to the utility of hydrazone as the prodrug activation trigger that links Dex to glutamic acid and the overall dimer design, at least 4 syn/anti hydrazone configure isomers can be formed. These isomers of the Dex dimer (compound 6) were chromatographically separated using LC-MS/MS with chromatography conditions stated in the Instruments section. Mass spectra (positive ion ESI) for these isomers showed the molecular ion [M+H]$^+$ at 1066.7, which confirms their monoisotopic mass of 1065.7. The theoretical Dex content in PEG-DiDex is calculated as 26.7 wt %. After complete hydrolysis of the prodrug, the HPLC analysis showed that 26.4 wt % of the prodrug was released in the form of intact dexamethasone, suggesting the PEG-DiDex prodrug micelle synthesized has a~99% purity.

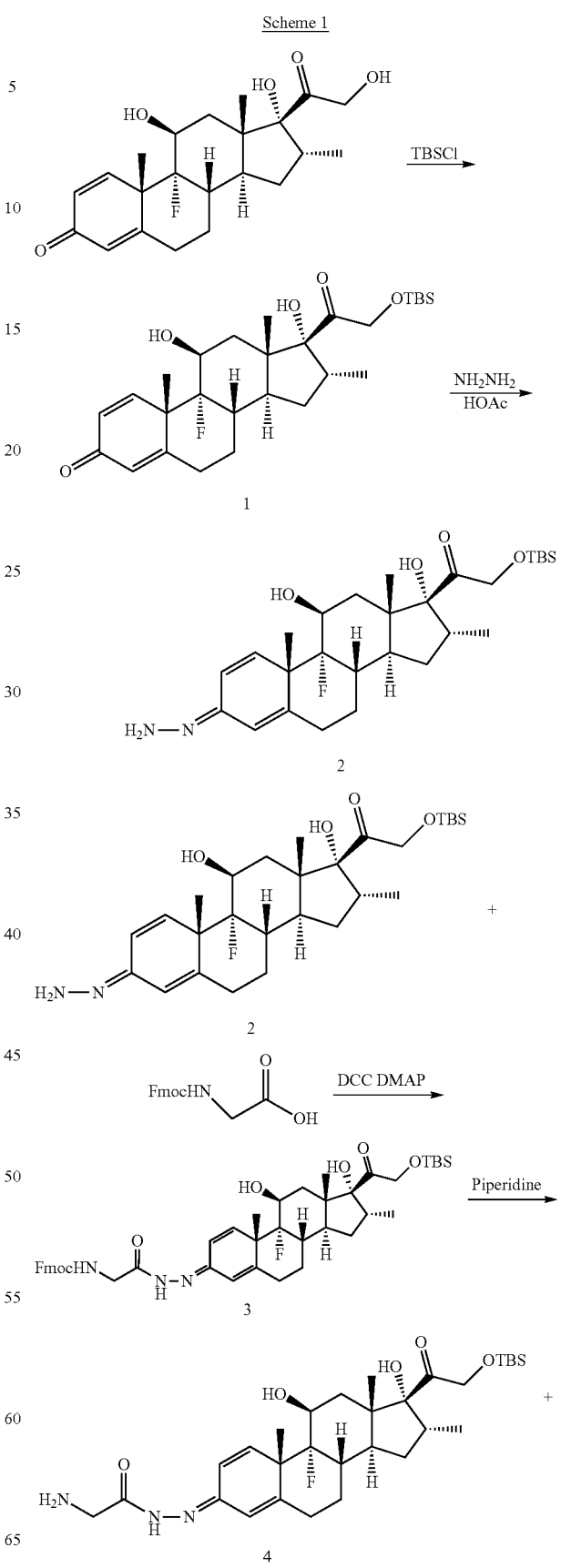

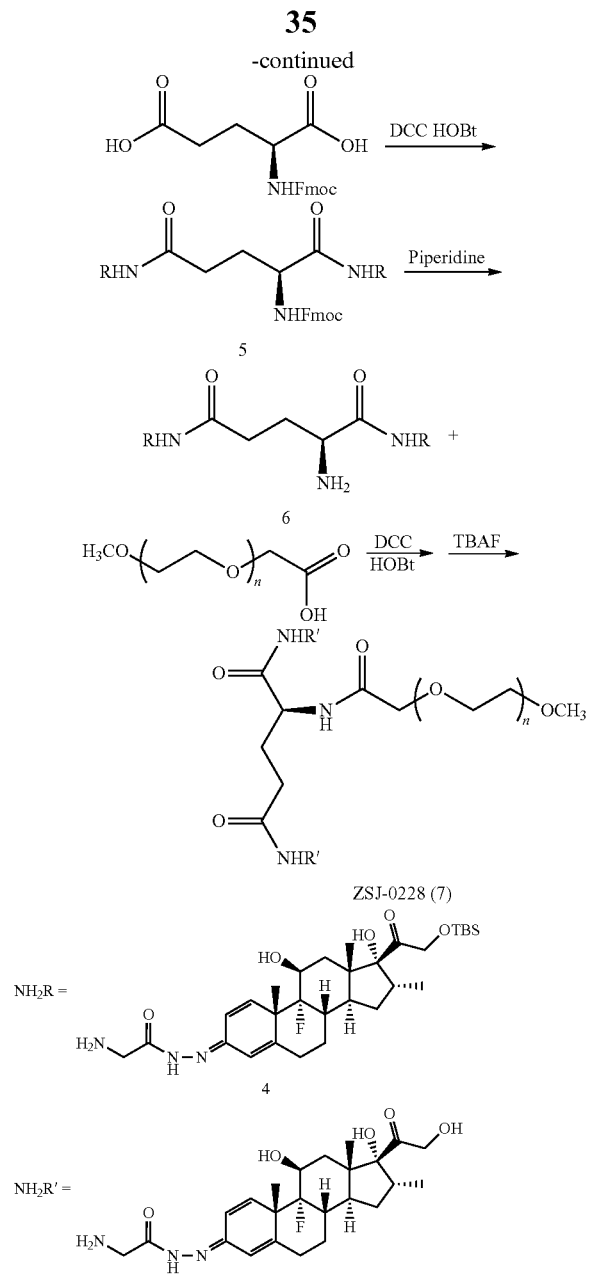

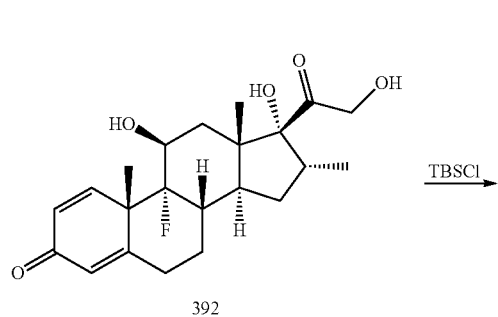

As shown in Scheme 1, the prodrug was synthesized by conjugating a Dex dimer to polyethylene glycol (PEG) 2000 chain terminus via a glutamate/glycine/hydrazone linker system.

Synthesis of Compound 1:

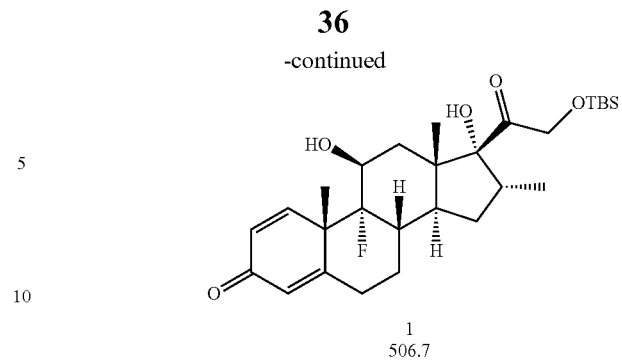

Dexamethasone (7.84 g, 20 mmol) and imidazole (2.72 g, 40 mmol) were dissolved in anhydrous DMF (40 mL) and the solution was cooled to 0° C. tert-butylmethylsilyl chloride (TBSC1, 3.3 g, 22 mmol) was added. The solution was stirred at 0° C. for 3 hours and then allowed to room temperature for 2 hours. Ethyl acetate (100 mL) was added and washed with brine (80 mL×4). The organic phase was dried over MgSO$_4$ and then the solvent was removed. The residue was purified with flash chromatography (ethyl acetate/hexanes=1/2) to give 9.98 g of compound 1 (98.5% yield).

$^1$H NMR (500 MHz, CDCl$_3$): δ (ppm)=7.26 (d, J=10.0, 1H), 6.32 (d, J=10.0, 6.10 (s, 1H), 4.63 (d, J=18.0, 1H), 4.38 (d, J=18.0, 1H), 4.37 (m, 1H), 3.23 (s, 1H), 3.05 (m, 1H), 2.62 (td, J=13.5, 6.0, 1H), 2.51 (s, 1H), 2.38 (m, 3H), 2.22 (m, 1H), 1.82 (m, 1H), 1.75 (m, J=7.0, 1H), 1.56 (m, 1H), 1.55 (s, 3H), 1.45 (d, J=13.5, 1H), 1.24 (m, 1H), 1.06 (s, 3H), 0.92 (s, 9H), 0.91 (d, J=7.0, 3H), 0.103 (s, 3H), 0.098 (s, 3H).

$^{13}$C NMR (125 MHz, CDCl$_3$): δ (ppm)=209.474, 186.768, 166.725, 152.226, 129.617, 124.904, 91.147, 72.159, 71.853, 69.462, 48.503, 43.635, 37.164, 36.146, 34.240, 34.084, 32.289, 31.045, 27.296, 25.814, 22.931, 22.886, 18.442, 17.168, 14.810, −5.328, −5.4662.

Synthesis of Compound 2:

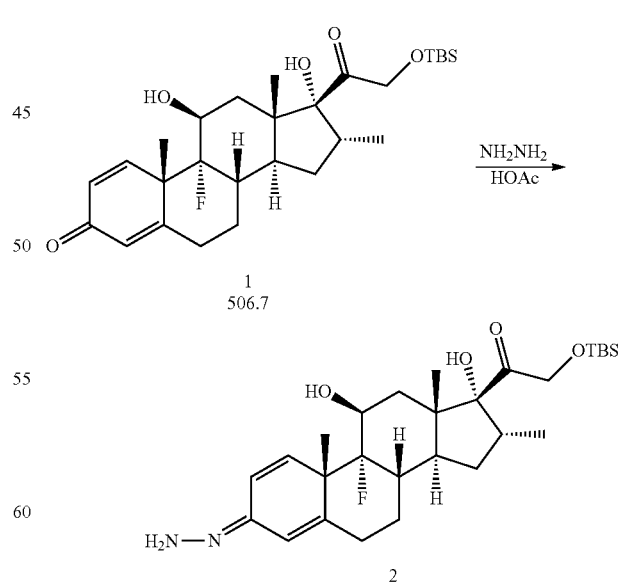

The starting material 1 (2.53 g, 5 mmol) and NH$_2$NH$_2$ monohydrate (750 mg, 15 mmol) were dissolved in methanol (25 mL). Acetic acid (60 mg, 1 mmol) was added and the solution was stirred at room temperature for 5 hours. Ethyl acetate (100 mL) was added and washed with brine (80 ml×4). The organic phase was dried over MgSO₄ and then the solvent was removed. The residue was purified with flash chromatography (ethyl acetate/hexanes=1/1) to give 1.14 g of compound 2. A total of 1.24 g starting material was recovered. The final yield was calculated as 85.8%. Due to the formation of hydrazone bond, the product is a mixture of two syn/anti hydrazone configure isomers, which can't be separated by flash chromatography. NMR analysis suggests the molar ratio of the two isomers is 1.75:1.

$^1$H NMR (500 MHz, d$_6$-DMSO): δ (ppm)=6.66 (dd, J=10.2 Hz, 1.5 Hz,), 6.34 (s, J=10.2 Hz, 6.28 (dd, J=10.2 Hz, 1.9 Hz), 6.14 (d, J=10.2 Hz), 5.99 (s), 5.24 (br, s), 4.61 (d, J=18.0 Hz), 4.59 (d, J=18.0 Hz), 4.38 (d, J=18.0 Hz), 4.36 (m), 3.05 (m, 1H), 3.03 (s), 2.97 (t, J=4.8 Hz), 2.62 (td, J=13.5, 5.8 Hz), 2.51 (td, J=13.5, 5.8 Hz), 2.40-2.20 (m), 1.70-1.60 (m), 1.55-1.50 (m), 1.476 (s), 1.472 (s), 1.40 (s), 1.37 (s), 1.24-1.20 (m), 1.04 (s), 0.92 (s), 0.90 (d, J=7.3 Hz), 0.103 (s). MS (ESI): m/z=521.5 (M+H+), calculated: 520.3.

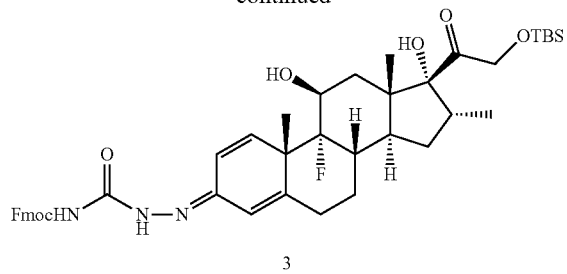

Compound 2 (2.86 g, 5.5 mmol), dimethylaminopyridine (DMAP, 201 mg, 1.65 mmol) were dissolved in anhydrous DMF (15 mL) and the solution was cooled to 0° C. Then Fmoc-glycine (2.12 g, 7.15 mmol), dicyclohexylcarbodiimide (DCC, 1.70 g, 8.25 mmol) were added to the solution. The solution was stirred at 0° C. for 3 hours. Ethyl acetate (100 mL) was added and washed with brine (80 mL×4). The organic phase was dried over MgSO₄ and then the solvent was removed. The residue was purified with flash chromatography (ethyl acetate/hexanes=1:1) to give 3.72 g of compound 3 (84.5% yield).

Synthesis of Compound 4:

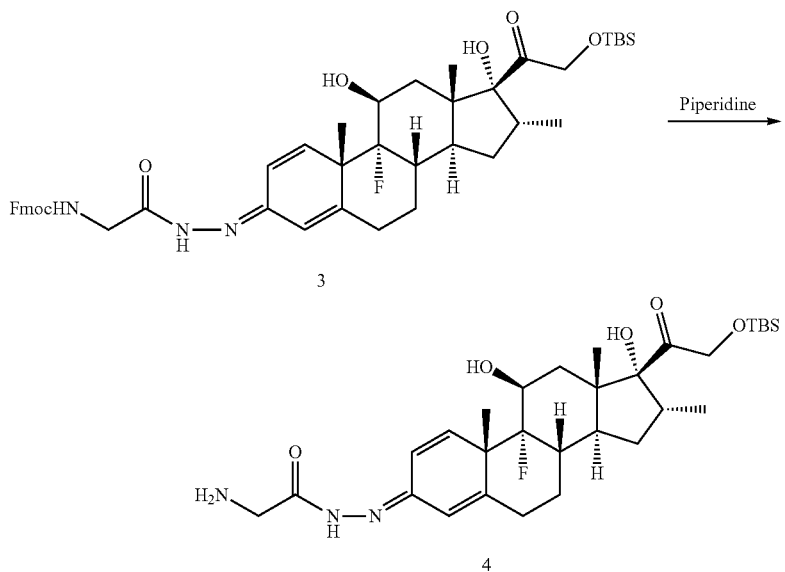

Synthesis of Compound 3:

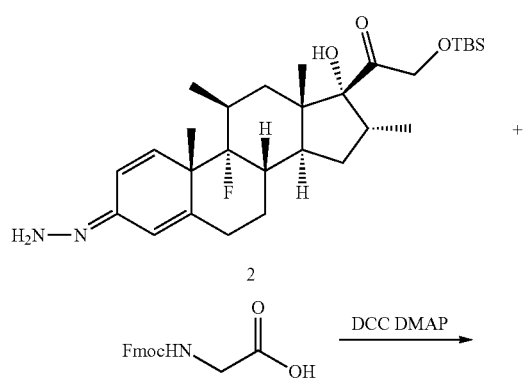

Compound 3 (3.0 g, 3.75 mmol) was dissolved in dichloromethane (DCM, 10 mL). The solution was cooled to 0° C. with ice-water bath. Piperidine (1 mL) was added. The solution was stirred at 0° C. for 1 hour. Ethyl acetate (100 mL) was added and washed with brine (80 mL×3). The organic phase was dried over MgSO₄ and then the solvent was removed. Toluene (50 mL) was added and then evaporated to remove the residue piperidine. The residue was then purified with flash chromatography (ethyl acetate and then ethyl acetate/methanol=2.5/1) to give 1.96 g of compound 4 (90.6% yield).

$^1$H NMR (500 MHz, d$_6$-DMSO): δ (ppm)=7.01 (d, J=10.2 Hz), 6.83 (d, J=10.2 Hz), 6.77 (s), 6.66 (d, J=10.2 Hz), 6.57 (d, J=10.2 Hz), 6.56 (s), 6.43 (d, J=10.2 Hz), 6.38 (d, J=9.8 Hz), 6.27 (d, J=10.2 Hz), 6.18 (d, J=9.8 Hz), 6.00 (s), 5.92 (s), 5.15 (s), 5.13 (s), 4.94 (s), 4.76 (d, J=9.0 Hz), 4.27 (d, J=9.0 Hz), 4.11 (br), 2.88 (br), 2.70-2.50 (m), 2.49 (s), 2.40-2.20 (m), 2.15-2.05 (m), 1.73-1.63 (m), 1.63-1.53 (m), 1.41 (s), 1.40 (s), 1.37 (s), 1.35-1.25 (m), 1.10-1.00 (m), 0.87 (s), 0.84 (s), 0.76 (d, J=6.8 Hz), 0.03 (s), 0.02 (s). MS (ESI): m/z=578.3 (M+H+), calculated: 577.3.

Synthesis of Compound 5:

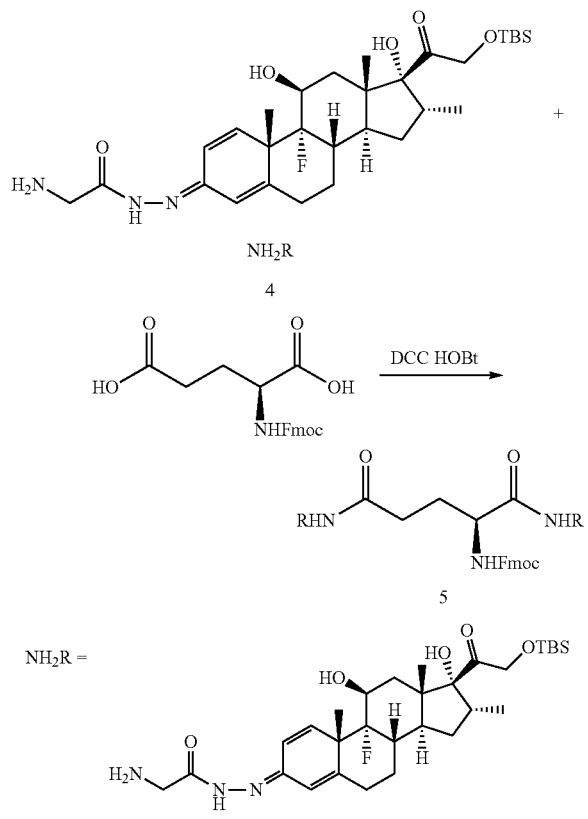

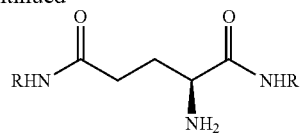

Compound 4 (444 mg, 0.768 mmol) was dissolved in anhydrous DMF (3 mL), Fmoc-glutamic acid (135 mg, 0.366 mmol), DCC (226 mg, 1.098 mmol) and hydroxybenzotriazole (HOBt, 148 mg, 1.098 mmol) were added. The solution was stirred at room temperature for 4 hours. Ethyl acetate (100 mL) was added and washed with brine (80 mL×3). The organic phase was dried over MgSO4 and then the solvent was removed. The residue was then purified with flash chromatography (ethyl acetate/methanol=10/1) to give 471 mg of compound 5 (86.5% yield). Due to the presence of multiple syn/anti-hydrazone groups in the Dex dimer, the assignment of peaks in the $^1$H NMR spectrum of compound 5 was complex, so LC-MS/MS was used to confirm the identity of compound 5.

Synthesis of Compound 6:

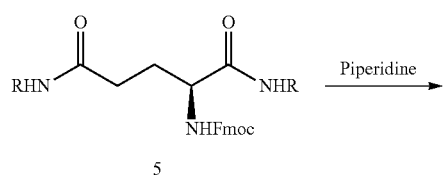

Compound 5 (450 mg, 0.3 mmol) was dissolved in DCM (4.5 mL). The solution was cooled to 0° C. with ice-water bath. Piperidine (1.5 mL) was added. The solution was stirred at 0° C. for 1 hour. Ethyl acetate (100 mL) was added and washed with brine (80 mL×3). The organic phase was dried over MgSO4 and then the solvent was removed. The residue was then purified with flash chromatography (ethyl acetate and followed by ethyl acetate/methanol=3/1) to give 330 mg of compound 6 (86.4% yield). MS (ESI): m/z=1266.7 (M+H+), calculated: 1265.7.

Synthesis of Compound 7 (PEG-DiDex):

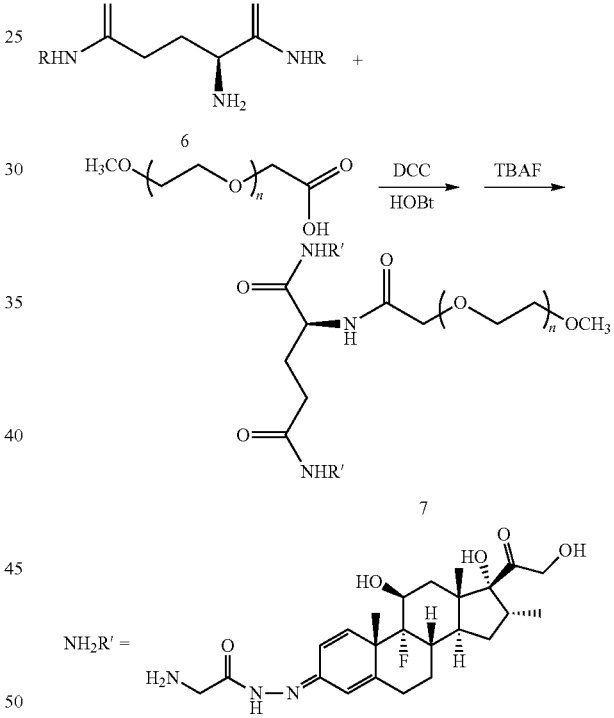

mPEG-COOH (100 mg, 0.052 mmol), HOBt (70.2 mg, 0.52 mmol) and DCC (107 mg, 0.52 mmol) were dissolved in DMF (3 mL) and the solution was stirred at room temperature for 1 hour. Compound 6 (428 mg, 0.34 mmol) was added. The solution was stirred at room temperature for 24 hours and then applied to LH-20 column to separate the polymeric fraction. After evaporation of the solvent, the residue was dissolved in tetra-n-butylammonium fluoride (TBAF, 1 M, 2 mL). The solution was stirred for 2 hours. The resulting solution was again applied onto LH-20 column to give 118.7 mg of compound 7 (PEG-DiDex, 77.8% yield).

MS (ESI): two clusters of peaks were observed in the mass spectrum: one appears at m/z=1550, representing the diion peaks of PEG-DiDex; and the other at m/z=1100, representing triion peaks of PEG-DiDex. The appearance of multiple peaks at each m/z value can be attributed to the polydispersity of mPEG used. For example, the peak at 1546.7 represents diionic peak of PEG-DiDex with 44 repeating ethylene glycol unit in mPEG; the peak at 1068.5 represents triionic peak PEG-DiDex with 46 repeating ethylene glycol units in mPEG.

Synthesis of Symmetric mPEG-(Dex-Dimer) Compound 9

The monomethyl citrate (0.206 g, 1 mmol) is dissolved in anhydrous DMF (15 mL) and the solution is cooled to 0° C. DCC (0.494 g, 2.4 mmol), compound 2 (1.144 g, 2.2 mmol) and DMAP (48.8 mg, 0.4 mmol) are added. The solution is stirred at 0° C. for 3 hours. Ethyl acetate (100 mL) is added and washed with brine (80 mL×4). The organic phase is dried over MgSO₄ and then the solvent is removed. The residue is purified with column chromatography (ethyl acetate/hexanes=1/1) to give compound 8.

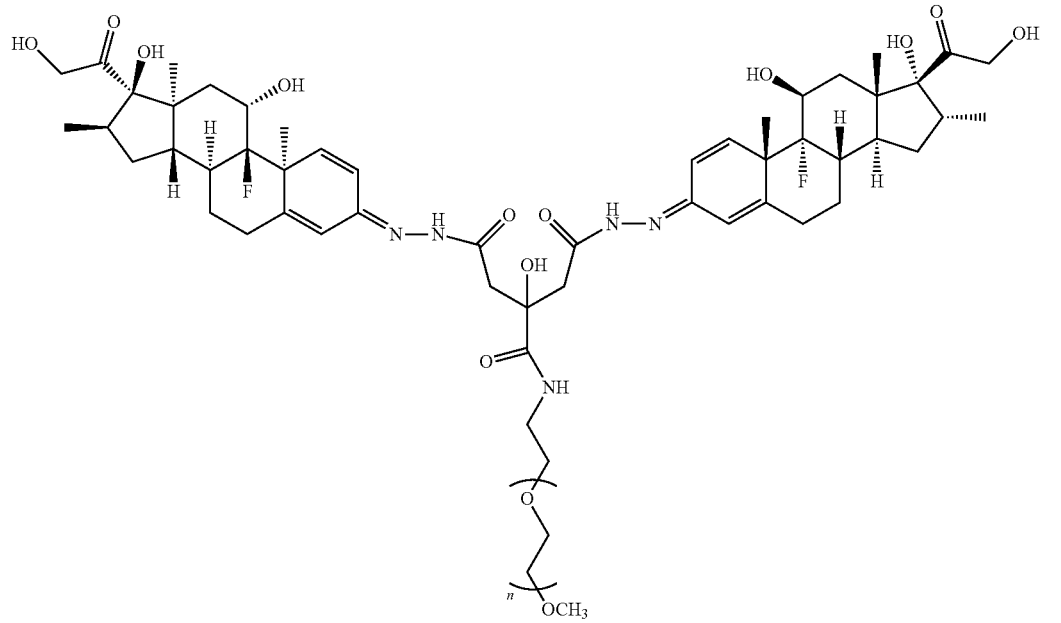

Synthesis of Compound 8:

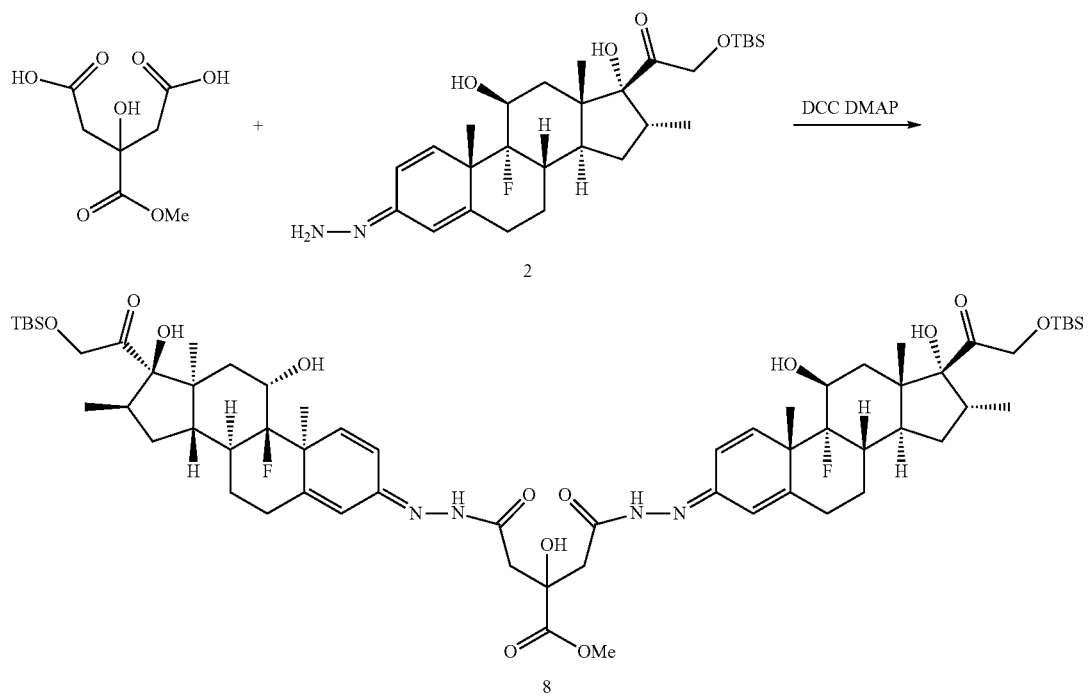

Synthesis of Compound 9:

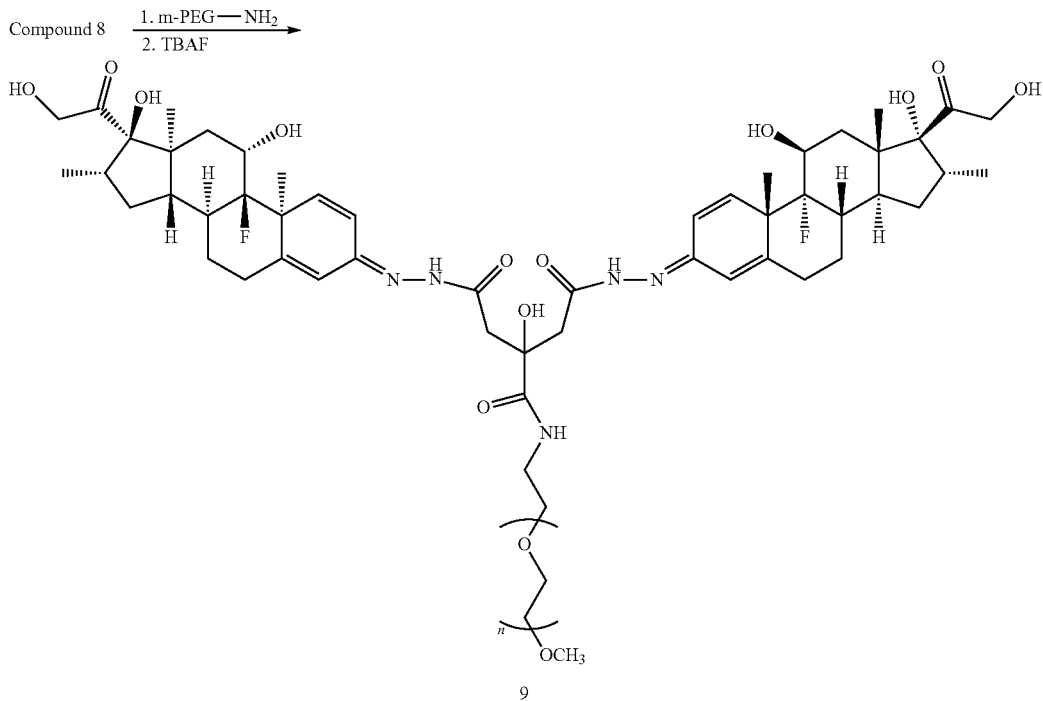

Compound 3 (0.9 g, 0.75 mmol) and mPEG-NH$_2$ (0.285 g, 0.15 mmol) are dissolved in anhydrous DMF (5 mL) and the solution is heated to 80° C. for 6 hours under the protection of Argon. Then the solution is allowed to room temperature and TBAF (3 mL, 1 M in THF) is added. The solution was stirred for 1 hour at room temperature. The solution is then concentrated and then purified by LH-20 chromatography to give Compound 9.

Synthesis of Symmetric mPEG-(Dex-Trimer) Compound 11

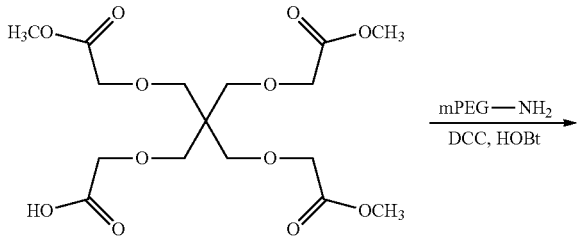

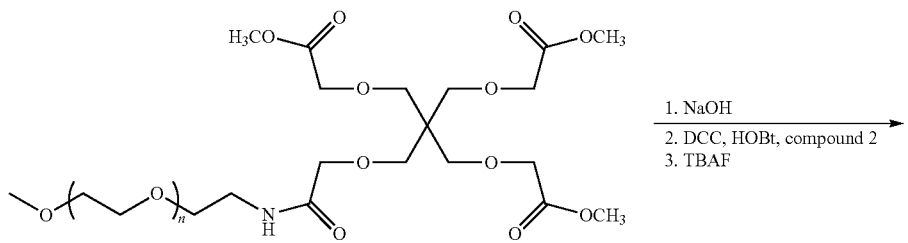

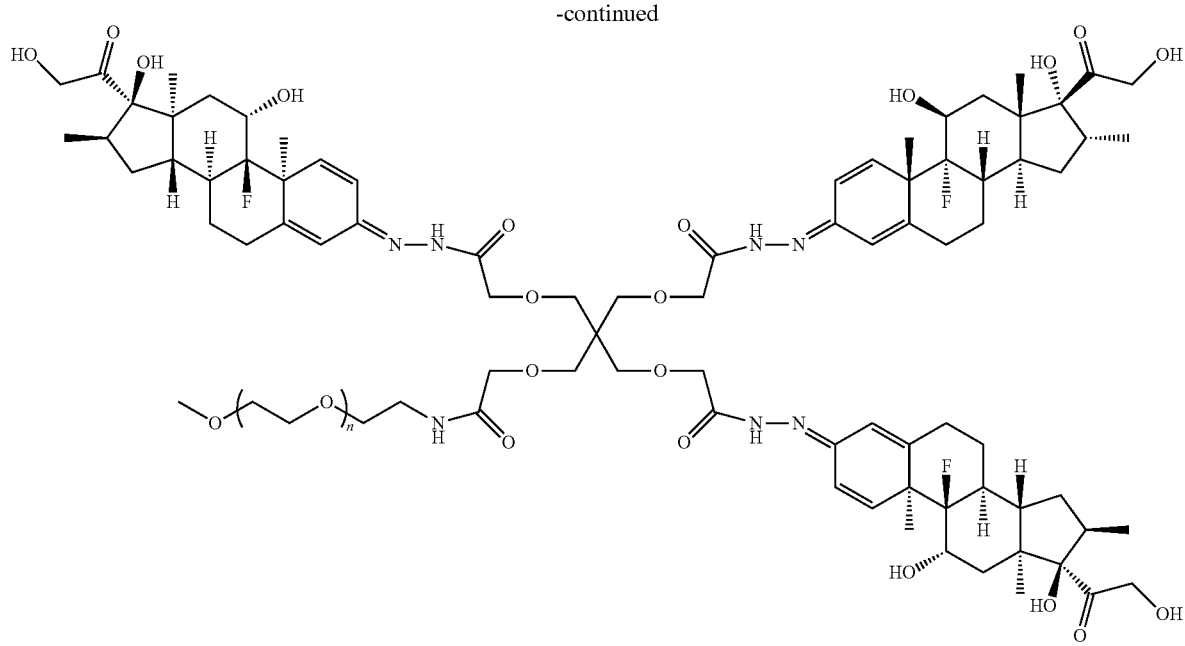
11
Synthesis of Compound 10:
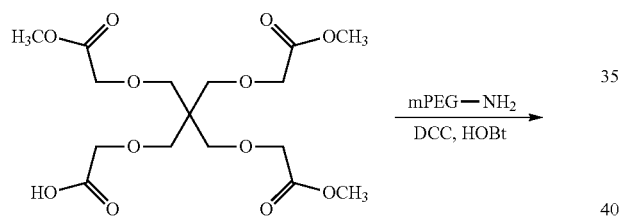
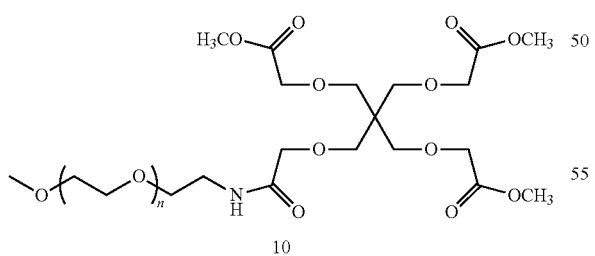
10
The Pentaerythritol derivative (0.41 g, 1 mmol) is dissolved in anhydrous DMF (5 mL). DCC (0.82 g, 4 mmol), HOBt (0.405 g, 3 mmol) and Et$_3$N (0.30 g, 3 mmol) are added and the solution is stirred for 30 min, and mPEG-NH$_2$ (0.38 g, 0.2 mmol) is added. The solution is stirred at room temperature for 20 hours. It is then purified by LH-20 to give compound 10.

Synthesis of Compound 11:

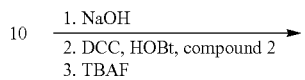

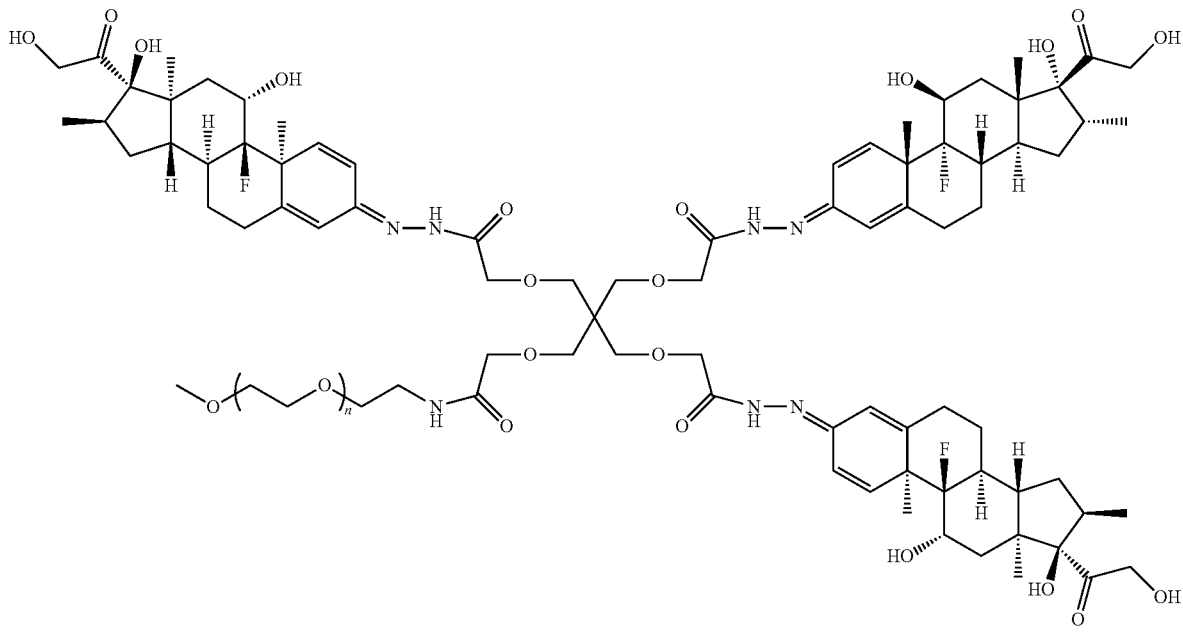

11

Compound 10 (0.23 g, 0.1 mmol) and sodium hydroxide (12 mg, 0.3 mmol) are dissolved in a mixture solution of methanol and water (1:1, 5 mL). The solution is stirred at room temperature for 5 hours. Then HCl (3 mL, 1M) is added. The solvent is then removed and the residue is purified by LH-20 to give the deprotected intermediate. It is then dissolved in anhydrous dichloromethane (5 mL). DCC (0.30 g, 1.5 mmol), HOBt (0.20 g, 1.5 mmol) and Et$_3$N (0.15 g, 1.5 mmol) are added and the solution is stirred for 30 min, then compound 2 (0.62 g, 1.2 mmol) is added. The solution is stirred at room temperature for 20 hours. The solution is then loaded on to a silica gel column and ethyl acetate/hexanes=1:1 is used as eluent to recover the unreacted compound 2. Then methanol is used as eluent to get the crude product. The solvent is then removed and the residue is dissolved in THF (5 mL) and TBAF (1.5 mL, 1 M in THF) is added. The solution is stirred at room temperature for 1 hour. The solution is then concentrated and purified by LH-20 to give the final product compound 11.

Synthesis of mPEG-Dex, Compound 12

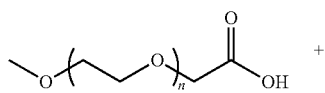 +

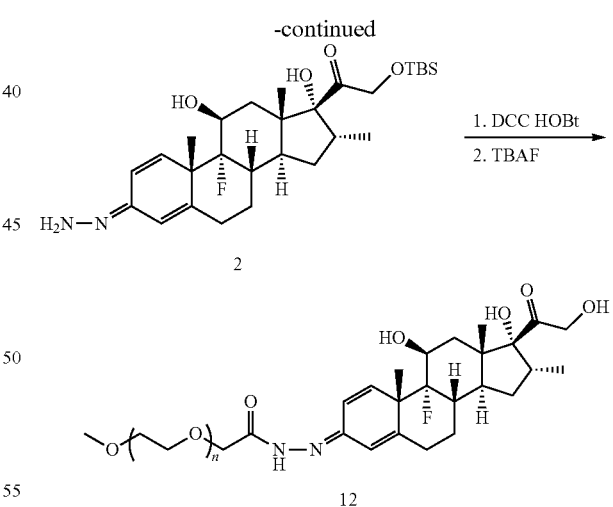

Synthesis of Compound 12:

mPEG-CH$_2$COOH (0.19 g, 0.1 mmol) was dissolved in anhydrous DMF (5 mL). DCC (0.21 g, 1 mmol), HOBt (0.135 g, 1 mmol) and Et$_3$N (0.1 g, 1 mmol) were added and the solution was stirred for 30 min, and then the compound 2 (0.26 g, 0.5 mmol) was added. The solution was stirred at room temperature for 20 hours. TBAF (0.5 mL, 1 M in THF) was added and the solution was stirred for 1 hour, followed by LH-20 purification to give compound 12.

Synthesis of Symmetric Dex-PEG-Dex Compound 13

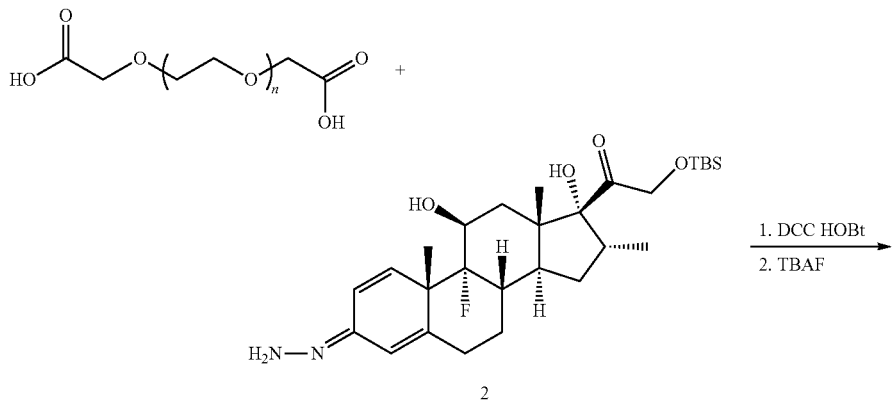

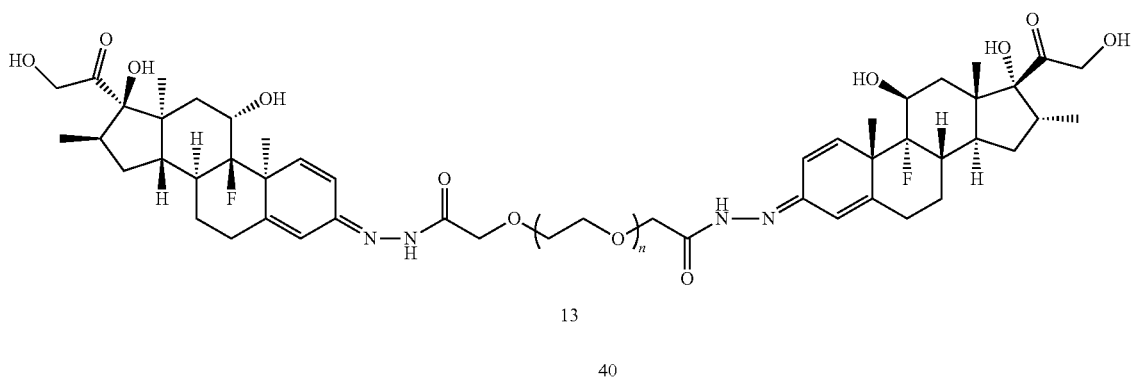

Synthesis of Compound 13:

HOOCCH$_2$-PEG-CH$_2$COOH (0.14 g, 0.07 mmol) was dissolved in anhydrous DMF (5 mL). DCC (0.142 g, 0.7 mmol), HOBt (0.093 g, 0.7 mmol) were added and the solution was stirred for 30 min, and then the compound 2 (0.398 g, 0.7 mmol) was added. The solution was stirred at room temperature for 15 hours. TBAF (1 mL, 1 M in THF) was added and the solution was stirred for 1 h and then purified by LH-20 to give compound 13.

Synthesis of Asymmetric mPEG-(Dex-Tetramer) Compound 15

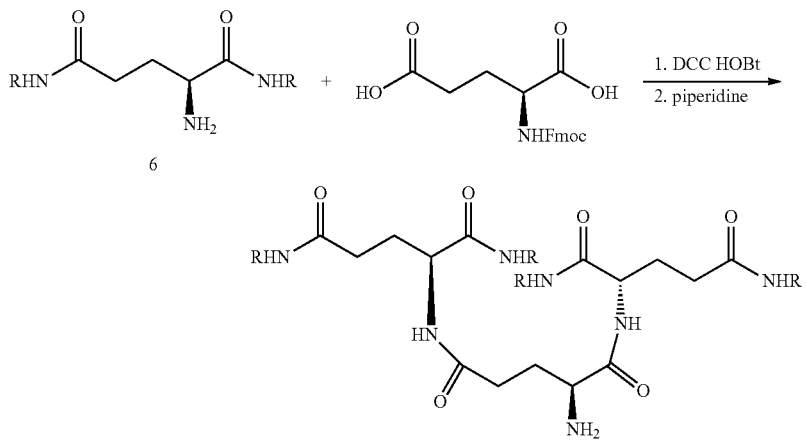

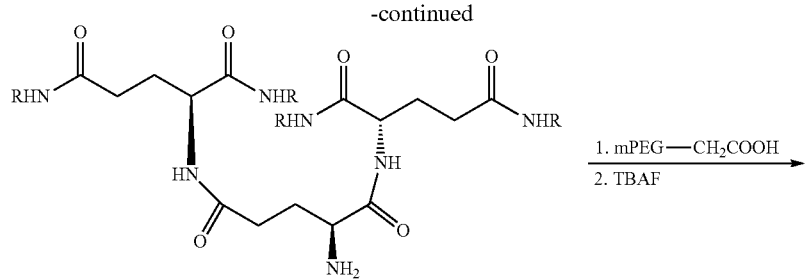
14
1. mPEG—CH₂COOH
2. TBAF
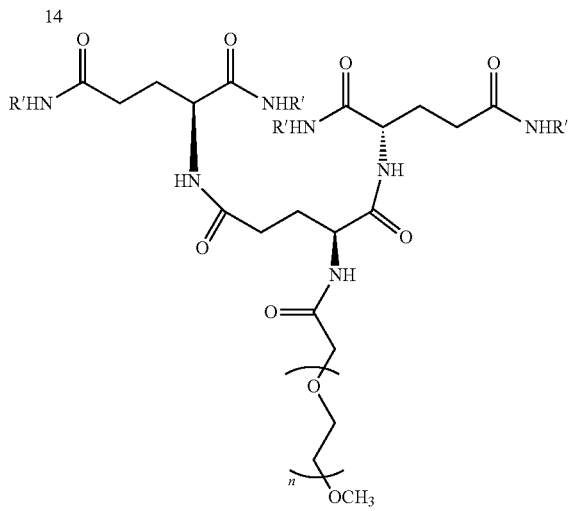
15
$NH_2R =$
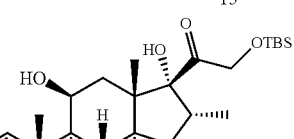
$NH_2R' =$
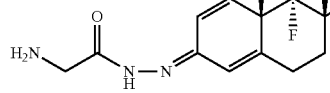
Synthesis of Compound 14:
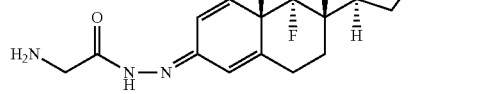
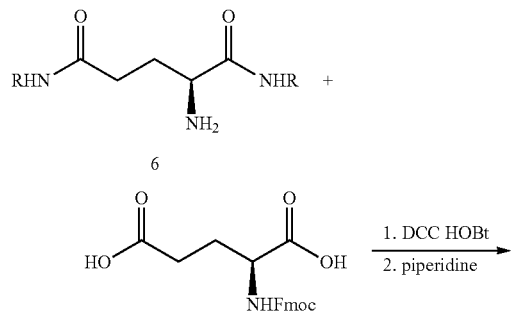
6
1. DCC HOBt
2. piperidine
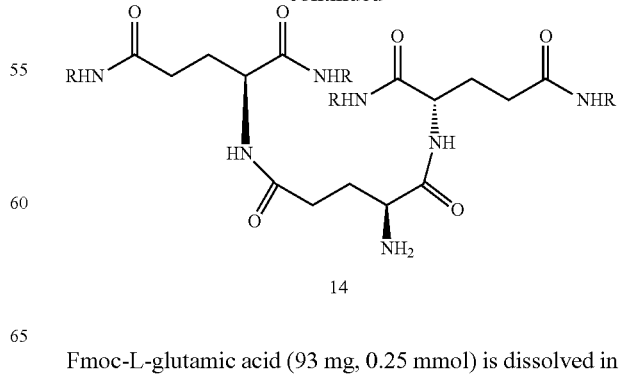
14
Fmoc-L-glutamic acid (93 mg, 0.25 mmol) is dissolved in anhydrous DMF (5 mL). DCC (0.62 g, 3 mmol), HOBt (0.41 g, 3 mmol) are added and the solution is stirred for 30 min, and then compound 6 (0.79 g, 0.625 mmol) is added. The solution is stirred at room temperature for 15 hours. Ethyl acetate (100 mL) is added and washed with brine (80 mL×4). The organic phase is dried over MgSO$_4$ and then the solvent was removed. The residue is purified with flash chromatography (ethyl acetate/methanol=5/1) to give the product which is dissolved in dichloromethane (3 mL), piperidine (1 mL) is then added and the solution is stirred for 1 hour and then the solution is purified by column chromatography (ethyl acetate/methanol=2.5/1) to give compound 14.

Synthesis of Compound 15:

Micelle Characterization

The average hydrodynamic diameter, polydispersity index (PDI) and ζ-potential of the micelles were determined by dynamic light scattering (DLS) using a Zetasizer Nano ZS90 (Malvern Instruments, Worcestershire, UK). The intensity of scattered light was measured at a 173° scattering angle. To understand the micelles morphology, transmission electronic microscopy (TEM) was used to visualize micelles deposited on formvar/silicone monoxide coated 200 mesh copper grids surface.

Pyrene-based fluorescence polarization method was used to determine the critical micelle concentration (CMC) for PEG-DiDex. For sample preparation, known amounts of

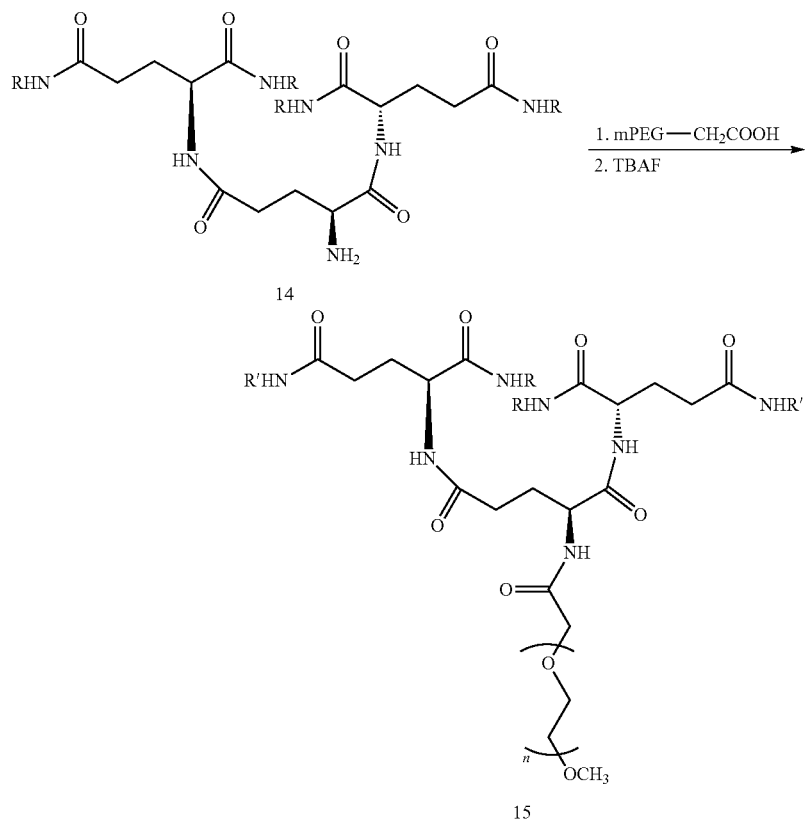

The mPEG-CH$_2$COOH (50 mg, 0.025 mmol) is dissolved in anhydrous DMF (3 mL). DCC (0.10 g, 0.5 mmol), HOBt (68 mg, 0.5 mmol) are added and the solution is stirred for 30 min, and then the compound 14 (0.43 g, 0.15 mmol) is added. The solution is stirred at room temperature for 15 hours. TBAF (0.5 mL, 1 M in THF) is added and the solution is stirred for 1 hour and then the solution is purified by LH-20 to give compound 15.

Characterization and Testing of PEG-Dex Dimer Prodrug (PEG-DiDex)

Formation of PEG-DiDex Micelles

With an amphiphilic structural design, PEG-DiDex can form micelles through self-assembly. PEG-DiDex (26.5 mg) was dissolved in distilled water (1 mL) and equilibrated at 37° C. for 4 hours to allow micelles formation. The micelle solution was then diluted to 3 mg/mL (1.02×10$^{-3}$ M) by adding double distilled water and then used for the following characterization.

stock solution of pyrene in acetone were added to empty wells of 96-well plate. Aqueous solutions of PEG-DiDex at different concentrations were added to the wells and evaporate for 2 hours at room temperature. The pyrene concentration in the final solution was 0.6 μM, which is slightly below its water solubility in water at room temperature. Before measurement, the samples from each well were transferred to a quartz 96-well plate, and the fluorescence intensity was measured with excitation wavelength of 334 nm and emission wavelength at 373 nm (I1) and 384 nm (I3) using a fluorescence microplate spectrofluorometer (Molecular Devices, Sunnyvale, Calif.). Ratio of fluorescence intensity I1/I3 was plotted against prodrug concentration to obtain the CMC value.

To understand the impact of pH values and the presence of serum proteins on the release of Dex from PEG-DiDex, the prodrug (3 mg/mL) was dissolved in acetate buffers (pH=5.0, 6.5 and 7.4) and mouse serum (0.2 wt % sodium azide as bacteriostat). Pluoronic F127 was added as in order to create sink condition. The micelle solutions were placed in a shaking incubator (60 r/min) at 37° C. At selected time points, the releasing solution (0.5 mL) was withdrawn, neutralized with NaOH (0.1 M) and analyzed with HPLC to determine the free Dex concentration. The analysis of each sample was performed in triplicate. The accumulative release of Dex from PEG-DiDex micelles was calculated according the following equation, where $C_i$ refers to the concentration of Dex at time i.

$$\text{Accumulative release (wt \%)} = \frac{V_i \times C_i + 0.5 \times \sum_{i=1}^{n-1} C_i}{\text{weight of Dex in the micelles}} \times 100\%$$

To quantify the Dex content in PEG-DiDex, the prodrug (1 mg) was dissolved in HCl (0.5 mL, 0.1 N) overnight. The sample (50 μL) was withdrawn and neutralized by addition of NaOH (50 μL, 0.1 N), then diluted in acetonitrile (CAN, 0.9 mL). The sample (in triplet) was analyzed using an Agilent 1100 HPLC system equipped with a reverse phase C18 column (Agilent, ZORBAX 300SB-C18, 4.6×250 mm, 5 m). Mobile phase: acetonitrile/water=30/70; detection wavelength, 240 nm; flow rate, 1 mL/min; Injection volume, 10 μL. The Dex content in PEG-DiDex was then calculated based on the HPLC analysis result.

Testing Results

Dynamic light scattering (DLS) measurement indicates that the PEG-DiDex can indeed form micelle with an average micelle diameter of ~11 nm, a polydispersity index (PDI) of 0.345 and a c-potential of −5±4.61 mV. As shown in the TEM images (FIG. 2), the micelles deposited on the substrate showed an average ~30 nm diameter. The size discrepancy with the DLS measurement may be attributed to the collapse of the micelles during the sample preparation process. Using pyrene-based fluorescence polarization method, the critical micelle concentration (CMC) value of PEG-DiDex was determined to be $2.5 \times 10^{-4}$ M.

Figure 3:
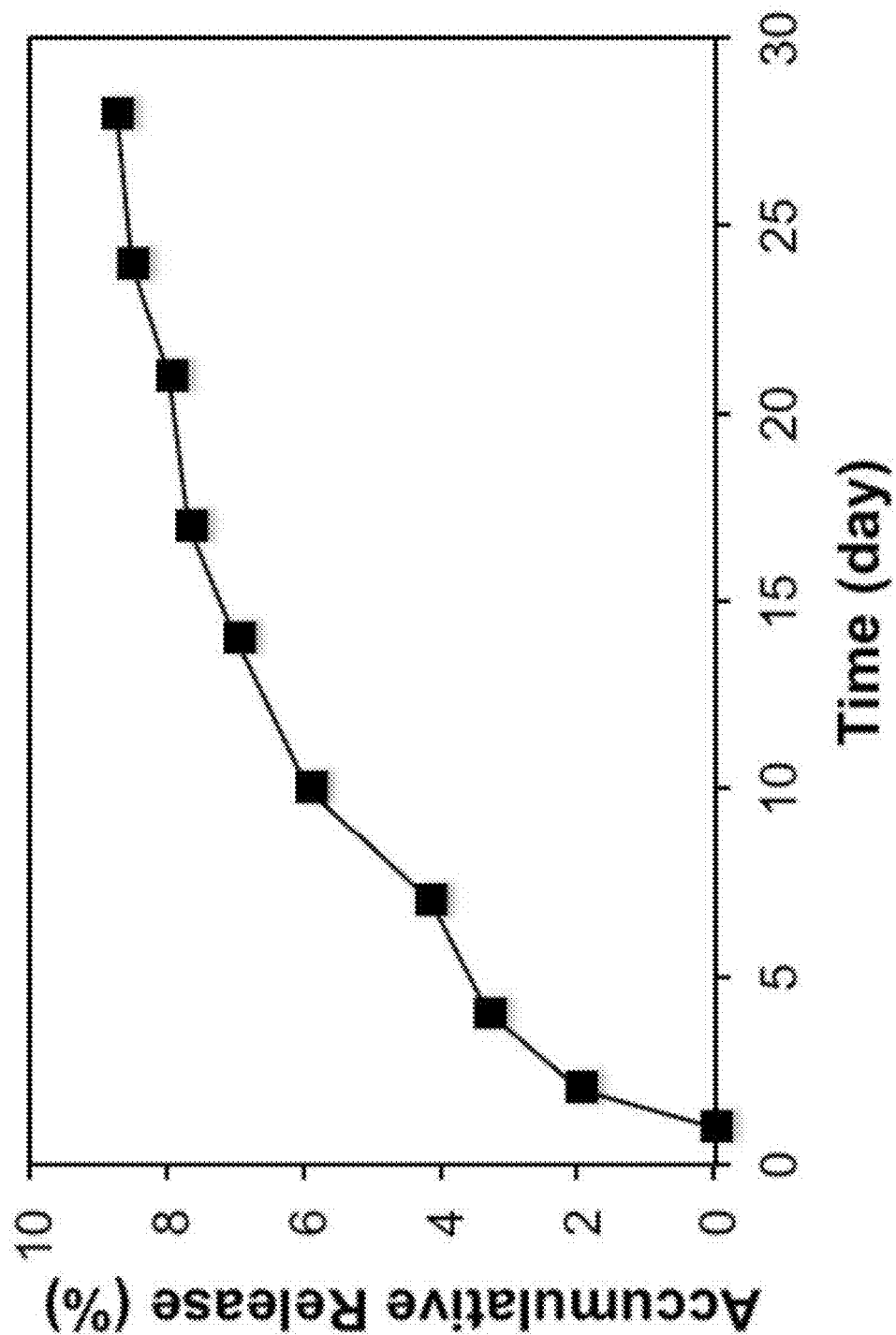
FIG. 3 illustrates the release of Dex from PEG-DiDex in acetate buffer (pH=5.0) at 37° C. Pluronic F127 was added to create the sink condition.

As the Dex activation trigger, the hydrazone bond in the PEG-DiDex design can only be cleaved via acidic environment. This was confirmed by the in vitro drug release experiment. As shown in FIG. 3, at pH=5.0 in acetate buffer, 2% of the Dex loading was released within the first two days. It was then followed by a sustained release at roughly 0.27%/day for the next 26 days.

Treating Lupus Nephritis with PEG-DiDex

Beginning at 20 weeks of age, NZB/W F1 female mice (Jackson Laboratories, Bar Harbor, Me.) were randomized into three test groups (saline control, Dex and PEG-DiDex). Their urine protein level was monitored weekly using Albustix Reagent Strips (Siemens Healthineers). Only mice with established nephritis, as evidenced by sustained albuminuria (≥100 mg/dL) over 2 weeks, were enrolled in the study. PEG-DiDex treatment (106 mg/kg, containing 28 mg/kg of dexamethasone, n=10) and saline (n=12) were administered as a monthly i.v. injection. The Dex treatment (dexamethasone 21-phosphate disodium, 1.32 mg/kg, containing 1.00 mg/kg of dexamethasone, n=11) was given as daily i.v. injection. All treatments continued for 8 weeks. The body weight and proteinuria level of the animals was monitored on a weekly basis. Peripheral blood was collected from saphenous vein every 4 weeks for serum analyses. Mice that developed severe proteinuria (≥2000 mg/dl) or showed signs of distress (e.g. reduced mobility, weight loss >20%, edema, unkempt appearance) were sacrificed immediately. The surviving mice were monitored for an additional two weeks after the last treatment. The mice were then euthanized by $CO_2$ asphyxiation, with all major tissues and organs isolated, weighted and processed at necropsy. All animal procedures were approved by the Institutional Animal Care and Use Committee (IACUC) of University of Nebraska Medical Center (UNMC).

Analysis of Bone Quality

Femoral bone quality was analyzed using a Skyscan 1172 micro-CT system. The micro-CT scanning parameters were set as the following: voltage 48 kV, current 187 μA, exposure time 620 msec, resolution 6.07 m, and aluminum filter 0.5 mm. Three-dimensional reconstructions were performed with NRecon and DataViewer software (SkyScan). Trabecular bone was selected for analysis based on a polygonal region of interest within the center of the femur, starting at 20 slices (0.25 mm) proximal from the growth plate and extending proximally 80 slices (0.99 mm) further. Trabecular bone volume/tissue volume (BV/TV), the mean bone mineral density (BMD), trabecular number and thickness were quantified with CTAn software (SkyScan).

Near-Infrared Imaging Study

After the proteinuria was established, NZB/W F1 mice (n=6) were given IRDye 800 CW-labeled PEG-DiDex (IRDye 800 CW dose at 148 nmol/kg, Dex equivalent dose of 28 mg/kg) via tail vein injection. The same dose of IRDye 800 CW-labeled PEG-DiDex was also given intravenously to NZW mice (n=6, healthy control). At selected time points (1 and 4 days post administration), the mice were euthanized and perfused with saline. All major organs (i.e. heart, lung, liver, spleen, kidney and adrenal gland) were isolated and imaged using a LI-COR Pearl™ Impulse Small Animal Imaging System to evaluate the distribution and retention of PEG-DiDex.

Flow Cytometry Analysis

After the proteinuria was established, NZB/W F1 mice (n=6) and NZW mice (healthy control) were given Alexa Fluor 488-labeled PEG-DiDex (Alexa Fluor 488 dose at 300 nmol/kg, Dex equivalent dose of 28 mg/kg) via tail vein injection. At selected time points (1 and 4 days post administration), the animals were euthanized and perfused. White blood cells were isolated from peripheral blood. Bone marrow, kidney, spleen and liver were harvested, macerated, and passed through a 70-μm strainer to prepare single-cell suspensions. Cells were marked by the following antibodies: PE-labeled anti-mouse CD3e(17A2), CD11b, F4/80, NK1.1, CD146, prominin (Miltenyi Biotec) and CD19 (eBioscience Inc.); APC-labeled anti-mouse CD11c, Ly-6G, CD326, CD117; anti-mouse GL7-eFluor660. The cells were analyzed using a FACSCalibur flow cytometer (BD Biosciences).

Statistics

Most of the statistical analyses were performed using SPSS software (version 19.0). The data that does not assume to follow a normal distribution was compared using the Kruskal-Wallis test, a nonparametric alternative to one-way analysis of variance. To evaluate specific differences between experimental groups, Tukey's post hoc test and Mann-Whitney U test were used in the comparisons of normal-distributed and non-normal distributed data respectively. Two-tailed P values ≤0.05 were considered significant.

For inflammatory cytokine/chemokine analysis, the data obtained were log 2 transformed to make them more normally distributed. The mixed effects model with AR(1) correlation among repeated measures over time of the same animal were used to fit the log transformed cytokine expression values for each cytokine separately. Three different comparisons were conducted to evaluate (1) difference between the treatment groups at each observation time; (2) difference between different times within each treatment group; and (3) difference in the change of the cytokines expression from baseline among different treatment groups. The Benjamini-Hochberg method was used to control the false discovery rate for multiple comparisons. The results on the differences at log-scaled data, the standard error, the raw p value without adjustment for false discovery rate, and the adjusted p value for BH false discovery rate control were reported.

Figure 2:
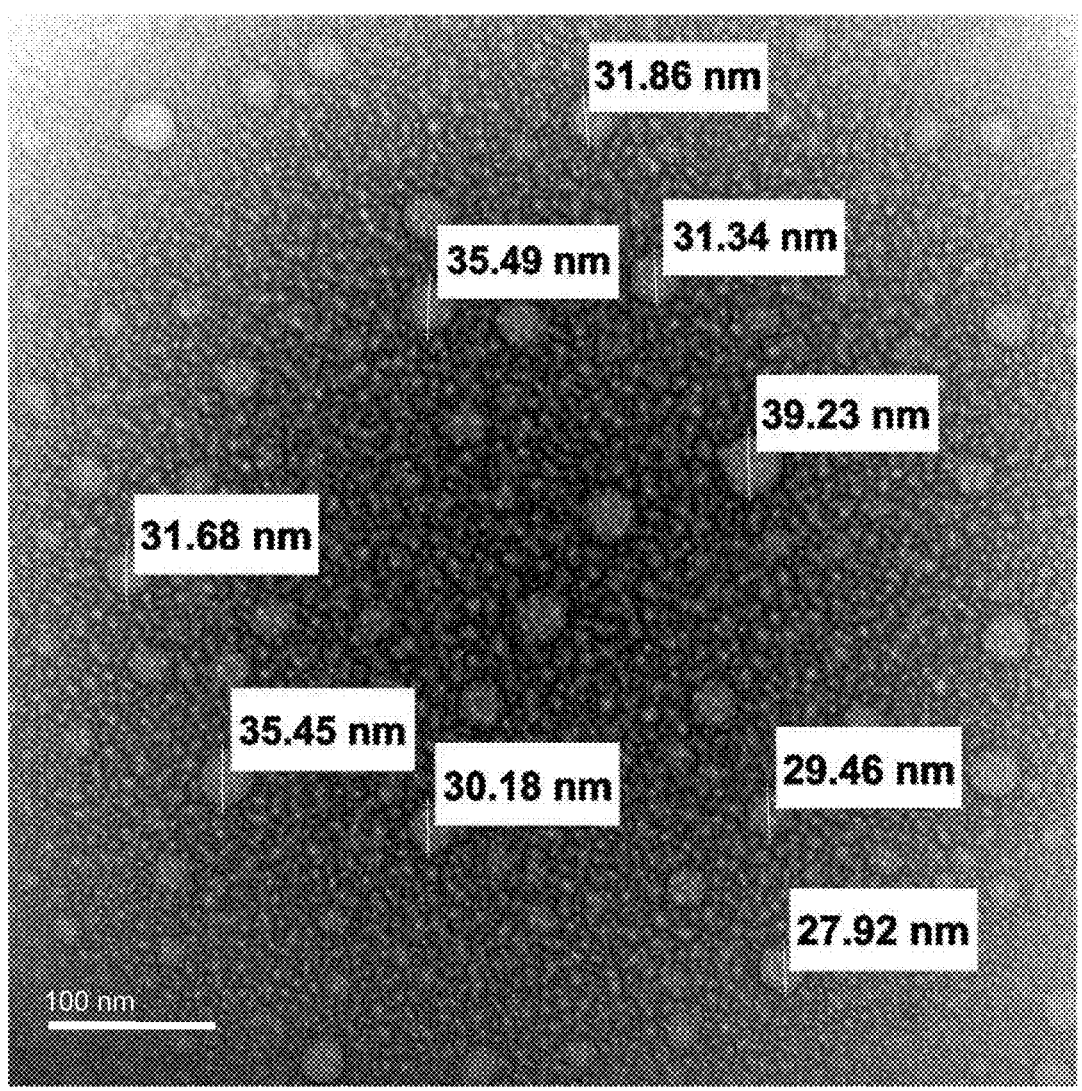
FIG. 2 illustrates transmission electron microscope image of PEG-DiDex micelles deposited on formvar/silicone monoxide coated 200 mesh copper grids surface. The estimated average diameter of the micelles is ~30 nm.

PEG-DiDex Effectively Ameliorated Proteinuria and Improved the Survival of NZB/W F1 Mice with Severe Nephritis To evaluate the therapeutic potential of PEG-DiDex, it was given was administered monthly to NZB/W F1 female mice (~28 wks) with fully developed developed nephritis, as evidenced by sustained albuminuria. The treatment was continued for 8 weeks. Dose equivalent daily Dex treatment and monthly saline administration were used as controls. As shown in FIG. 4A, 2 months PEG-DiDex treatment result in albuminuria resolution in 60% of the mice tested. For the daily Dex treatment group, only 18% of resolution was achieved at the end of the experiment. Over the entire experimental time course, albuminuria persisted in 100% of the mice of the saline group. A total of 42% of mice in saline group have to be euthanized due to severe nephritis (FIG. 4B), as mandated by IACUC protocol. This observation is in agreement with others' finding of the median survival age of NZB/W F1 mice to be around 36 wks. While daily Dex treatment improved the mice survival to ~82%, all animals survived at the end of the experiment in the PEG-DiDex treated group, suggesting a superior therapeutic efficacy than daily Dex treatment.

For additional evidence of PEG-DiDex's superior therapeutic efficacy, the kidneys from the tested animals were further sectioned and stained with PSA. They were then examined by a pathologist (KWF), who was blind to the group design. The periodic-acid schiff (PAS) stained kidney sections were also graded by a histopathologic score system with a 4-point scale. As shown in FIG. 5, more than 40% of the mice from Dex and saline group showed histological evidence of severe glomerulonephritis (scored 3 and 4 points) typified by wire-loop lesions, acute tubular necrosis (ATN), glomerular scarring, cellular crescents and hyaline thrombi formation. In contrast, in PEG-DiDex treated group, only ~11% of the mice were graded as severe glomerulonephritis, which was significantly lower than that in saline and Dex groups. Histological abnormalities were observed in 26% glomeruli in PEG-DiDex group, which is close to the frequency (21.6%) found in the NZW mice. Comparing to this observation, 40% and 52% glomeruli in Dex and saline groups were found to be abnormal respectively, which further support the superior therapeutic efficacy of PEG-DiDex in treating lupus nephritis.

PEG-DiDex Treatment Attenuates Tissue-Damaging Proinflammatory Cytokines/Chemokines.

As shown in FIG. 6, only animals treated with PEG-DiDex caused statistically significant reduction in MCP-1, IFN-β, and IFN-γ values at the end of 2-month treatment. Dex treatment, on the other hand, did not induce the improvement.

PEG-DiDex Treatment does not Lead to Typical GC Toxicities

Figures 7A, 7B, 7C, 7D, 7E, 7F:
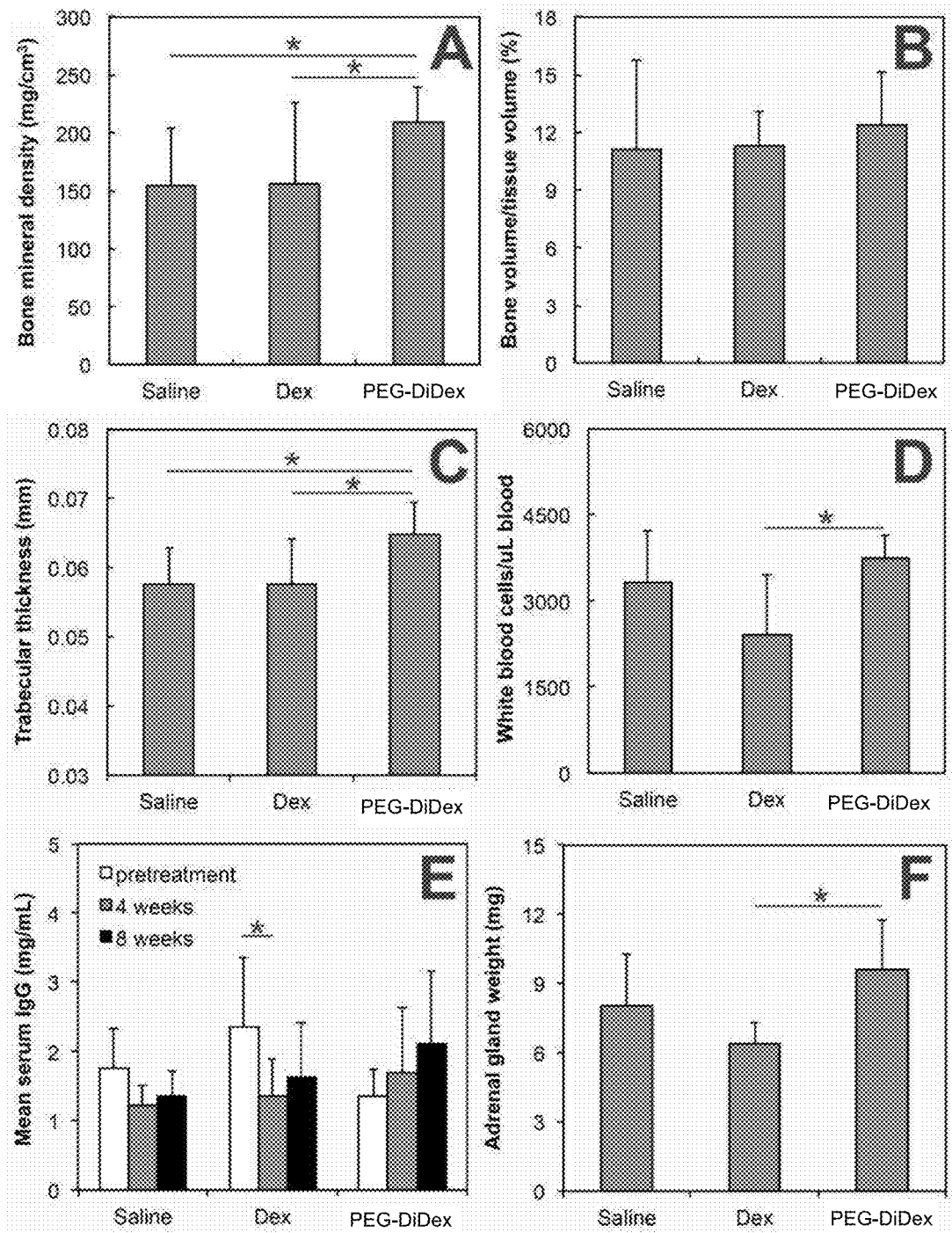
FIGS. 7A, 7B, 7C, 7D, 7E, and 7F illustrate that two months of PEG-DiDex micelle treatment of NZB/W F1 mice did not lead to typical glucocorticoid toxicities. (A) PEG-DiDex micelles treatment is significantly better in preserving bone mineral density (BMD) than Dex treatment; (B) PEG-DiDex micelles treated mice have a trend of higher bone volume/tissue volume (BV/TV) than those from the Dex and saline groups; (C) PEG-DiDex micelles treated mice have a significantly higher trabecular thickness (Tb.Th.) value than Dex and saline groups; (D) PEG-DiDex micelles treated mice have a significantly higher white blood cell (WBC) count than Dex treated mice; (E) PEG-DiDex treatment did not cause significant reduction of total serum IgG level, while Dex treatment did, which is a sign of potential immune suppression; (F) Different from Dex treatment, PEG-DiDex treatment does not induce adrenal gland atrophy. The asterisk (*) indicates a statistically significant difference ($P<0.05$).

To understand the impact of PEG-DiDex treatment on bones, the femoral mean bone mineral density (BMD) and micro-architecture were evaluated using a high resolution ri-CT (Skyscan 1172). The BMD value and trabecular thickness in the femoral trabecular bone of PEG-DiDex treated mice were significantly higher than that observed in both saline and Dex group (FIG. 7A, C; P<0.05). A trend of increase in trabecular bone volume/tissue volume (BV/TV) value was also observed, though such increase is not statistically significant (FIG. 7B, P>0.05). Comparing to NZW mice (as a healthy control), even the saline group exhibits significantly lower values of BMD, BV/TV and trabecular thickness (data not shown), which suggest the systemic inflammatory condition of NZB/W F1 mice is detrimental to the skeletal quality. The PEG-DiDex treatment not only avoided the negative GC impact on the bone, but also further impeded the inflammation-associated skeletal deterioration by effective amelioration of nephritis.

Chronic exposure to GC therapy is known to be associated with systemic immunosuppression. To understand if PEG-DiDex as a GC prodrug would be similarly immune suppressive, we evaluated the end point total serum IgG level and the peripheral white blood cell (WBC) counts during the time course of the experimental. As shown in FIG. 7D, PEG-DiDex treated mice exhibited a WBC counts similar to the saline group, but at a significantly higher value than the Dex treated group (P<0.05). Also see in FIG. 7E, PEG-DiDex monthly administration did not alter serum IgG level during the course of the treatment, while the animals treated with daily Dex had a significant drop of serum IgG value after 1 month of treatment (P<0.05). These data collectively suggest the absences of signs of immune suppression in animals treated with PEG-DiDex.

GC exposure, even in short term may suppress hypothalamic-pituitary-adrenal (HPA) axis, leading to clinical atrophy of the adrenal gland. To understand if PEG-DiDex treatment would cause adrenal gland atrophy, we analyzed the end point adrenal gland mass. The mean adrenal gland mass in the Dex group was significantly lower than the PEG-DiDex group (FIG. 7F; P<0.05). There was no significant difference in adrenal gland mass between the PEG-DiDex and saline groups (FIG. 7F; P>0.05). These data suggest that treatment by PEG-DiDex would not induce adrenal gland atrophy.

PEG-DiDex Passively Targeted to Nephritic Kidneys in NZB/W F1 Mice

Figure 8:
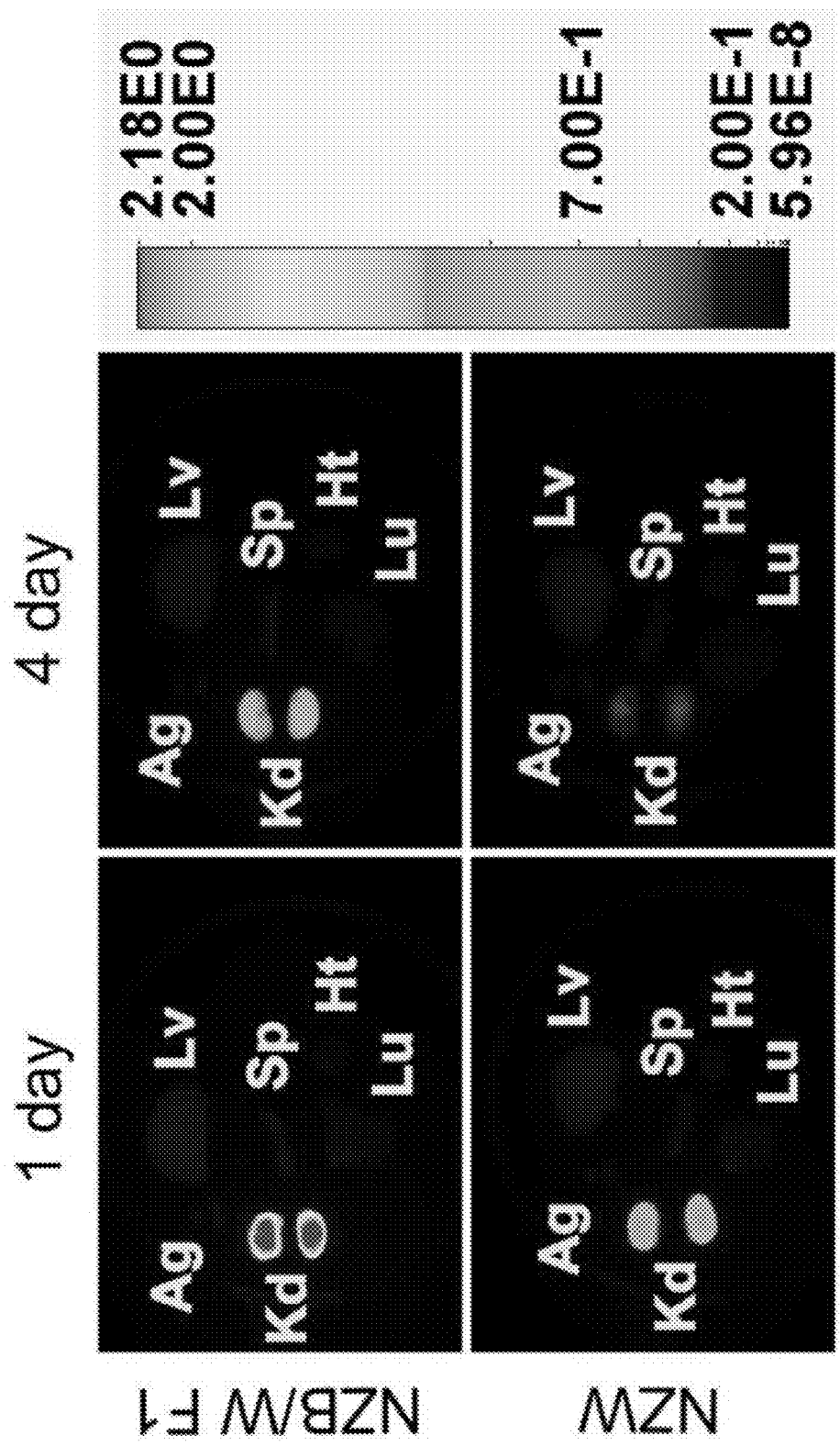
FIG. 8 illustrates passive targeting of IRDye labeled PEG-DiDex to nephritis in NZB/W F1 mice. NZW mice were used as control. At different time points post tail vein injection (1 and 4 days), heart (he), lung (lu), kidney (kd), liver (lv), spleen (sp) and adrenal gland (ad) were isolated after saline perfusion and subjected to near infrared imaging. Pseudo color-coded signal intensity reflect the level of PEG-DiDex within the organ examined.

To understand the potentiated therapeutic efficacy and greatly reduced GC-associated toxicities of PEG-DiDex (a GC prodrug), the in vivo biodistribution of PEG-DiDex was analyzed using near-infrared optical imaging. Both NZB/W F1 mice and NZW mice received intravenous injections of IRDye 800 CW-labeled PEG-DiDex. The animals were sacrificed on day 1 and day 4 post injection and all vital organs (i.e. heart, lung, liver, spleen, kidney and adrenal gland) were harvested for the optical imaging. As shown in FIG. 8, in NZB/W F1 mice, the IRDye-labeled PEG-DiDex primarily accumulated in the kidneys and can be retained there for at least 4 days. For NZW mice, PEG-DiDex was found to accumulate in kidneys, but the signal intensity of the retained prodrug was at a much lower level especially at 4 days post administration, suggesting the inflammatory condition of the kidneys may especially facilitate the passive targeting and retention of the prodrug in nephritis.

PEG-DiDex Treatment does not Alter Serum Anti-dsDNA Level

Figure 9:
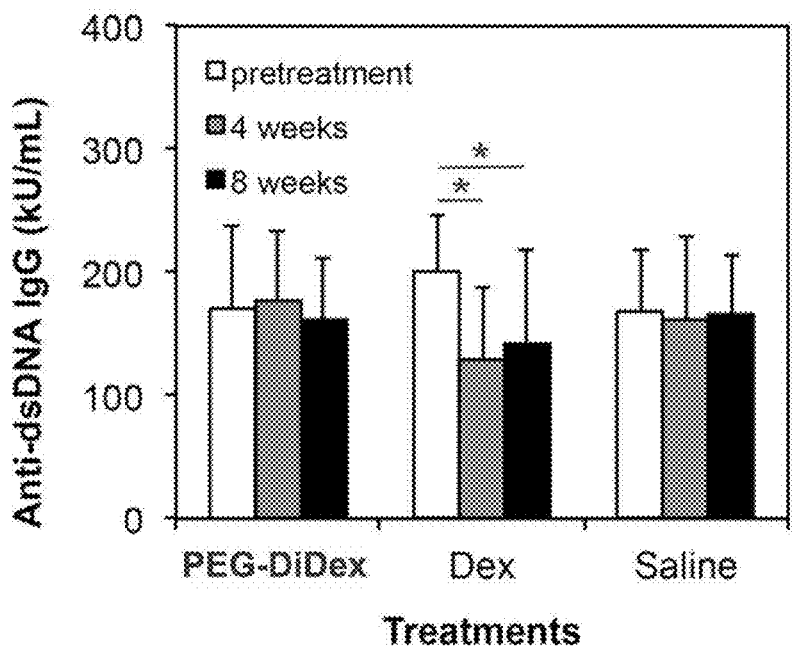
FIG. 9 illustrates the impact of different treatment regiments on the serum anti-dsDNA IgG level. While Dex daily treatment significantly reduced the antibody level, dose equivalent monthly PEG-DiDex treatment had not impact.

GCs are known to exert its therapeutic effect against lupus partially through down regulation of anti-dsDNA antibody level. Therefore, it would be of great interest to see if a Dex prodrug, such as PEG-DiDex, treatment would ameliorate lupus symptoms according to a similar pharmacology. As shown in FIG. 9, daily Dex treatment was found to significantly reduce serum anti-dsDNA IgG levels at both 4 and 8 weeks post-treatment initiation. For saline and PEG-DiDex treatments, however, no significant impact on the anti-dsDNA IgG level was observed at either time point.

Characterization of PEG-DiDex and Drug Loading Efficiency

Effective hydrodynamic diameters ($D_{eff}$) and polydispersity index (PDI) of PEG-DiDex dimer were measured by dynamic light scattering (DLS) using a Zetasizer Nano ZS90 (Malvern Instruments, Worcestershire, UK). PEG-DiDex dimer was dissolved into PBS (pH 7.4) at a concentration of 2 mg/mL. The DLS analysis showed the hydrodynamic size for PEG-DiDex dimer was 273.5 nm with a PDI value of 0.464.

To quantify Dex loading in PEG-DiDex, 1 mg of the prodrug was dissolved in 0.5 ml of buffer (HCL, 0.1N) overnight. 50 µl of the sample was neutralized by 50 ul NaOH (0.1N), and then diluted in 0.9 ml ACN. 1 ml of the sample (triplet) was analyzed with an Agilent 1100 HPLC system with a quaternary pump (with degasser), an autosampler and a diode-array based UV detector. Mobile phase, acetonitrile/water=30/70; Detection, UV 240 nm; Flow rate, 1 ml/min; Injection volume, 10 µl. The mean value and standard deviation were obtained with Microsoft Excel. The HPLC analysis showed that 26.38% of the prodrug was released as the form of dexamethasone. Since the theoretical drug content of PEG-DiDex is 26.75%, 98.6% of theoretical Dex content was covalently conjugated to the prodrug.

PEG-DiDex Dimer Treatment of Lupus Nephritis

Experimental Animals and Drug Treatment

Figure 10A:
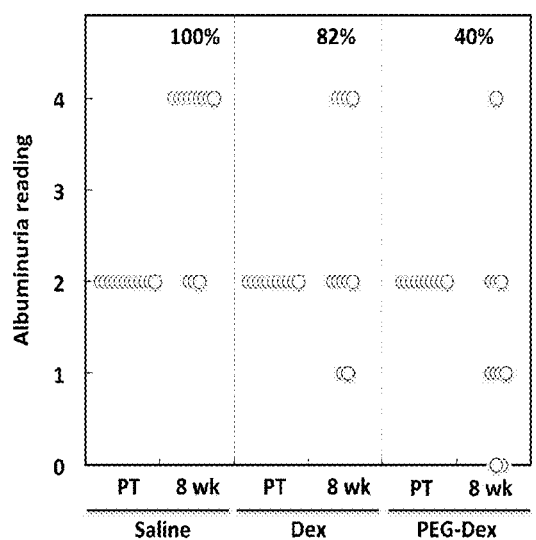
FIGS. 10A and 10B illustrate that PEG-DiDex ameliorates albuminuria, extends lifespan and attenuates development of severe nephritis. (A), Albuminuria data for mice in saline (n=12), Dex (n=1), and PEG-DiDex (n=1) treatment groups is illustrated at the pretreatment (PT) and 8-week time points. The incidence of albuminuria at the 8-week time point for each group is shown (in %) in upper right corner of each sub-section. (B), A Kaplan-Meier survival curve for each treatment group is shown.

Beginning at 28 weeks of age, (NZB×NZW)F1 female mice (Jackson Laboratories, Bar Harbor, Me.) groups of mice were randomized into saline, Dex and PEG-DiDex groups and monitored weekly for albuminuria using Albustix dipsticks (Siemens Corp., Washington D.C.). Only the mice in each group with established nephritis, evidenced by sustained albuminuria (≥ 100 mg/dl) over a monitoring period of 2 weeks, were officially enrolled in the study. PEG-DiDex (106 mg/kg, containing 28 mg/kg of dexamethasone, n=10) and saline groups (n=12) were administered via a single injection per month. The free Dex group was given daily i.v. injections of dexamethasone 21-phosphate disodium (n=1, Dex, 1.32 mg/kg, containing 1.00 mg/kg of dexamethasone, Hawkins, Inc., Minneapolis, Minn.). Treatment continued for 8 weeks. Mice were monitored for an additional two weeks after cessation of treatment. After that, the mice were euthanized and the spleen, kidneys, adrenal glands and left femur were harvest. PEG-DiDex reverses established albuminuria, extends survival rates and reduces incidence of severe nephritis To determine if PEG-DiDex could ameliorate established nephritis, PEG-DiDex was administered monthly to (NZB× NZW)F1 females beginning at ~28 weeks of age, after they had developed nephritis, as evidenced by sustained albuminuria. Treatment was continued for 8 weeks. Two control groups, one receiving dose equivalent daily Dex and the other receiving a monthly dose of saline, were also treated for 8 weeks. Mice were monitored for an additional two weeks after cessation of treatment. Over the entire experimental time course, albuminuria not only persisted in 100% of the mice in the saline treated group, but also increased in severity in most of these mice (75%) (FIG. 10A). However, in the Dex group, albuminuria was detected in 82% of the mice, and intensified in just 36% of the Dex treated mice, indicating that Dex treatment could prevent progression of renal dysfunction.

By contrast, albuminuria resolved in 60% of the mice in the PEG-DiDex group (FIG. 10A), and 20% of the PEG-DiDex treated mice even showed negative albuminuria and thoroughly recovered. The fraction of mice in the PEG-DiDex group that showed resolution of albuminuria was significantly greater than that in the Dex treated group, indicating that PEG-DiDex is more effective than dose equivalent Dex in resolving albuminuria associated with lupus nephritis.

Figure 10B:
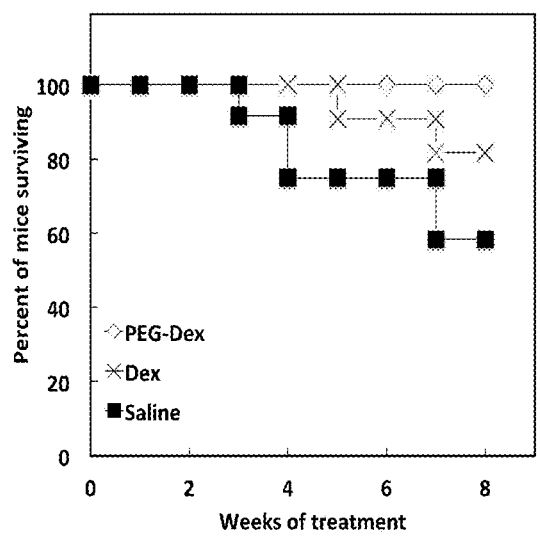

Prior to the end of the experiment, ~42% of mice in the saline group and ~18% of Dex treated mice were euthanized due to severe nephritis (FIG. 10B). All mice in the PEG-DiDex group survived during the entire treatment period, indicating that PEG-DiDex treatment increased the fraction of mice surviving until the end of the treatment period. These data indicate that PEG-DiDex can extend the lifespan of (NZB×NZW)F1 mice.

Evaluation of Treatment-Induced Side Effects

PEG-DiDex Treatment does not Affect Bone Quality

Peripheral dual x-ray absorptiometry was performed with a scanning speed of 20 mm/second and resolution of 0.2×0.2 mm. The micro-CT scanning parameters were as follows: voltage 48 kV, current 187 µA, exposure time 620 msec, resolution 6.07 µm, and aluminum filter 0.5 mm. Three-dimensional reconstructions were performed with NRecon and DataViewer software (SkyScan). Trabecular bone was selected for analysis based on a polygonal region of interest within the center of the femur, starting at 20 slices (0.25 mm) proximal from the growth plate and extending proximally 80 slices (0.99 mm) further. Trabecular bone volume/tissue volume (BV/TV), the mean bone mineral density (BMD), trabecular number, and trabecular thickness were quantified with CTAn software (SkyScan).

Osteoporosis is a major adverse side effect of long-term use of GCs. To investigate the impact of PEG-DiDex on the skeleton, the femoral BMD and micro-architecture were evaluated. Trabecular bone volume/tissue volume (BV/TV) and trabecular thickness did not differ significantly from the means in the saline group (FIG. 7B, C; $P>0.05$), indicating that PEG-DiDex did not negatively affect BV/TV or trabecular thickness of the bone. The mean bone mineral density (BMD) and trabecular number in the femurs of PEG-DiDex treated mice were significantly higher than that observed in both saline and Dex group (FIG. 7A, D; $P<0.05$). Compare to NZW mice (as a healthy control), even the saline group exhibits significantly lower values of BMD, BV/TV and trabecular number (data not shown). Thus, PEG-DiDex treatment not only avoided osteoporosis induced by long-term administration of GCs, but also ameliorated bone lesion caused by other complications of SLE, rheumatoid arthritis, for example.

PEG-DiDex Treatment does not Lead to Peripheral White Blood Cells Reduction

GC therapy is associated with immunosuppression. Therefore, we monitored peripheral white blood cell (WBC) counts and during the experimental time course. In comparison of healthy control mice, peripheral white blood cell (WBC) counts were significantly lower in the other three groups (data not shown). But the PEG-DiDex group exhibited significantly greater WBC counts compared to the Dex group (FIG. 7D; $P<0.05$). The WBC counts of Dex group were lower than the saline group, even though there was no significant difference. The WBC counts did not differ significantly between PEG-DiDex and saline groups. Thus, PEG-DiDex treatment ameliorates peripheral WBC reduction induced by GC therapy.

PEG-DiDex Treatment does not Induce Adrenal Gland Atrophy

GC therapy causes suppression of hypothalamic-pituitary-adrenal (HPA) axis and atrophy of the adrenal glands. Therefore, at necropsy, we determined the mass of the adrenal glands in each mouse. The mean adrenal mass in the Dex group was significantly lower than the PEG-DiDex group (FIG. 7F; P<0.05). There was no significant difference in adrenal gland mass between the PEG-DiDex and saline groups (FIG. 7F; P>0.05). These data suggest that treatment with PEG-DiDex did not induce adrenal gland atrophy.

In summary, PEG-DiDex treatment would potentiate lupus nephritis resolution in terms of prolonged lifespan and reduced incidence of severe nephritis, as well as a reduced risk of systemic toxicities and side effects.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as claimed in the appending claims.

All publications, patents, and patent applications cited in this application are herein incorporated by reference to the same extent as if each individual publication, patent, or patent application was specifically and individually indicated to be incorporated herein by reference.

What is claimed is:

1. A pharmaceutical composition comprising a compound of formula (I):

$$R^1O\underset{n}{(\phantom{x}O\phantom{x})}A-B-D-E-(R^2)_m \quad (I)$$

$$R^2 = -Z-Y-X-T-Q-P-G-N-[\text{dexamethasone}]_w$$

or a pharmaceutically acceptable salt thereof, and a pharmaceutically acceptable carrier, adjuvant, diluent, or vehicle, wherein:
n is an integer from 3 to 500;
m is an integer from 1 to 5;
w is an integer from 1 to 5;
A is absent, $C_1$-$C_6$ alkylene, or $C_6$-$C_{10}$ arylene;
B is absent, $NR^4$, O, or C(O);
D is absent, $NR^4$, O, C(O), or $CR^5R^5$;
E is absent, $C_1$-$C_6$ alkylene, or a linker comprising a branched structure capable of connecting to two or more $R^2$ groups, said linker optionally comprising one, two, or more heteroatoms independently selected from the group consisting of O, S, and N;
G is absent, $NR^4$, or O;
P is absent or C(O);
Q is absent, $C_6$-$C_{10}$ arylene, or $C_1$-$C_6$ alkylene;
T is absent, $C_1$-$C_6$ alkylene, $C_6$-$C_{10}$ arylene, or C(O);
X is absent, O, S, or $NR^4$;
Y is absent, C(O), $C_6$-$C_{10}$ arylene, or $C_1$-$C_6$ alkylene;
Z is absent, $NR^4$, O, $C_1$-$C_6$ alkylene, or a linker comprising a branched structure capable of connecting to one or more dexamethasone moieties, said linker optionally comprising one or more heteroatoms independently selected from the group consisting of O, S, and N;
$R^1$ is H, $C_1$-$C_6$ alkyl, $C_2$-$C_6$ alkenyl, $C_2$-$C_6$ alkynyl, $C_6$-$C_{10}$ aryl, 5-10 membered heteroaryl, or 5-10 membered heterocyclyl, each group except H optionally substituted by one to five substituents independently selected from the group consisting of $C_1$-$C_4$ alkyl, $C_1$-$C_4$ haloalkyl, halogen, oxo (=O), —$NR^aR^b$, —$NO_2$, —CN, —$OR^3$, and —$SR^3$; or alternatively, $R^1$ is —$CH_2$-A-B-D-E-$(R^2)_m$;
$R^3$ at each occurrence is independently H, $C_1$-$C_4$ alkyl, or $C_1$-$C_4$ haloalkyl;
$R^4$ at each occurrence is independently H or $C_1$-$C_4$ alkyl;
$R^5$ at each occurrence is independently H, $C_1$-$C_4$ alkyl, or $C_1$-$C_4$ haloalkyl;
$R^a$ and $R^b$ are each independently H or $C_1$-$C_4$ alkyl; and
wherein when any of groups A, B, D, E, G, P, Q, T, X, Y, and Z is absent, its two available adjacent groups are single-bonded to each other directly;
provided, however, that if the compound of formula (I) is a compound of formula:

[structure of PEGylated dexamethasone carbamate/hydrazone]

then n is greater than 30.

2. The pharmaceutical composition of claim 1, wherein E is a linker comprising a branched structure capable of covalently bonding to two or more $R^2$ groups, said linker optionally comprising one or more heteroatoms independently selected from the group consisting of O, S, and N.

3. The pharmaceutical composition of claim 1, wherein Z is a linker comprising a branched structure capable of covalently bonding to two or more dexamethasone moieties, said linker optionally comprising one or more heteroatoms independently selected from the group consisting of O, S, and N.

4. The pharmaceutical composition of claim 1, wherein E and Z are each independently selected from the group consisting of absent, $C_1$-$C_4$ alkylene, an amino acid-based linker, a citric acid-based linker, a glycerol-based linker, a tris(2-aminoethyl)amine-based linker, a pentaerythritol-based linker, and a pentetic acid-based linker, respectively having a formula as follows:

[structure]

amino acid-based

-continued

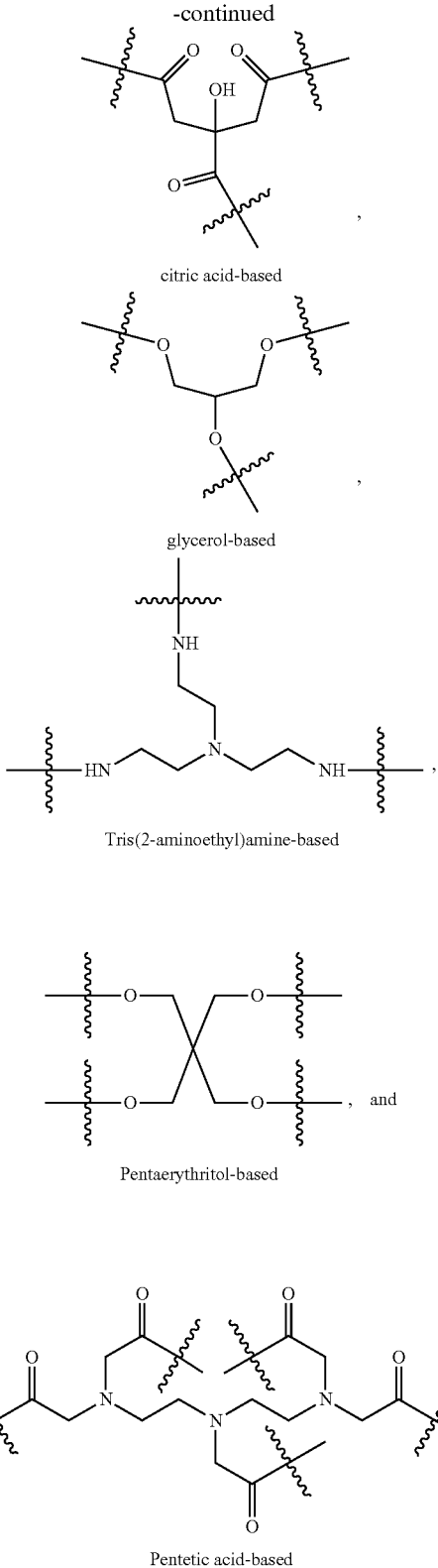

citric acid-based glycerol-based

Tris(2-aminoethyl)amine-based

Pentaerythritol-based, and

Pentetic acid-based wherein i and j are each independently 0 or an integer select from 1 to 5.

5. The pharmaceutical composition of claim 4, wherein:
w is 1;
Z is absent or $C_1$-$C_4$ alkylene;

E is selected from the group consisting of:

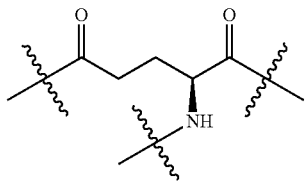

glutamic acid-based

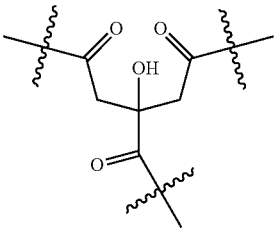

citric acid-based

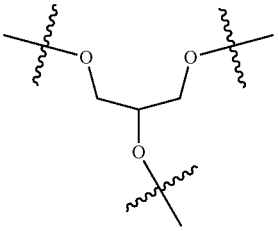

glycerol-based

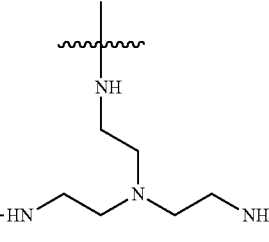

Tris(2-aminoethyl)amine-based

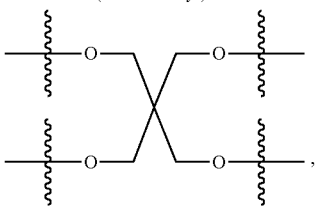

Pentaerythritol-based, and

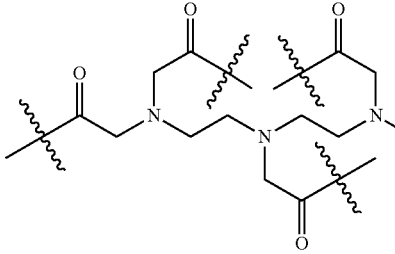

Pentetic acid-based

6. The pharmaceutical composition of claim 1, wherein m is 1; w is 1; and A, B, D, E, and Z are all absent, and the compound is a compound of formula (II):

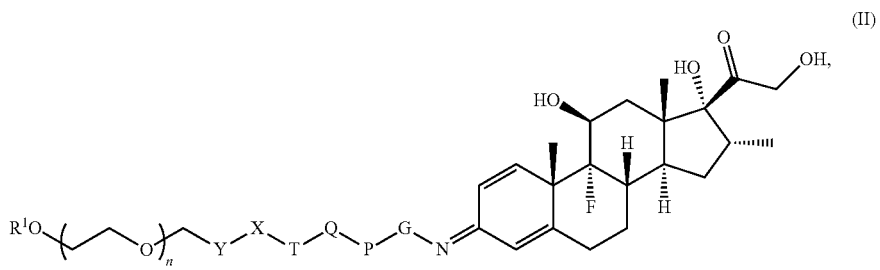

or a pharmaceutically acceptable salt thereof.

7. The pharmaceutical composition of claim 6, wherein $R^1$ is $CH_3$; Y is C(O); X is NH; and T, Q, P, and G are all absent, and the compound is a compound of formula:

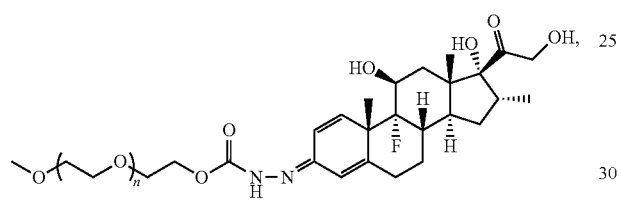

or a pharmaceutically acceptable salt thereof.

8. The pharmaceutical composition of claim 5, wherein A is C(O); B and D are absent; E is the amino acid based linker; m is 2; w is 1; Z and Y are absent, and X is NH, and the compound is a compound of formula (III):

or a pharmaceutically acceptable salt thereof, wherein:
i=0 or an integer from 1 to 5;
j=0 or an integer from 1 to 5;
G=absent, $NR^4$, or O;
P=absent or C(O);
Q=absent, $C_6$-$C_{10}$ arylene, or $C_1$-$C_6$ alkylene;
T=absent, $C_1$-$C_6$ alkylene, $C_6$-$C_{10}$ arylene, or C(O);
X=absent, O, S, or $NR^4$;
Y=absent or $C_1$-$C_6$ alkylene;
$R^1$=H or $C_1$-$C_6$ alkyl, $C_2$-$C_6$ alkenyl, $C_2$-$C_6$ alkynyl, $C_6$-$C_{10}$ aryl, or 5-10 membered heteroaryl, 5-10 membered heterocyclyl, each group except H optionally substituted by one to three substituents independently selected from the group consisting of $C_1$-$C_4$ alkyl, $C_1$-$C_4$ haloalkyl, halogen, oxo (=O), —$NR^aR^b$, —$NO_2$, —CN, —$OR^3$, and —$SR^3$;
$R^3$ at each occurrence is independently H, $C_1$-$C_4$ alkyl, or $C_1$-$C_4$ haloalkyl;
$R^4$ at each occurrence is independently H or $C_1$-$C_4$ alkyl;
$R^a$ and $R^b$ are each independently H or $C_1$-$C_4$ alkyl; and
wherein when any of groups G, P, Q, T, X, and Y is absent, its two available adjacent groups are single-bonded to each other directly.

9. The pharmaceutical composition of claim 8, wherein i is 0; j is 2; E is a glutamic acid based linker having a formula:

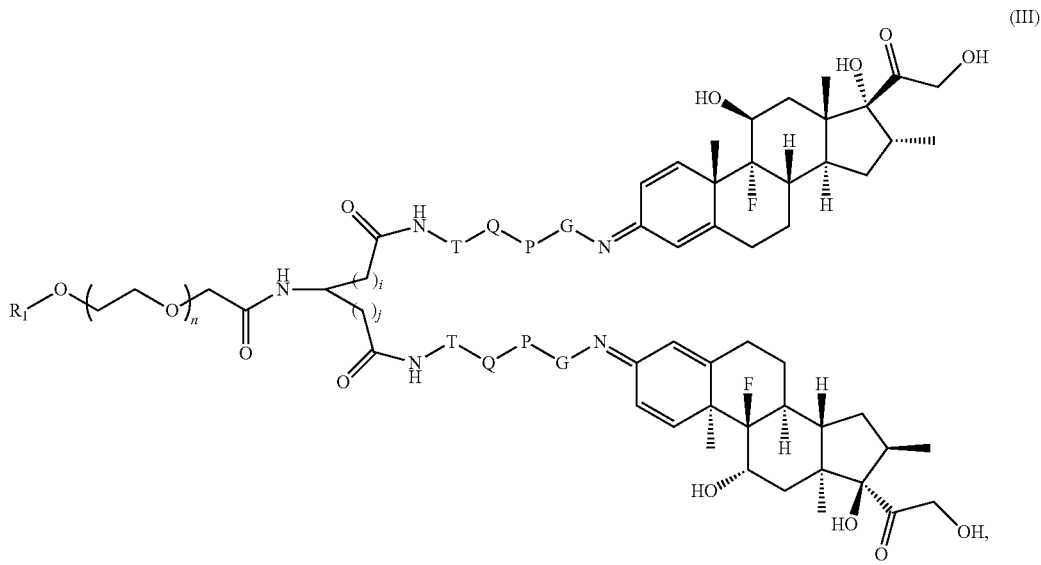

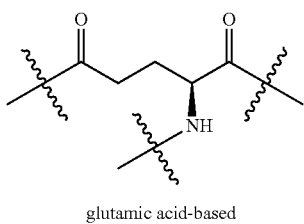

glutamic acid-based

10. The pharmaceutical composition of claim 8, wherein i is 0, j is 2, X is NH; and Q is methylene, P is C(O), G is NH, and the compound is a compound of formula:

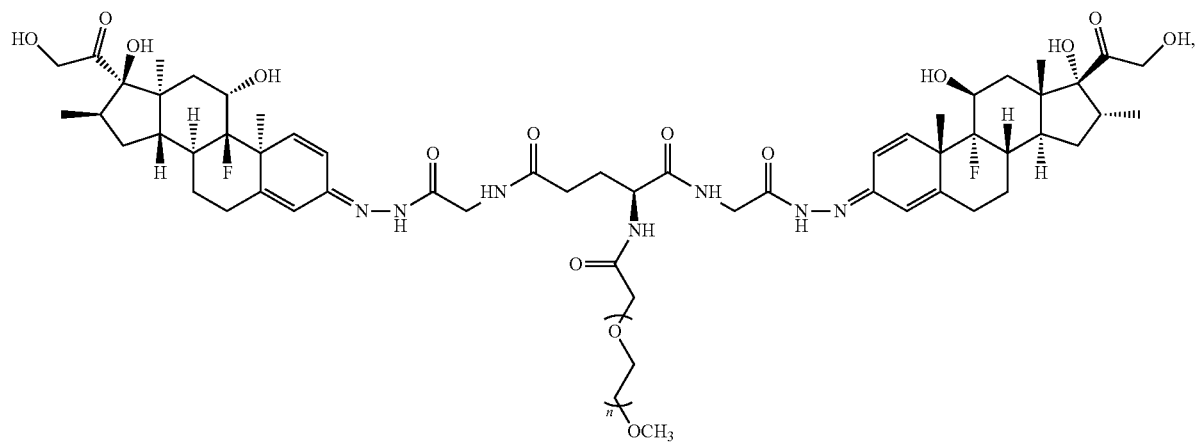

or a pharmaceutically acceptable salt thereof.

11. The pharmaceutical composition of claim 5, wherein A is methylene, B is NH, m is 1, w is 2, E is a citric acid based linker, Z is NH, and the compound is a compound of formula (IV):

G=absent, NR$^4$, or O;
P=absent or C(O);
Q=absent, $C_6$-$C_{10}$ arylene, or $C_1$-$C_6$ alkylene;
T=absent, $C_1$-$C_6$ alkylene, $C_6$-$C_{10}$ arylene, or C(O);
X=absent, O, S, or NR$^4$;
Y=absent or $C_1$-$C_6$ alkylene;
R$^1$=H or $C_1$-$C_6$ alkyl, $C_2$-$C_6$ alkenyl, $C_2$-$C_6$ alkynyl, $C_6$-$C_{10}$ aryl, or 5-10 membered heteroaryl, 5-10 membered heterocyclyl, each group except H optionally substituted by one to three substituents independently selected from the group consisting of $C_1$-$C_4$ alkyl, $C_1$-$C_4$ haloalkyl, halogen, oxo (=O), —NR$^a$R$^b$, —NO$_2$, —CN, —OR$^3$, and —SR$^3$;

R$^3$ at each occurrence is independently H, $C_1$-$C_4$ alkyl, or $C_1$-$C_4$ haloalkyl;

R$^4$ at each occurrence is independently H or $C_1$-$C_4$ alkyl;

R$^a$ and R$^b$ are each independently H or $C_1$-$C_4$ alkyl; and

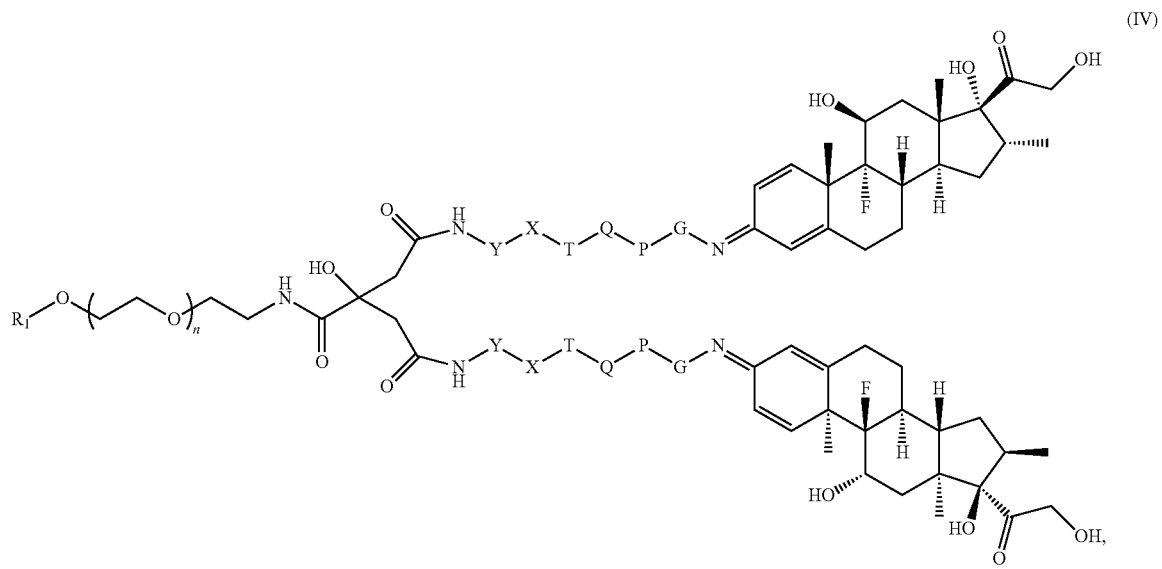

(IV)

or a pharmaceutically acceptable salt thereof, wherein:
i=0 or an integer from 1 to 5;
j=0 or an integer from 1 to 5;

wherein when any of groups G, P, Q, T, X, and Y is absent, its two available adjacent groups are single-bonded to each other directly.

12. The pharmaceutical composition of claim 11, wherein G, P, Q, T, X, and Y are all absent, and the compound is a compound of formula:

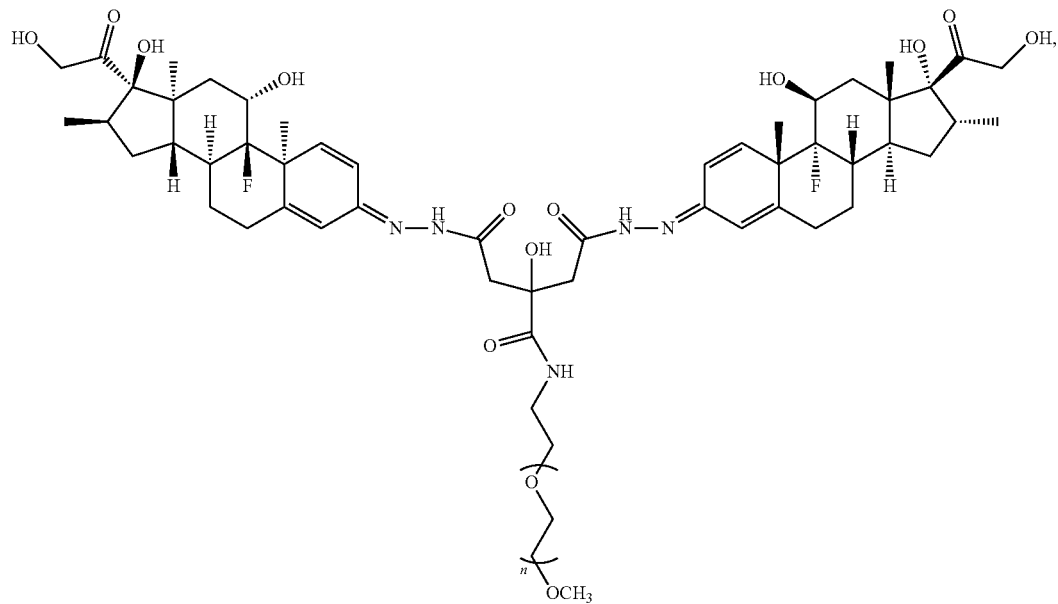

or a pharmaceutically acceptable salt thereof.

13. The pharmaceutical composition of claim 5, wherein m is 3, w is 1, A is methylene, B is NH, D is C(O) and E is a pentaerythritol-based linker, and the compound is a compound of formula (V):

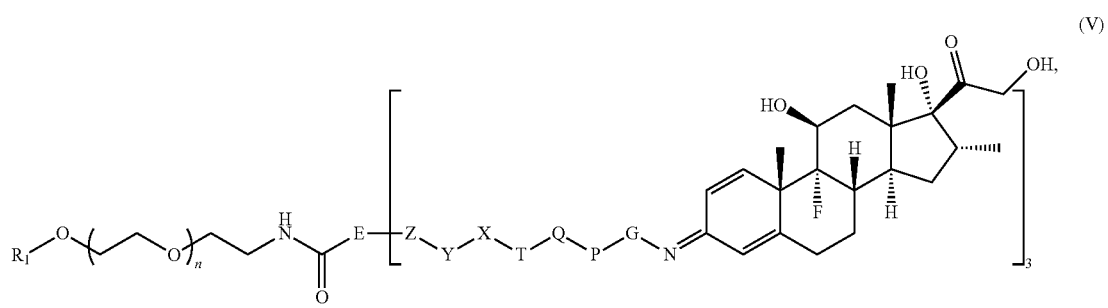

(V)

or a pharmaceutically acceptable salt thereof.

14. The pharmaceutical composition of claim 13, wherein Y is C(O); X is NH; and G, P, Q, and T are all absent, and the compound is a compound of formula:

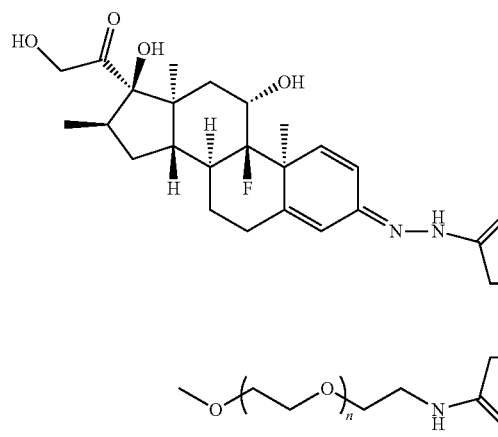
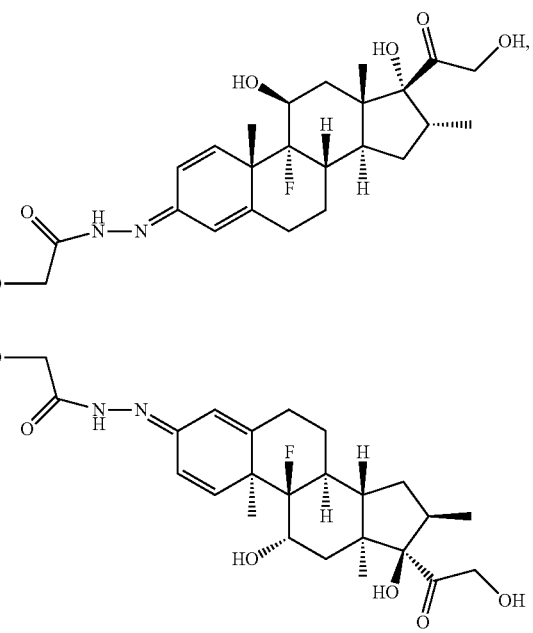
or a pharmaceutically acceptable salt thereof.
15. The pharmaceutical composition of claim 1, having a structure of any one of formulas (VI)-(XI):
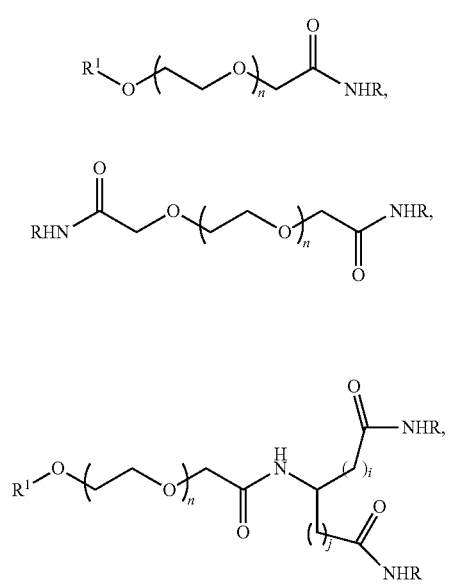
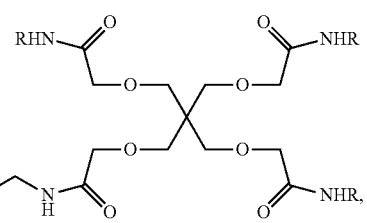

73
wherein R is selected from the group consisting of:
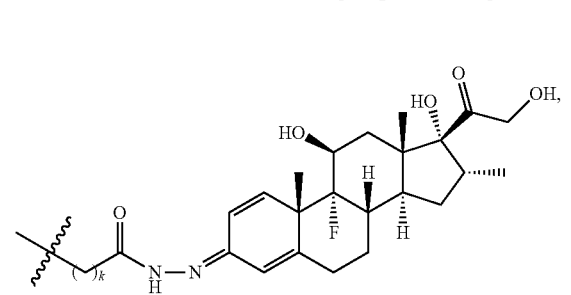
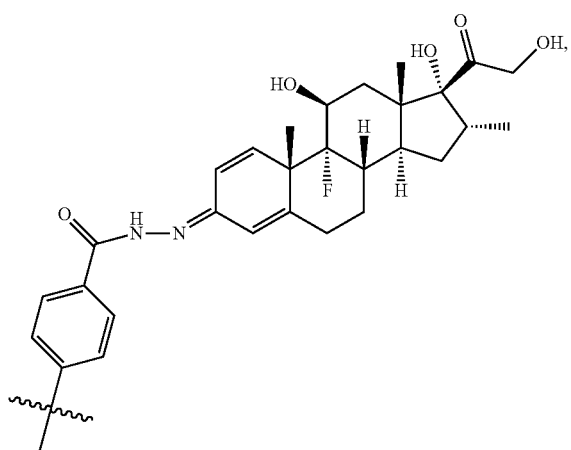
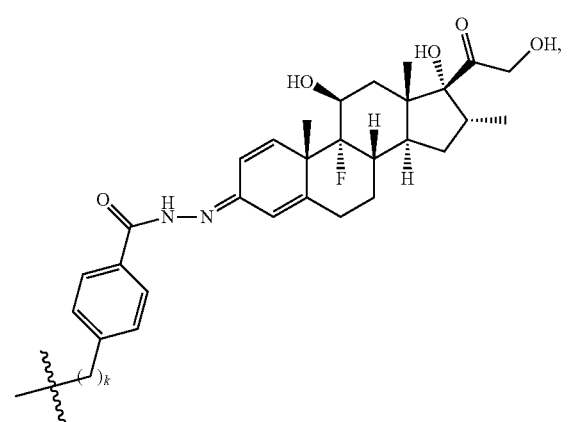
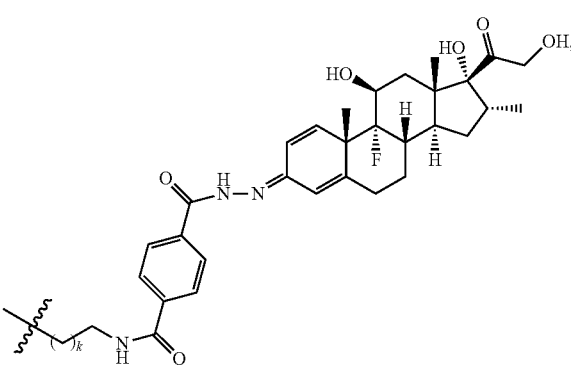
74
-continued
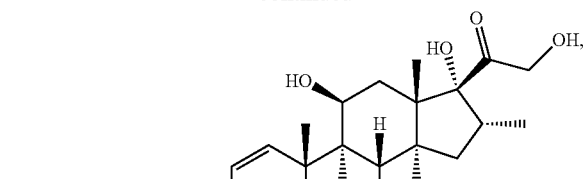
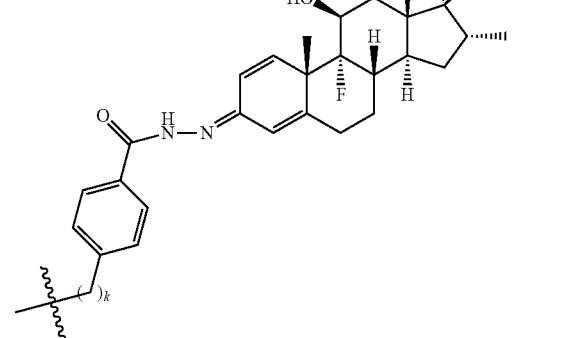
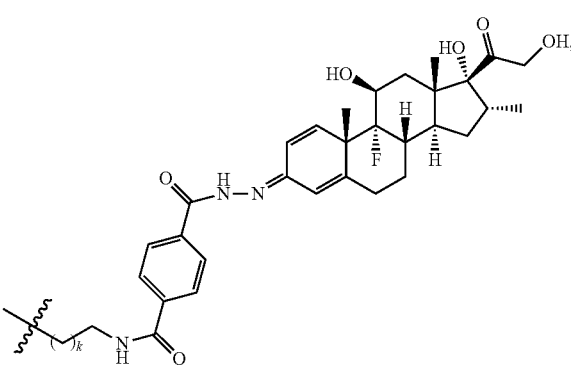
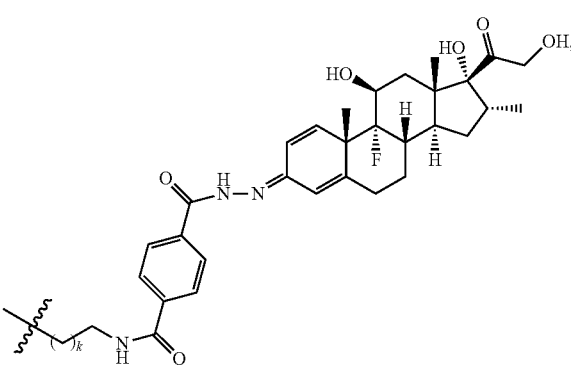

-continued

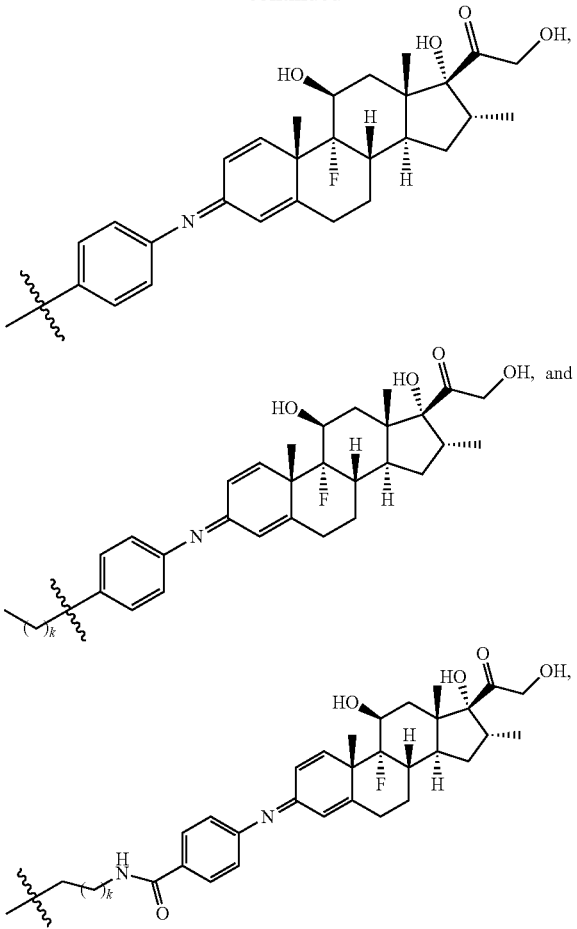

wherein k at each occurrence is independently an integer selected from 1 to 10.

16. The pharmaceutical composition of claim 15, wherein E is a glutamic acid based linker having a formula:

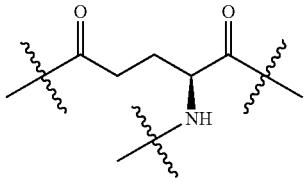

glutamic acid-based

17. The pharmaceutical composition of claim 1, wherein n is 40 to 50.

18. The pharmaceutical composition of claim 1, wherein the composition is in oral, nasal, topical, buccal, sublingual, rectal, vaginal, intravenous, intramuscular, intraperitoneal, or other parenteral form.

19. The pharmaceutical composition of claim 1 in vaporization-ready, nebulization-ready, nanoparticle formulation, or liposomal formulation.

20. The pharmaceutical composition of claim 1, further comprising a second therapeutic agent selected from the group consisting of a noisteroidal anti-inflammatory drug (NSAID), a glucocorticoid, a disease-modifying anti-rheumatic drug (DMARD), and a biologic drug.

21. The pharmaceutical composition of claim 20, wherein the NSAID is selected from the group consisting of aspirin, naproxen, and celecoxib; the glucocorticoid is selected from the group consisting of dexamethasone, prednisone, and betamethasone; and the DMARD is selected from the group consisting of methotrexate, leflunomide, sulfasalazine, and hydroxychloroquine.

\* \* \* \* \*